(12) United States Patent
Tucker et al.

(10) Patent No.: US 7,576,179 B2
(45) Date of Patent: *Aug. 18, 2009

(54) MORAXELLA CATARRHALIS OUTER MEMBRANE PROTEIN-106 POLYPEPTIDE, GENE SEQUENCE AND USES THEREOF

(75) Inventors: Kenneth Tucker, Frederick, MD (US); Laura Plosila, Cary, NC (US); Ulrich F. Tillman, Mount Laurel, MD (US)

(73) Assignee: Emergent Product Development of Gaithersburg, Inc., Gaithersburg, MD (US)

( * ) Notice: Subject to any disclaimer, the term of this patent is extended or adjusted under 35 U.S.C. 154(b) by 62 days.

This patent is subject to a terminal disclaimer.

(21) Appl. No.: 11/580,854

(22) Filed: Oct. 16, 2006

(65) Prior Publication Data

US 2007/0087019 A1    Apr. 19, 2007

Related U.S. Application Data

(60) Division of application No. 09/813,214, filed on Mar. 20, 2001, now Pat. No. 7,128,910, which is a division of application No. 08/968,685, filed on Nov. 12, 1997, now Pat. No. 6,214,981, which is a continuation-in-part of application No. 08/642,712, filed on May 3, 1996, now Pat. No. 7,341,727.

(51) Int. Cl.
   *C07K 14/00* (2006.01)
   *A61K 39/00* (2006.01)
(52) U.S. Cl. .................. 530/350; 424/185.1
(58) Field of Classification Search ............ 424/185.1
   See application file for complete search history.

(56) References Cited

U.S. PATENT DOCUMENTS

| | | | |
|---|---|---|---|
| 4,879,213 A * | 11/1989 | Fox et al. .................. 435/5 |
| 5,607,846 A | 3/1997 | Murphy et al. | |
| 5,808,024 A | 9/1998 | Sasaki et al. | |
| 6,335,018 B1 | 1/2002 | Sasaki et al. | |
| 6,440,424 B1 | 8/2002 | Sasaki et al. | |
| 6,440,425 B1 | 8/2002 | Sasaki et al. | |
| 6,706,269 B1 | 3/2004 | Ruelle | |
| 6,764,834 B1 | 7/2004 | Ruelle | |
| 7,128,910 B2 * | 10/2006 | Tucker et al. ............ 424/184.1 |

FOREIGN PATENT DOCUMENTS

| WO | WO 93/03761 | 4/1993 |
|---|---|---|
| WO | WO 96/34960 | 11/1996 |

OTHER PUBLICATIONS

Aebi et al., 1997, Infection & Immunity 65:4367-4377.
Bartos & Murphy, 1988, J. Infect. Dis. 158:761-765.
Beck-Sickinger, et al, 1993, Epitope mapping: synthetic approaches to the understanding of molecular recognition in the immune system, Pharm Acta Helv., 68(1):3-20.
Bogosian et al., 1993, Gene, 137:17-22.
Brunham, et al, *Chlamydia trachomatis* antigens: role in immunity and pathogenesis. Infectious Agents and Disease (1994) 3(5):218.
Cain, et al, 1994, Solubilization of glycosyl-phosphatidylinositol-anchored proteins in guiescent and stimulated neutrophils, Biochim Biophys Acta., 1235(1):69-78.
Chen et al. Infection and Immunity, vol. 64, No. 6, pp. 1900-1905, 1996.
Corradin, 1990, Antigen processing and presentation, Immunol Lett, 25(1-3): 11-13.
Gu, et al. Infection and Immunity, vol. 66, No. 5, pp. 1891-1897, May 1998.
Hays, et al, Total genome polymorphism and low frequency of intragenomic variation in uspA1 and uspA2 genes of *Moraxella catarrhalis* in otitis prone and non-prone children up to two years of age. Vaccine (2003), 21:1118.
Helminen et al., 1993, Infect. Immun. 61:2003-2010.
Helminen et al., 1994, J. Infect. Dis. 170:867-87.
Hu et al. Infection and Immunity vol. 68, No. 9, pp. 4980-4985, 2000.
Kellens et al., 1995, Infection 23:37-41.
Klingman & Murphy, 1994, Infect. Immun. 62: 1150-1155.
Kyd et al., 1988, Outer-membrane antigen expression by *Moraxella* (*Branhamella*) *catarrhalis* influences pulmonaryclearance, J. Med. Microbiol., 47:159-168.
Kyd, et al., Vaccine, vol. 18, pp. 398-406, 2000.
Lane, et al, 1993, Epitope mapping using bacteriophage peptide libraries, Curr Opin Immunol., 5(2):268-71.
Mbaki et al., 1987, Tohuku J. Exp. Med. 153:111-121.
Murphy & Bartos, 1989, Infect. Immun. 57:2938-2941.
Murphy & Loeb, 1989, Microbial Pathogen 6:159-174.
Murphy et al., 1990, Amer. J. Med. 88 (5A):41S-45S.
Murphy et al., 1993, Molecul. Microbiol. 10:87-97.
Nebl, et al, 2002, Proteomic analysis of a detergent-resistant membrane skeleton from neutrophil plasma membranes, J. Bio Chem, 227 (45):43399-43409.
Poolman, 1999, Handb. Exp. Pharmacol. 133 (Vaccines) 235-248.
Rikitomi et al., 1991, Scand. J. Infect. Dis. 23: 559-567.
Samukawa et al. JID, vol. 181, pp. 1842-1845, 2000.
Sarwar et al., 1992, Infect. Immun. 60:804-809.
Sasaki et al., 1996, Abstract of the 96th Gen Mtg of the Amer. soc for Microbiol., may 19-27, 1996, B-181.

(Continued)

*Primary Examiner*—Mark Navarro
(74) *Attorney, Agent, or Firm*—Gilberto M. Villancorta; Sunit Talapatra; Foley & Lardner LLP

(57) ABSTRACT

The invention discloses the *Moraxella catarrhalis* outer membrane protein-106 (OMP106) polypeptide, polypeptides derived therefrom (OMP106-derived polypeptides), nucleotide sequences encoding OMP106 polypeptides, and antibodies that specifically bind the OMP106 polypeptide and/or OMP106-derived polypeptides. Also disclosed are immunogenic, prophylactic or therapeutic compositions, including vaccines, comprising OMP106 polypeptide and/or OMP106-derived polypeptides. The invention additionally discloses methods of inducing immune responses to *M. catarrhalis* and *M. catarrhalis* OMP106 polypeptides and OMP106-derived polypeptides in animals.

5 Claims, 13 Drawing Sheets

OTHER PUBLICATIONS

Figure 1:
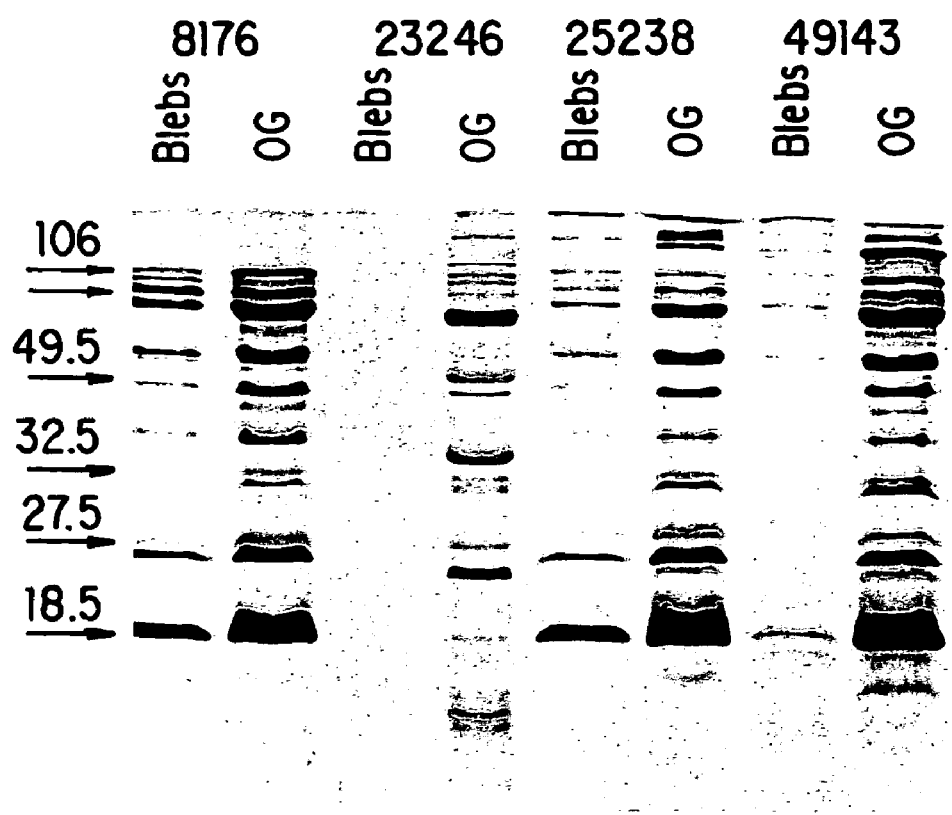

Sethl, et al, Antigenic heterogeneity and molecular analysis of CopB of *Moraxella (Brunharnella) catarrhalis*. Infection and Immunity (1997) 65(9):3666.

Soto-Hernandez et al., 1989, J. Clin. Microbiol. 27:903-908.

Tucker et al., 1994, Annual Meeting of Amer. Soc. Microbiol. Abstr. D124.

Unhanand et al., 1992, J. Infect. Dis. 165:644-650.

Verduin et al., 1995, Abstr. of the 95th Gen. Mtg. of the Amer. Soc. for Microbiol. p. 189 Abstr. B-137.

Vretou, et al, Identification of protective epitopes by sequencing of the Major Outer Membrane Protein gene of a variant strain of *Chlamydia psittaci* serotype 1. Infection and Immunity (2001) 69(1):607.

Westbay, et al, Dissociation of Immune determinants of Outer Membrane Proteins of *Chlamydia psittaci* strain guinea pig inclusion conjunctivitis. Infection and Immunity (1994) 62(12):5614.

Zhang, et al, Comparison of the Major Outer Membrane Protein (MOMP) gene of mouse penumonitis (MoPn) and hamster SFPD strains of *Chlamydia trachomatis* with other *Chlamydia* strains. Mo. Biol. Evol. (1993), 10(6):1327.

* cited by examiner

MORAXELLA CATARRHALIS OUTER MEMBRANE PROTEIN-106 POLYPEPTIDE, GENE SEQUENCE AND USES THEREOF

CROSS-REFERENCE TO RELATED PATENT APPLICATIONS

This application is a division of Ser. No. 09/813,214 filed Mar. 20, 2001, now U.S. Pat. No. 7,128,910, which is a division of Ser. No. 08/968,685 filed Nov. 12, 1997, now U.S. Pat. No. 6,214,981, which is a continuation in part of Ser. No. 08/642,712, filed May 3, 1996, now U.S. Pat. No. 7,341,727, the disclosures of which are incorporated by reference herein in their entirety.

INTRODUCTION

The present invention generally relates to the outer membrane protein-106 (OMP106) polypeptide of *Moraxella catarrhalis*. The invention encompasses a purified OMP106 polypeptide and polypeptides derived therefrom (OMP106-derived polypeptides). The invention also encompasses antibodies, including cytotoxic antibodies, that specifically bind the OMP106 polypeptide and/or OMP106-derived polypeptides. The invention further encompasses prophylactic or therapeutic compositions, including vaccines, that comprise OMP106 polypeptide and/or OMP106-derived polypeptides. The invention additionally provides methods of inducing immune responses to *M. catarrhalis* in mammals. The invention further provides isolated nucleotide sequences encoding the OMP106 polypeptide and OMP106-derived polypeptides, vectors having said sequences, and host cells containing said vectors.

BACKGROUND OF THE INVENTION

*Moraxella catarrhalis*, also known as *Moraxella (Branhamella) catarrhalis* or *Branhamella catarrhalis* and formerly known as *Neisseria catarrhalis* or *Micrococcus catarrhalis*, is a gram-negative bacterium frequently found in the respiratory tract of humans. *M. catarrhalis*, originally thought to be a harmless commensal organism, is now recognized as an important pathogen in upper and lower respiratory tract infections in animals. In humans, *M. catarrhalis* causes serious lower respiratory tract infections in adults with chronic lung disease, systemic infections in immunocompromised patients, and otitis media and sinusitis in infants and children. See Helminen et al., 1993, Infect. Immun. 61:2003-2010; Catlin, B. W., 1990, Clin. Microbiol. Rev. 3:293 320; and references cited therein.

2.1. Outer Membrane Proteins and Protective Antibodies

The outer surface components of *Moraxella catarrhalis* have been studied in attempts to understand the pathogenic process of *M. catarrhalis* infections and to develop useful therapeutic treatments and prophylactic measures against such infections. The outer membrane proteins (OMPs) in particular have received considerable attention as possible virulence factors and as potential vaccine antigens. *M. catarrhalis* has about 10 to 20 different OMPs with 6 to 8 of these, OMPs A to H, as the predominate species (Murphy and Loeb, 1989, Microbial Pathogen. 6:159-174). The molecular weights of OMPs A to H range from 97 to 20 kD, respectively. See Bartos and Murphy, 1988, J. Infect. Dis. 158:761-765; Helminen et al., 1993, Infect. Immun. 61:2003-2010; Murphy et al, 1993, Molecul. Microbiol. 10: 87-97; and Sarwar et al, 1992, Infect. Immun. 60:804 809. Comparisons of protein profiles by sodium dodecylsulfate polyacrylamide gel electrophoresis (SDS-PAGE) of outer membrane preparations from 50 *M. catarrhalis* strains show nearly homogeneous patterns of OMPs A to H (Bartos and Murphy, 1988, J. Infect. Dis. 158:761 765).

In addition to OMPs A to H, a high molecular weight OMP, designated HMW-OMP, having an apparent mass of 350 to 720 kD by SDS-PAGE has also been identified as another prominent surface component present in many strains of *M. catarrhalis*. HMW-OMP upon formic acid denaturation produces a single band of 120 to 140 kD and, thus, appears to be an oligomeric protein (Klingman and Murphy, 1994, Infect. Immun. 62:1150 1155). HMW-OMP appears to be the same protein as that designated UspA by Helminen et al., (1994, J. Infect. Dis. 170:867-872) and shown to be present in a number of *M. catarrhalis* strains.

In intact bacterium or bacterially-derived outer membrane vesicles, several of the above-identified OMPs present surface-exposed epitopes that elicit the production of antibodies that bind the OMPs. These antigenic OMPs include OMP E and OMP G (Murphy and Bartos, 1989, Infect. Immun. 57:2938-2941); OMP C/D (Sarwar et al., 1992, Infect. Immun. 60:804-809); CopB, an 80 kD OMP, (Helminen et al., 1993, Infect. Immun. 61:2003 2010); and UspA (Helminen et al., 1994, J. Infect. Dis. 170:867 872).

The therapeutic potential of antibodies to surfaced-exposed epitopes of CopB and UspA has been evaluated in an animal model. The model involved direct bolus inoculation of lungs of BALB/c VAF/Plus mice with a controlled number of *M. catarrhalis* cells and subsequent examination of the rate of pulmonary clearance of the bacteria (Unhanand et al., 1992, J. Infect. Dis. 165:644-650). Different clinical isolates of the *M. catarrhalis* exhibited different rates of clearance that correlated with the level of granulocyte recruitment into the infection site. Passive immunization with a monoclonal antibody directed to a surface-exposed epitope of either CopB or UspA increased the rate of pulmonary clearance of *M. catarrhalis* (Helminen et al., 1993, Infect. Immun. 61:2003-2010; Helminen et al., 1994, J. Infect. Dis. 170:867-872).

2.2. Bacterial/Host Cell Adherence and Hemagglutination

The adherence of bacterial pathogens to a host cell surface promotes colonization and initiates pathogenesis. See, E. H. Beachey, 1981, J. Infect. Dis. 143:325-345. Gram-negative bacteria typically express surface lectins that bind to specific oligosaccharides of glycoproteins and/or glycolipids on the host cell surface. Such lectins are often associated with pili or fimbriae. Bacterial adherence can also occur by non-specific binding resulting from hydrophobic and/or charge interaction with the host cell surface.

The mechanism of *M. catarrhalis* adherence to cells of the respiratory tract remains poorly understood. The organism adheres to cultured human oropharyngeal epithelial cells (Mbaki et al., 1987, Tohuku J. Exp. Med. 153:111 121). A study by Rikitomi et al. suggests that fimbriae may have a role in the adherence to such cells as fimbriae denaturation or treatment with anti-fimbriae antibodies reduced adherence by fimbriated strains (Rikitomi et al., 1991, Scand. J. Infect. Dis. 23:559-567). Fimbriae mediated binding, however, cannot be the sole basis of this adherence as the most highly adhering strain, among the several examined, was a non-fimbriated strain.

Hemagglutination reactions often replace the more complicated adherence assays in classifying bacterial adhesins. However, Rikitomi et al. found no correlation between human oropharyngeal epithelial cell adherence and hemagglutination by *M. catarrhalis* strains (Id.). That is three highly adhering strains did not agglutinate human erythrocytes. Thus, different binding mechanisms are involved in human oropharyngeal epithelial cell adherence and hemagglutination.

By contrast, a recent study by Kellens et al. suggests that hemagglutination by M. catarrhalis is correlated with host cell adherence (Kellens et al., 1995, Infection 23:37-41). However, this study employed an adherence assay based on bacterial binding to porcine tracheal sections. It is unclear whether porcine tracheal tissue can be considered homologous to human respiratory tract tissue with respect to adherence by pathogenic strains of M. catarrhalis.

Notwithstanding the problematic adherence assay, Kellens et al. examined the hemagglutination activities of eighty-some clinical isolates of M. catarrhalis (Kellens et al., 1995, Infection 23:37-41). Nearly three-quarters of the examined strains agglutinated human, rabbit, guinea pig, dog or rat erythrocytes, while the remaining strains did not. The agglutination activities for some of the hemagglutinating stains were further characterized and shown to be calcium ion dependent and inhibited by trypsin digestion or high-temperature treatment or addition of D-glucosamine or D-galactosamine.

A survey of hemagglutinating and non-hemagglutinating M. catarrhalis strains by Tucker et al. has shown that all strains bind the glycolipid gangliotetraosylceramide but only hemagglutinating strains bind the glycolipid globotetraosylceramide (Tucker et al., 1994, Annual Meeting of Amer. Soc. Microbiol., Abstract No. D124). Moreover, M. catarrhalis hemagglutination activity was shown to be inhibited by various monosaccharides that comprise the carbohydrate moiety of globotetraosylceramide. These observations led Tucker et al. to suggest that M. catarrhalis hemagglutinates by binding to globotetraosylceramides in the cell membranes of susceptible erythrocytes, including those of human red blood cells. To date, no prior art has identified a molecule on the outer surface of M. catarrhalis that is responsible for either host cell adherence or hemagglutination.

Citation or identification of any reference in this section or any other section of this application shall not be construed as an indication that such reference is available as prior art to the present invention.

SUMMARY OF THE INVENTION

The present invention encompasses the OMP106 polypeptide of M. catarrhalis and OMP106-derived polypeptides and methods for making said polypeptides. The invention also encompasses antisera and antibodies, including cytotoxic antibodies, specific for the OMP106 polypeptide and/or OMP106-derived polypeptides. The invention further encompasses immunogenic, prophylactic or therapeutic compositions, including vaccines, comprising one or more of said polypeptides. The invention additionally encompasses nucleotide sequences encoding said polypeptides. The invention further encompasses immunogenic, prophylactic or therapeutic compositions, including vaccines, comprising an attenuated or inactivated non-hemagglutinating M. catarrhalis cultivar.

The present invention has many utilities. For example, the OMP106 polypeptide and OMP106-derived polypeptides may be used as ligands to detect antibodies elicited in response to M. catarrhalis infections (e.g., in diagnosing M. catarrhalis infections). The OMP106 polypeptide and OMP106-derived polypeptides may also be used as immunogens for inducing M. catarrhali-specific antibodies. Such antibodies are useful in immunoassays to detect M. catarrhalis in biological specimens. The cytotoxic antibodies of the invention are useful in passive immunizations against M. catarrhalis infections. The OMP106 polypeptide and OMP106-derived polypeptides may further be used as active ingredients in vaccines against M. catarrhalis infections.

The invention is based on the surprising discovery that hemagglutinating M. catarrhalis strains and cultivars have an outer membrane protein, OMP106 polypeptide, which is about 180 kD to about 230 kD in molecular weight, and that non-hemagglutinating M. catarrhalis strains and cultivars either do not have OMP106 polypeptide or have inappropriately-modified OMP106 polypeptide which is inactive in hemagglutination and not silver-stainable. The invention is further based on the discovery that polyclonal antiserum induced by OMP106 polypeptide isolated from a hemagglutinating M. catarrhalis strain has cytotoxic activity against a different hemagglutinating M. catarrhalis strain but not against a non-hemagglutinating M. catarrhalis strain.

3.1. Definitions and Abbreviations anti-OMP106=anti-OMP106 polypeptide antibody or antiserum ATCC®=American Type Culture Collection blebs=naturally occurring outer membrane vesicles of M. catarrhalis $Gb_4$=GalNAcβ1-3Galα1-4Galβ1-4Glc1-1Ceramide HA=hemagglutinating immuno-reactive=capable of provoking a cellular or humoral immune response kD=kilodaltons M. catarrhalis=Mc; Moraxella catarrhalis; Moraxella (Branhamella) catarrhalis; Branhamella catarrhalis; Neisseria catarrhalis; or Micrococcus catarrhalis NHA=non-hemagglutinating OG=n-octyl β-D-glucopyranoside or octyl glucoside OMP106=the outer membrane protein-106 polypeptide of Moraxella catarrhalis, having a molecular weight of about 180 kD to 230 kD by SDS-PAGE; extractable from blebs or intact cells of M. catarrhalis by OG or sarkosyl detergent OMP106-derived=fragment of the OMP106 polypeptide; polypeptide variant of wild-type OMP106 polypeptide or fragment thereof, containing one or more amino acid deletions, insertions or substitutions; or chimeric protein comprising a heterologous polypeptide fused to the C-terminal or N-terminal or internal segment of a whole or a portion of the OMP106 polypeptide OMP=outer membrane protein OMPs=outer membrane proteins PBS=phosphate buffered saline PAG=polyacrylamide gel polypeptide=a peptide of any length, preferably one having ten or more amino acid residues SDS=sodium dodecylsulfate SDS-PAGE=sodium dodecylsulfate polyacrylamide gel electrophoresis Nucleotide or nucleic acid sequences defined herein are represented by one-letter symbols for the bases as follows:

A (adenine)
C (cytosine)
G (guanine)
T (thymine)
U (uracil)
M (A or C)
R (A or G)
W (A or T/U)
S (C or G)
Y (C or T/U)
K (G or T/U)
V (A or C or G; not T/U)
H (A or C or T/U; not G)

D (A or G or T/U; not C)
B (C or G or T/U; not A)
N (A or C or G or T/U) or (unknown)

Peptide and polypeptide sequences defined herein are represented by one-letter symbols for amino acid residues as follows:
A (alanine)
R (arginine)
N (asparagine)
D (aspartic acid)
C (cysteine)
Q (glutamine)
E (glutamic acid)
G (glycine)
H (histidine)
I (isoleucine)
L (leucine)
K (lysine)
M (methionine)
F (phenylalanine)
P (proline)
S (serine)
T (threonine)
W (tryptophan)
Y (tyrosine)
V (valine)
X (unknown)

The present invention may be more fully understood by reference to the following detailed description of the invention, non-limiting examples of specific embodiments of the invention and the appended figures.

DETAILED DESCRIPTION OF THE FIGURES

FIG. 1: Denaturing PAGE comparison of outer membrane protein profiles of *M. catarrhalis* blebs or octyl glucoside (OG) extracts of whole *M. catarrhalis* cells. The numbers over the lanes refer to the ATCC® (American Type Culture Collection) strain designations. A prestained SDS-PAGE standard (BioRad catalog #161-0305) was used as molecular weight markers. The standard consisted of the following polypeptides with their approximate molecular weights noted in parenthesis: rabbit muscle phosphorylase B (106 kD); bovine serum albumin (80 kD); hen egg white ovalbumin (49.5 kD); bovine carbonic anhydrase (32.5 kD); soybean trypsin inhibitor (27.5 kD); hen egg white lysozyme (18.5 kD). The positions of the molecular weight markers in the gel are noted on the left side of the drawing by arrows with the molecular weights (kD) of some of the markers above the arrows.

Figure 2:

FIG. 2: Results from overlaying thin layer chromatograms of glycolipids with $^{125}$I-labeled outer membrane blebs. In Panels A C, Lane 1 contains glycolipid standards indicated on the left; Lane 2 contains asialo-GM$_1$; Lane 3 contains Gb$_3$, Gb$_4$, and Forssman antigen; and Lane 4 contains a Folch extraction of human erythrocytes. The chromatogram shown in Panel A is stained with orcinol, the chromatogram shown in Panel B is overlayed with $^{125}$I-labeled blebs of ATCC® (American Type Culture Collection)strain 8176 (a non-hemagglutinating strain), and the chromatogram shown in Panel C is overlayed with $^{125}$I-labeled blebs of ATCC® (American Type Culture Collection) strain 49143 (a hemagglutinating strain). Only the hemagglutinating strain bound to the Gb$_4$ glycolipid band in the third and fourth lanes.

Figure 3:
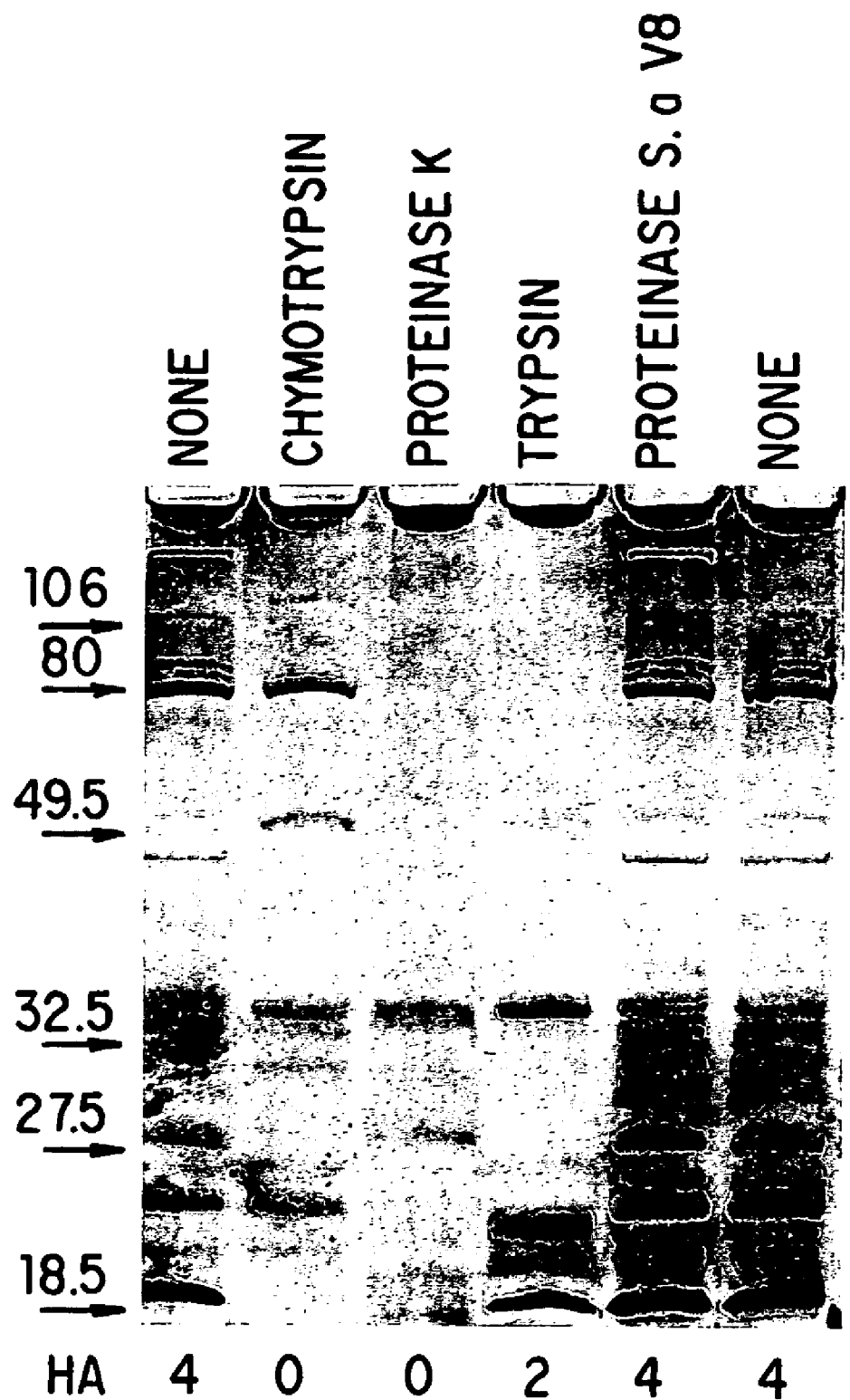

FIG. 3: Protein profiles by silver staining of octyl glucoside extracts of outer membrane proteins following digestion of the *M. catarrhalis* cells with the proteases indicated in the figure. The hemagglutination activity of the cells following the digestion is indicated below the figure in the row labeled HA. The molecular weight markers used are as per FIG. 1.

Figure 4:
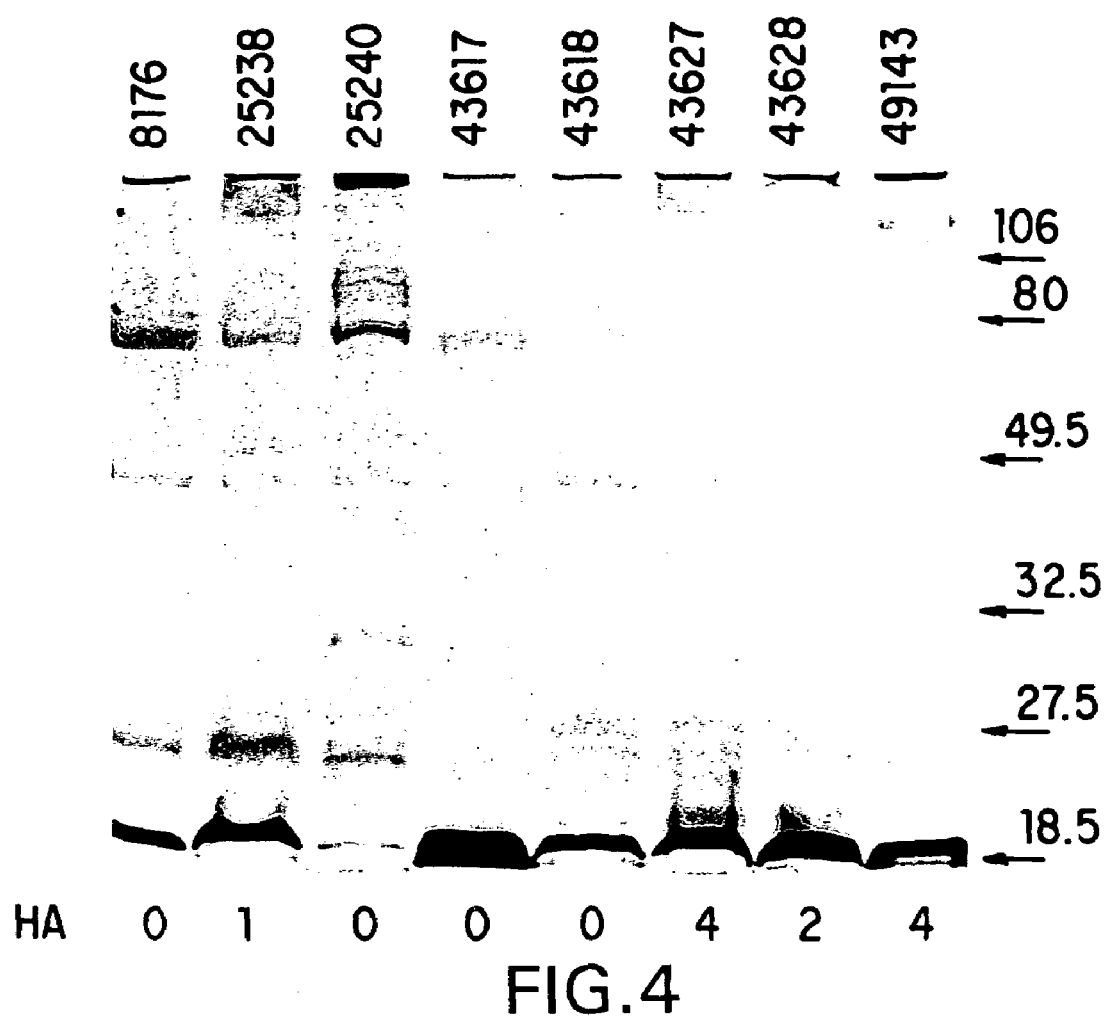

FIG. 4: Comparison of protein profiles by silver staining of outer membrane proteins from various ATCC® (American Type Culture Collection) strains of *M. catarrhalis*. The strain designations are indicated above the lanes. The hemagglutination activity of the strains are indicated in the row labeled HA below the figure. Note a protein having an apparent molecular weight greater than that of rabbit muscle phosphorylase B (106 kD) is common to the hemagglutinating strains, but is absent in the non-hemagglutinating strains. This polypeptide is designated OMP106. The molecular weight markers used are as per FIG. 1.

Figure 5:
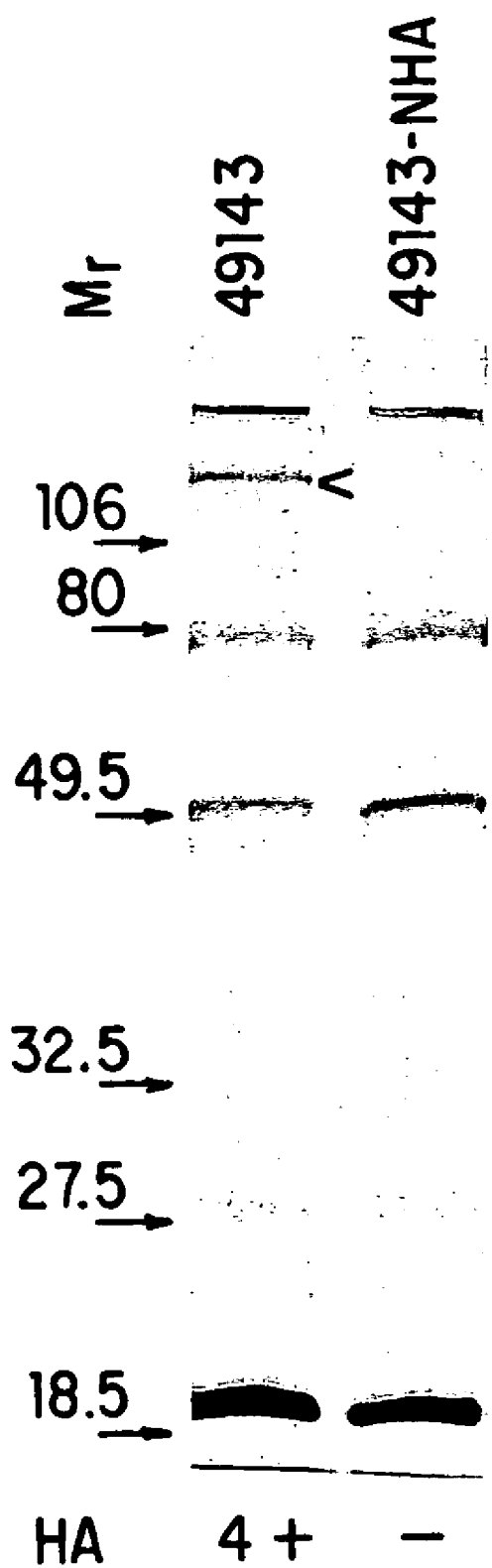

FIG. 5: Comparison of protein profiles by silver staining of outer membrane proteins from two *M. catarrhalis* ATCC® (American Type Culture Collection) 49143 cultivars: 49143 (hemagglutinating cultivar) and 49143-NHA (non-hemagglutinating cultivar). The hemagglutination activities of the cultivars are indicated below the figure in the row labeled HA. Note the absence of the OMP106 polypeptide band (indicated by <) in the non-hemagglutinating cultivar. The molecular weight markers used are as per FIG. 1.

Figure 6:
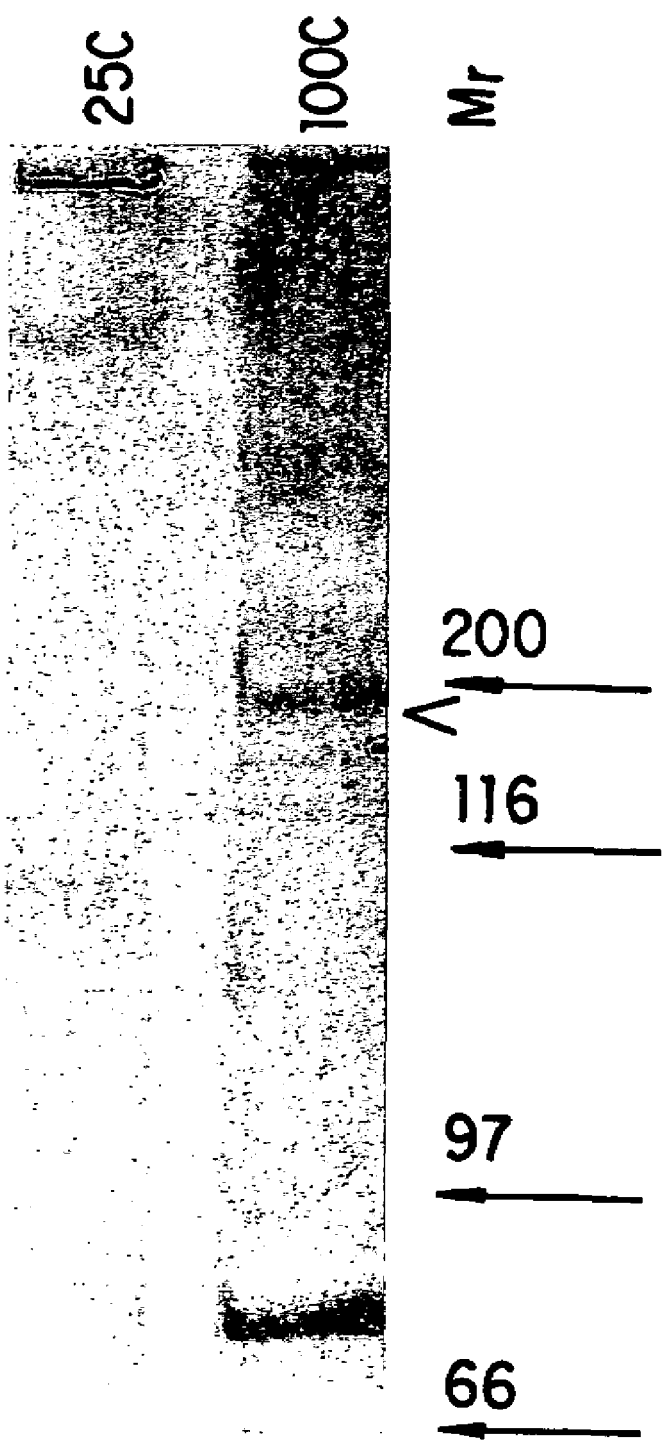

FIG. 6: Molecular weight estimation of OMP106 in a 6% denaturing polyacrylamide gel using OG extracts of ATCC® (American Type Culture Collection) strain 49143 that were incubated in sample buffer at either 25° C. or 100° C. prior to application to the gel. Proteins in the gel were visualized by reductive silver staining. Note that the OMP106 polypeptide band (indicated by the <) is seen only in the sample incubated at 100° C. A broad range SDS-PAGE standard (BioRad catalog #161-0317) was used as molecular weight markers. The standard consisted of the following polypeptides (approximate molecular weights noted in parenthesis): rabbit skeletal muscle myosin (200 kD); *E. coli* β-galactosidase (116 kD); rabbit muscle phosphorylase B (97.4 kD); bovine serum albumin (66.2 kD). The positions of the molecular weight markers in the gel are noted on the right side of the figure by arrows with the molecular weights (kD) of the markers above the arrows.

Figure 7:
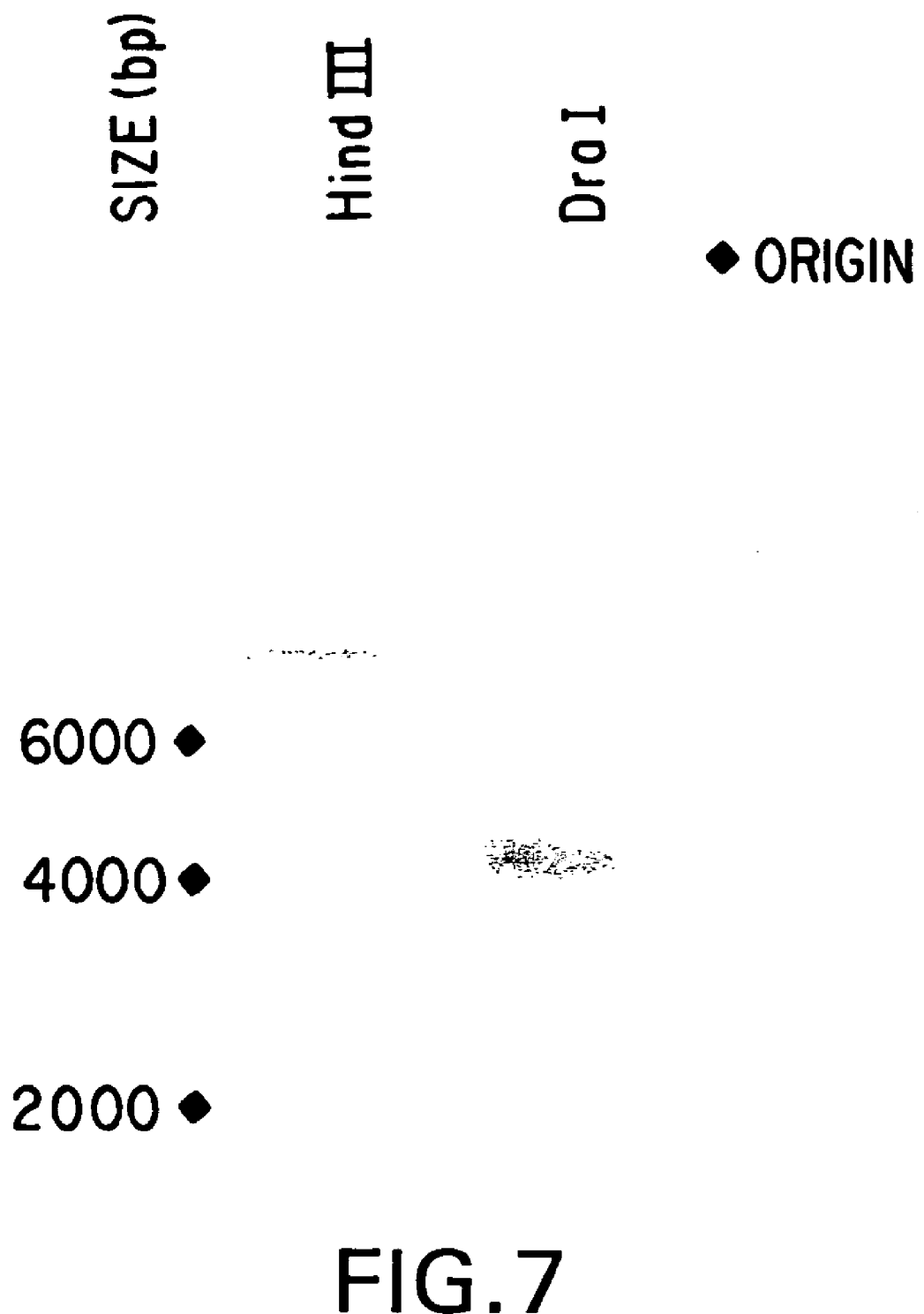

FIG. 7: Southern blot analysis of DraI and HindIII restriction endonuclease digests of *M. catarrhalis* chromosomal DNA probed with Mc5-72. DNA of *M. catarrhalis* strain 49143 was digested with DraI or HindIII. Southern analysis of the digested DNA was carried out using Mc5-72 (SEQ ID NO:4) as the probe. The high stringency wash was 2×SSC, 1% SDS at 50° C. for about 20 to about 30 minutes. Lane 1 contains HindIII digest; the hybridizing band has an approximate size of 8.0 kb. Lane 2 contains DraI digest: the hybridizing band has an approximate size of 4.2 kb.

Figure 8A:
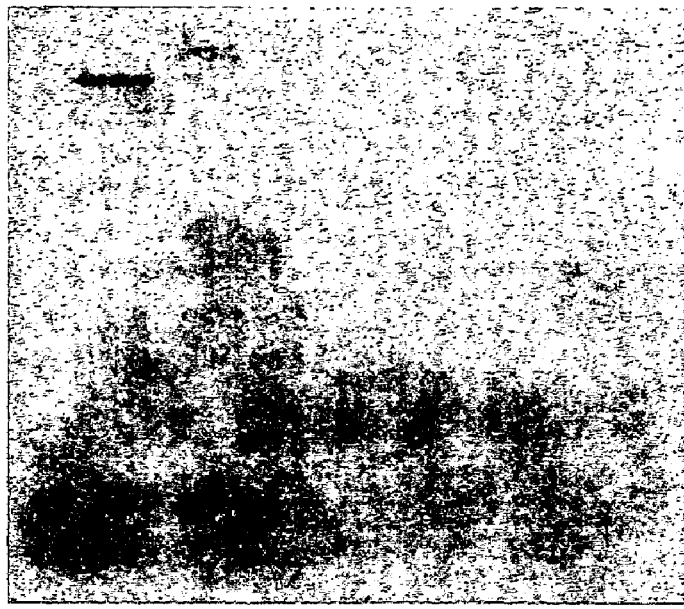
Figure 8B:
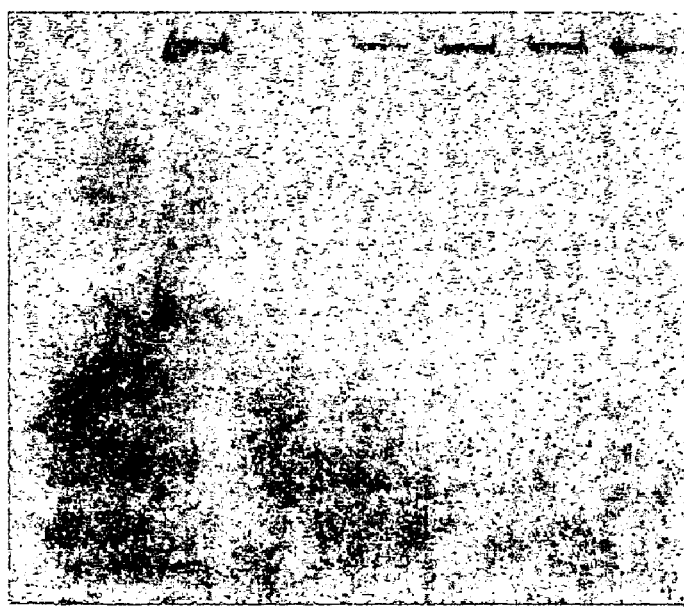

FIGS. 8A and 8B: Western Blots of protein extracts of *M. catarrhalis* and related species using a rabbit antiserum to OMP106 as the probe (FIG. 8A), compared to the reactivity of the serum prior to immunization of the rabbit with OMP106 (FIG. 8B). Samples in the lanes of FIGS. 8A and 8B are as follows: Lane A, *M. catarrhalis;* Lane B, *Moraxella ovis;* Lane C, *Moraxella lacunata;* Lane D, *Moraxella osloensis;* Lane E, *Moraxella bovis;* Lane F, *Neisseria meningitidis;* Lane G, *Neisseria gonorrhoeae.* The molecular weight markers used are as per FIG. 1.

Figure 9A:
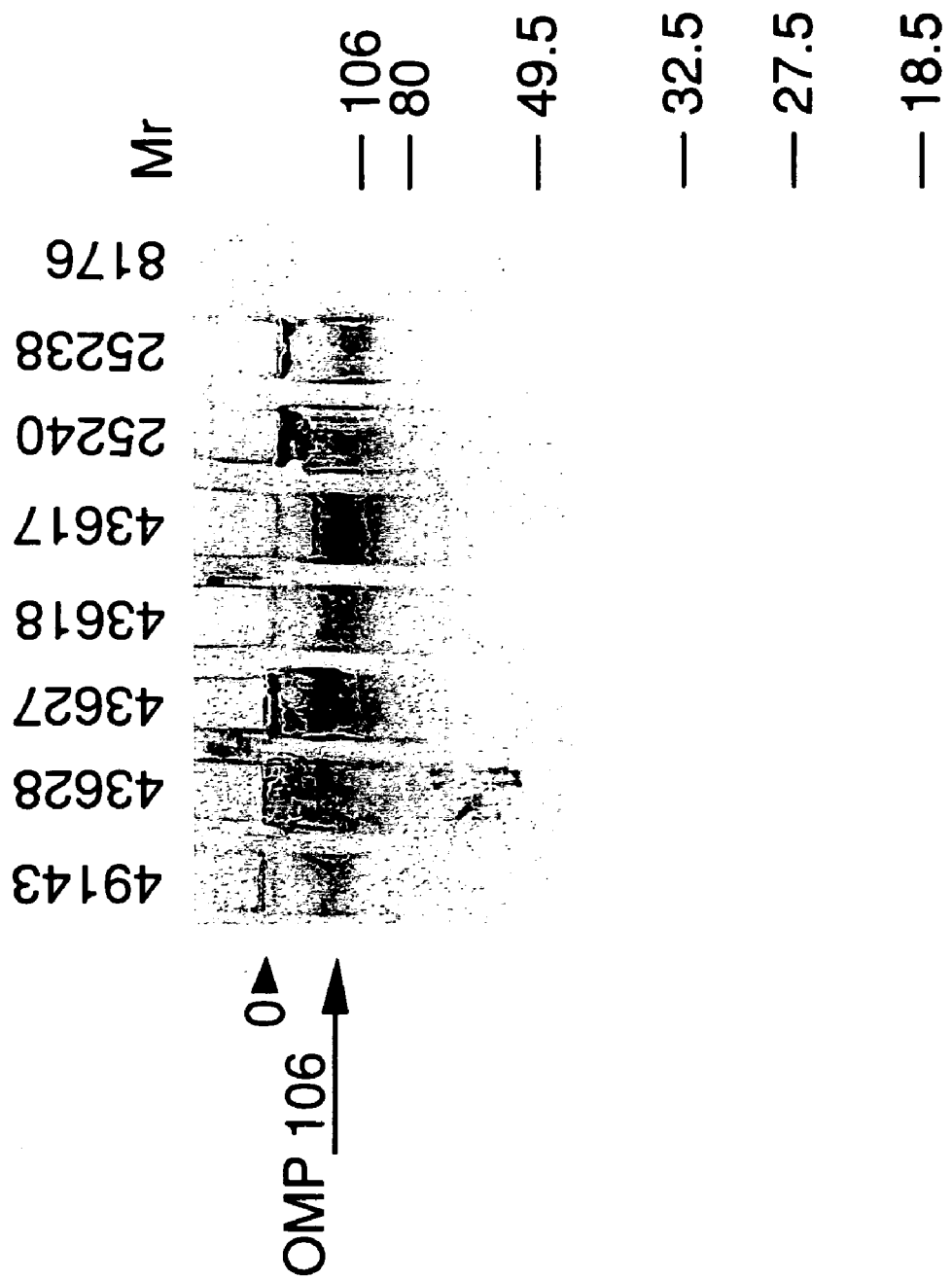
Figure 9B:
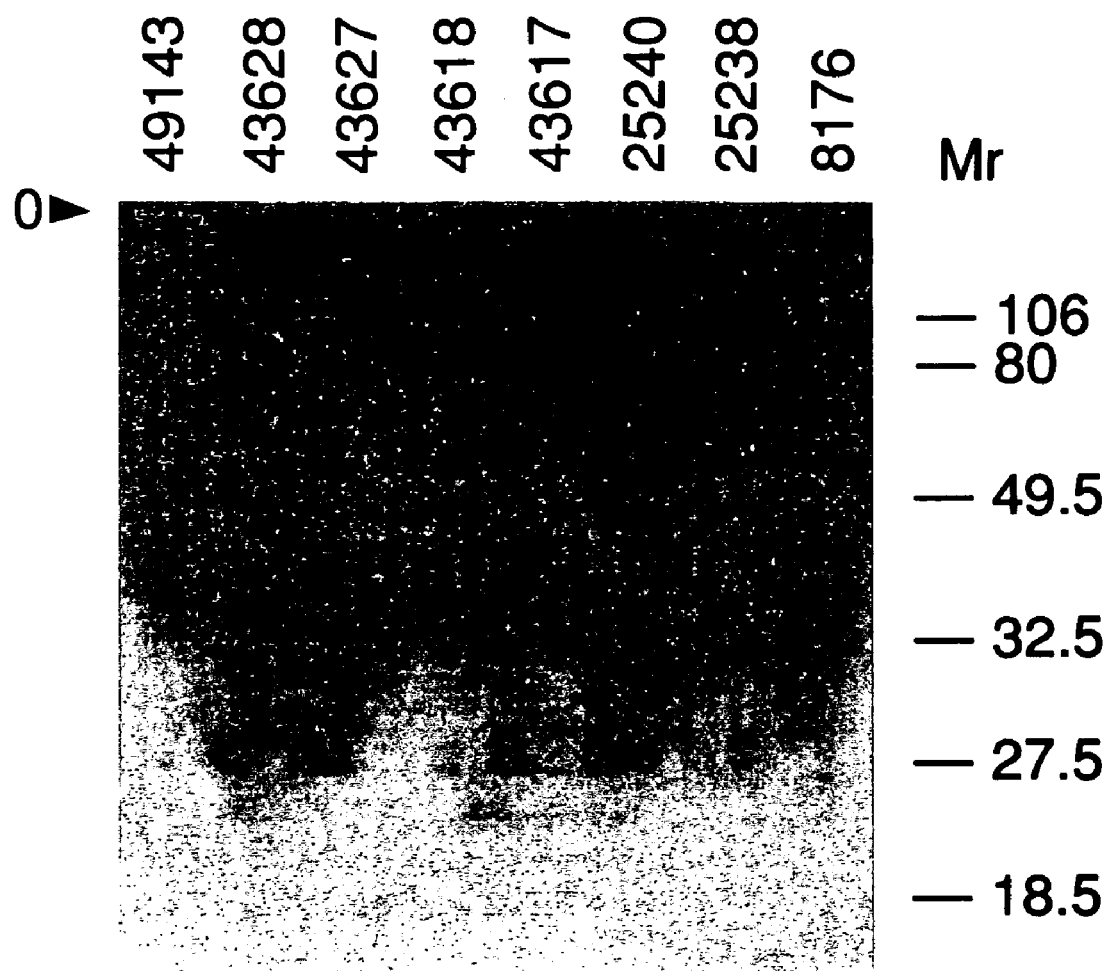

FIG. 9A: Western blot demonstrating that a rabbit antiserum to the OMP106 plypeptide from *M. catarrhalis* ATCC® (American Type Culture Collection) 49143 cross-reacts with a polypeptide of a similar molecular weight in a number of HA and NHA strains of *M. catarrhalis* (the location of the OMP106 polypeptide is indicated by the arrow). The Western examined octyl glucoside extracts of various *M. catarrhalis* strains. The ATCC® (American Type Culture Collection) accession numbers of the strains are indicated at the top of the lanes. The transfer and Western blot procedures used were identical to those used to obtain the blots shown in FIG. 8.

FIG. 9B: Western blot of the same extracts as those in FIG. 9A using the pre-immune serum corresponding to that used in FIG. 9A.

FIG. 10: Western blot using a monoclonal antibody to OMP106 polypeptide SRB #1 to probe proteins resolved on a 4 to 20% SDS-polyacrylamide gel. OMP106 must be heated to 100° C. before it will resolve at 190 kD on a gel. The samples are as follows: (1) molecular weight standards; (2) detergent extract containing outer membrane proteins of *M. catarrhalis* that were heated to 100° C.; (3) purified OMP106 heated to 100° C.; (4) detergent extract containing outer membrane proteins of *M. catarrhalis* that were incubated at room temperature; and (5) purified OMP106 incubated at room temperature.

FIG. 11: organization of the OMP106 locus and fragments that were subcloned. 72 refers to the approximate location of the 72 bp DNA fragment. Plasmid p omp N/P refers to a omp106 DNA fragment obtained by digestion with NotI/PstI and subcloned into pBluescriptII SK. A ClaI/PstI restriction fragment was obtained from p omp N/P and subcloned into pBluescriptII SK to yield the plasmid p omp C/P. A PCR product having an approximate size of 3.5 kb was generated using genomic DNA or phageλ omp106.6 DNA as a template, digested with PstI and EcoRI and cloned into PstI/EcoRI digested pBluescriptII SK to yield the plasmid p omp P/R. Physical mapping of the pBK omp R/H located a unique XbaI site approximately 1.5 kb upstream from the HindIII site. Sequences between this XbaI site and XbaI in the polylinker were deleted and the recircularized phagemid was designated as pBK omp R/X. Plasmid p omp 106× containing the entire open reading frame of OMP106 was constructed from pBK omp R/X, p omp C/P, and p omp P/R; see Section 9 for details.

FIGS. 12A and 12B: Map of OMP106 and OMP106 deletion mutants. The organization of the omp 106 locus in the wild-type strain (FIG. 12A) compared to the structure imposed on the locus after the gene-targeting construct has been inserted by homologous recombination (FIG. 12B) is shown. Probe 1 and probe 2 designate DNA fragments used for Southern analysis. 72 refers to the approximate location of the 72 bp fragment described in the text. Thin lines under the construct indicate the length of DNA fragments generated by cutting DNA from wild-type and knockout strains with ClaI or ClaI/EcoRI.

5. DETAILED DESCRIPTION OF THE INVENTION

5.1 Hemagglutinating and Non-Hemagglutinating Cultivars

The invention provides an isolated or a substantially pure OMP106 polypeptide of *M. catarrhalis.* The OMP106 polypeptide comprises the whole or a subunit of a protein embedded in or located on the outer surface of the outer membrane of hemagglutinating (HA) strains and many non-hemagglutinating (NHA) strains and cultivars of *M. catarrhalis.* OMP106 contributes directly or indirectly to the hemagglutination phenotype of the HA strains and cultivars. According to the invention, HA *M. catarrhalis* cells agglutinate human or rabbit erythrocytes in any standard hemagglutination assay, such as the one taught by Soto-Hernandez et al. 1989, J. Clin. Microbiol. 27:903-908. Although not intending to be limited to any particular mechanism of action, it is presently envisaged that *M. catarrhalis* agglutinates erythrocytes by binding to the globotetrose ($Gb_4$) moiety of glycolipid and glycoprotein receptors on the host cell surfaces and that the hemagglutination activity is mediated in part by appropriately modified OMP106 polypeptide, which has the particular property of being susceptible to silver staining. By contrast, unmodified or inappropriately modified OMP106 polypeptide is neither active in mediating hemagglutination nor silver-stainable. Moreover, OMP106 polypeptide is the only polypeptide having an apparent molecular weight of about 180 kD to about 230 kD in SDS-PAGE that is OG- or sarkosyl-extractable from HA or NHA *M. catarrhalis* blebs or intact cells.

The hemagglutination activity of HA *M. catarrhalis* cells is inhibited by globotetrose (GalNAcβ1-3Galα1-4Galβ1-4Glcβ1; $Gb_4$) and the monosaccharides that comprise Gb4, including N-acetyl-D-galactosamine, D-galactose and glucose, and derivatives thereof, such as methyl-α-galactose or methyl-β-galactose. The hemagglutination activity of HA *M. catarrhalis* cells is also inhibited by relatively higher concentrations of a number of other sugars including but not limited to D-mannose, L-fucose, D-glucose, and N-acetyl-D-glucosamine.

The hemagglutination activity and the OMP106 polypeptide of intact HA M catarrhalis cells are both reduced or destroyed by digestion of intact *M. catarrhalis* cells by various proteases including, but not limited to, LCK (Nα-ptosyl-L-lysine chloro methyl ketone [also known as 1-chloro-3-tosylamino-7-amino-L-2-heptanone])-treated chymotrypsin, proteinase K and TPCK (N-tosyl-L-phenylalanine chloromethyl ketone)-treated trypsin. Protease V8 digestion of intact HA *M. catarrhalis* cells, however, affects neither the hemagglutination activity nor the physical integrity of the OMP106 polypeptide of such cells.

A non-hemagglutinating (NHA) cultivar may be derived from a HA *M. catarrhalis* strain or cultivar by serial passage in static liquid cultures (i.e., liquid cultures maintained at 35° C. without shaking). For example, a HA *M. catarrhalis* strain or cultivar is grown in Mueller Hinton broth and every five days an inoculum is taken from the surface of the static culture to inoculate a subsequent static culture. The preferred inoculum is any floating mat of cells at the surface of the culture. Passaging in static cultures is maintained until a NHA cultivar is produced. A NHA cultivar of the invention may be used to produce protective vaccines, such as whole cell vaccines, against *M. catarrhalis* infections.

By contrast, the hemagglutinating phenotype of a HA *M. catarrhalis* strain or cultivar can be maintained by passaging the strain or cultivar in shaking liquid cultures. In an embodiment, a HA *M. catarrhalis* strain or cultivar is grown in Mueller Hinton broth at 35 to 37° C. with shaking at about 200 RPM and passaged every 24 to 48 hours. The hemagglutinating phenotype of a HA *M. catarrhalis* strain or cultivar also can be maintained by passaging on solid media. For example, a HA *M. catarrhalis* strain or cultivar is grown on a plate containing blood agar or Mueller Hinton agar.

5.2. Omp106 Polypeptide

OMP106 polypeptide of the invention is the sole outer membrane protein of a HA *M. catarrhalis* strain or cultivar that has an apparent molecular weight in SDS-PAGE of about 180 kD to about 230 kD, preferably about 190 kD. According to the invention, an outer membrane protein of *M. catarrhalis* is a polypeptide that is present in *M. catarrhalis* blebs, or that can be extracted from *M. catarrhalis* blebs or intact cells by n-octyl β-D-glucopyranoside (OG) or sarkosyl detergent in buffer solution at room temperature. See Murphy and Loeb, 1989, Microbial Pathogenesis 6:159 174, for a discussion of *M. catarrhalis* blebs, which are naturally occurring vesicles consisting of the outer membrane of *M. catarrhalis*. NHA *M. catarrhalis* strains or cultivars either do not have OMP106 polypeptide, or have OMP106 polypeptide in a form that binds anti-OMP106 antibodies (see Section 5.5., infra) but does not react with silver stain (i.e., using Silver Stain Plus of BioRad [Richmond, Calif.], or the procedure described by Gottlieb and Chauko, 1987, Anal. Biochem. 165:33). By contrast, OMP106 polypeptide from HA *M. catarrhalis* strains or cultivars binds anti-OMP106 antibodies, and reacts with silver stain.

OMP106 polypeptide may be identified in HA *M. catarrhalis* blebs or intact cells by its susceptibility to degradation by protease treatment that also abolishes or attenuates the hemagglutination activity of the same HA strain (See Section 5.1. above for examples of proteases that do or do not destroy hemagglutination activity of intact *M. catarrhalis* cells). In other words, digestion with a protease that destroys or reduces the hemagglutination activity of a HA strain or cultivar will also change, in SDS-PAGE, the abundance or the location of OMP106 polypeptide isolated from the strain or cultivar after such a digestion as compared to that isolated from the same strain or cultivar before the digestion.

OMP106 polypeptide may also be identified as the polypeptide in OG or sarkosyl extract of *M. catarrhalis* blebs or intact cells that has an apparent molecular weight of greater than 106 kD as determined by denaturing gel electrophoresis in 12% PAG with SDS, using formulations as described in Harlow and Lane (Antibodies: A Laboratory Manual, Cold Spring Harbor Laboratory Press, Cold Spring Harbor, N.Y., Appendix I, 1988). Heat treatment of the OG or sarkosyl extract at 100° C. for 5 minutes can cause the OMP106 polypeptide to have an apparent molecular weight of about 180 kD to about 230 kD as determined by SDS-PAGE in 6% PAG without any reducing agents, using formulations as described in Harlow and Lane, id. In a particular embodiment, OMP106 polypeptide in the heat-treated OG or sarkosyl extract of *M. catarrhalis* strain ATCC® (American Type Culture Collection) 49143 has an apparent molecular weight of about 190 kD.

In particular embodiments, the OMP106 polypeptide is that prepared from any of *M. catarrhalis* strains including, but not limited to, ATCC® (American Type Culture Collection) 49143, ATCC® (American Type Culture Collection) 25238, ATCC® (American Type Culture Collection) 25240, ATCC® (American Type Culture Collection) 43617, ATCC® (American Type Culture Collection) 43618, ATCC® (American Type Culture Collection) 43627 and ATCC® (American Type Culture Collection) 43628. The preferred source of OMP106 polypeptide is a HA cultivar of such strains. The more preferred source is a HA cultivar of ATCC® (American Type Culture Collection) 49143.

In a particular embodiment, OMP106 polypeptide comprises, preferably at the amino-terminal, the amino acid sequence IGISEADGGKGGANARGDKSIAIGDIAQALGSQSIAIGDNKIV (SEQ ID NO:1) or a sequence substantially homologous thereto. The OMP106 polypeptide may additionally comprise, carboxyl-distal to the above mentioned sequence, an octapeptide having the amino acid sequence GTVLGGKK (SEQ ID NO:2) or a sequence substantially homologous thereto. As used herein a substantially homologous amino acid sequence is at least 80%, preferably 100%, identical to the referenced amino acid sequence (see e.g. SEQ ID NO:11).

According to various aspects of the invention, the polypeptides of the invention are characterized by their apparent molecular weights based on the polypeptides' migration in SDS-PAGE relative to the migration of known molecular weight markers. While any molecular weight standards known in the art may be used with the SDS-PAGE, preferred molecular weight markers comprise at least rabbit skeletal muscle myosin, *E. coli* β-galactosidase and rabbit muscle phosphorylase B. One skilled in the art will appreciate that the polypeptides of the invention may migrate differently in different types of gel systems (e.g., different buffers; different concentration of gel, crosslinker or SDS). One skilled in the art will also appreciate that the polypeptides may have different apparent molecular weights due to different molecular weight markers used with the SDS-PAGE. Hence, the molecular weight characterization of the polypeptides of the invention is intended to be directed to cover the same polypeptides on any SDS-PAGE systems and with any molecular weight markers which might indicate sightly different apparent molecular weights for the polypeptides than those disclosed here.

5.3. OMP106-Derived Polypeptides

An OMP106-derived polypeptide of the invention may be a fragment of the OMP106 polypeptide. The intact OMP106 polypeptide may contain one or more amino acid residues that are not necessary to its immunogenicity. It may be the case, for example, that only the amino acid residues forming a particular epitope of the OMP106 polypeptide is necessary for immunogenic activity. Unnecessary amino acid sequences can be removed by techniques well-known in the art. For example, the unwanted amino acid sequences can be removed by limited proteolytic digestion using enzymes such as trypsin, papain, or related proteolytic enzymes or by chemical cleavage using agents such as cyanogen bromide and followed by fractionation of the digestion or cleavage products.

An OMP106-derived polypeptide of the invention may also be a modified OMP106 polypeptide or fragment thereof (i.e., an OMP106 polypeptide or fragment having one or more amino acid substitutions, insertions and/or deletions of the wild-type OMP106 sequence). Such modifications may enhance the immunogenicity of the resultant polypeptide product or have no effect on such activity. Modification techniques that may be used include those disclosed in U.S. Pat. No. 4,526,716.

An OMP106-derived polypeptide may further be a chimeric polypeptide comprising one or more heterologous polypeptides fused to the amino-terminal or carboxyl-terminal or internal of a complete OMP106 polypeptide or a portion of or a fragment thereof. Useful heterologous polypeptides comprising such chimeric polypeptide include, but are not limited to, a) pre- and/or pro-sequences that facilitate the transport, translocation and/or processing of the OMP106-derived polypeptide in a host cell, b) affinity purification sequences, and c) any useful immunogenic sequences (e.g., sequences encoding one or more epitopes of a surface-exposed protein of a microbial pathogen).

Preferably, the OMP106-derived polypeptides of the invention are immunologically cross-reactive with the OMP106 polypeptide, thus being capable of eliciting in an animal an immune response to *M. catarrhalis*. More preferably, the OMP106-derived polypeptides of the invention comprise sequences forming one or more outer-surface epitopes of the native OMP106 polypeptide of *M. catarrhalis* (i.e., the surface-exposed epitopes of OMP106 polypeptide as it exists in intact *M. catarrhalis* cells). Such preferred OMP106-derived polypeptides can be identified by their ability to specifically bind antibodies raised to intact *M. catarrhalis* cells (e.g., antibodies elicited by formaldehyde or glutaldehyde fixed *M. catarrhalis* cells; such antibodies are referred to herein as "anti-whole cell" antibodies). For example, polypeptides or peptides from a limited or complete protease digestion of the OMP106 polypeptide are fractionated using standard methods and tested for their ability to bind anti-whole cell antibodies. Reactive polypeptides comprise preferred OMP 106-derived polypeptides. They are isolated and their amino acid sequences determined by methods known in the art.

Also preferably, the OMPI06-derived polypeptides of the invention comprise sequences that form one or more epitopes of native OMP106 polypeptide that mediate hemagglutination by HA *M. catarrhalis* cells. Such preferred OMP106-derived polypeptides may be identified by their ability to interfere with hemagglutination by HA *M. catarrhalis* cells. For example, polypeptides from a limited or complete protease digestion or chemical cleavage of OMP106 polypeptide are fractionated using standard methods and tested for the ability to interfere in hemagglutination by *M. catarrhalis* cells. Once identified and isolated the amino acid sequences of such preferred OMP106-derived polypeptides are determined using standard sequencing methods. The determined sequence may be used to enable production of such polypeptides by synthetic chemical and/or genetic-engineering means.

These preferred OMP106-derived polypeptides also can be identified by using anti-whole cell antibodies to screen bacterial libraries expressing random fragments of *M. catarrhalis* genomic DNA or cloned nucleotide sequences encoding the OMP106 polypeptide. See, e.g., Sambrook et al., Molecular Cloning, A Laboratory Manual, 2nd ed., Cold Spring Harbor Press, N.Y., Vol. 1, Chapter 12. The reactive clones are identified and their inserts are isolated and sequenced to determine the amino acid sequences of such preferred OMP106-derived polypeptides.

5.4. Isolation and Purification Of OMP106 Polypeptide and OMP106-Derived Polypeptides The invention provides isolated OMP106 polypeptides and OMP106-derived polypeptides. As used herein, the term "isolated" means that the product is significantly free of other biological materials with which it is naturally associated. That is, for example, an isolated OMP106 polypeptide composition is between about 70% and 94% pure OMP106 polypeptide by weight. Preferably, the OMP106 polypeptides and OMP106-derived polypeptides of the invention are purified. As used herein, the term "purified" means that the product is substantially free of other biological material with which it is naturally associated. That is comprising a purified OMP106 polypeptide composition is at least 95% pure OMP106 polypeptide by weight, preferably at least 98% pure OMP106 polypeptide by weight, and most preferably at least 99% pure OMP106 polypeptide by weight.

The OMP106 polypeptide of the invention may be isolated from protein extracts including whole cell extract, of any *M. catarrhalis* strain or cultivar. Preferably, the protein extract is an octyl glucoside or sarkosyl extract of outer membrane vesicles (i.e., blebs) or whole cells of *M. catarrhalis* including, but not limited to, any of strains ATCC® (American Type Culture Collection) 49143, ATCC® (American Type Culture Collection) 25238, ATCC® (American Type Culture Collection) 25240, ATCC® (American Type Culture Collection) 43617, ATCC® (American Type Culture Collection) 43618, ATCC® (American Type Culture Collection) 43627 and ATCC® (American Type Culture Collection) 43628. The preferred source of such extracts is a HA cultivar of such strains. The more preferred source of such extracts is a HA cultivar of ATCC® (American Type Culture Collection) 49143. Another source of the OMP106 polypeptide is protein preparations from gene expression systems expressing cloned sequences encoding OMP106 polypeptide or OMP106-derived polypeptides (see Section 5.8., infra).

The OMP106 polypeptide can be isolated and purified from the source material using any biochemical technique and approach well known to those skilled in the art. In one approach, *M. catarrhalis* outer membrane is obtained by standard techniques and outer membrane proteins are solubilized using a solubilizing compound such as a detergent. A preferred solubilizing solution is one containing about 1.25% octyl glucopyranoside w/v (OG). Another preferred solubilizing solution is one containing about 1.25% sarkosyl. OMP106 polypeptide is in the solubilized fraction. Cellular debris and insoluble material in the extract are separated and removed preferably by centrifuging. The polypeptides in the extract are concentrated, incubated in SDS-containing Laemmli gel sample buffer at 100° C. for 5 minutes and then fractionated by electrophoresis in a 6% denaturing sodium dodecylsulfate (SDS) polyacrylamide gel (PAG) without reducing agent. See Laemmli, 1970, Nature 227:680-685. The band or fraction identified as OMP106 polypeptide as described above (e.g., the silver-stained polypeptide band that is present in the OG or sarkosyl extract of a HA but not that of a corresponding NHA cultivar or that of the HA cultivar after digestion with a protease that abolishes hemagglutination activity) may then be isolated directly from the fraction or gel slice containing the OMP106 polypeptide. In a preferred embodiment, OMP106 polypeptide has an apparent molecular weight of 190 kD as determined by comparing its migration distance or rate in a denaturing SDS-PAGE relative to those of rabbit skeletal muscle myosin (200 kD) and *E. coli* β-galactosidase (116 kD).

Another method of purifying OMP106 polypeptide is by affinity chromatography using anti-OMP106 antibodies, (see Section 5.5). Preferably, monoclonal anti-OMP106 antibodies are used. The antibodies are covalently linked to agarose gels activated by cyanogen bromide or succinamide esters (Affi-Gel, BioRad, Inc.) or by other methods known to those skilled in the art. The protein extract is loaded on the top of the gel as described above. The contact is for a period of time and under standard reaction conditions sufficient for OMP106 polypeptide to bind to the antibody. Preferably, the solid support is a material used in a chromatographic column. OMP106 polypeptide is then removed from the antibody, thereby permitting the recovery OMP106 polypeptide in isolated, or preferably, purified form.

An OMP106-derived polypeptide of the invention can be produced by chemical and/or enzymatic cleavage or degradation of isolated or purified OMP106 polypeptide. An OMP106-derived polypeptide can also be chemically synthesized based on the known amino acid sequence of OMP106 polypeptide and, in the case of a chimeric polypeptide, those of the heterologous polypeptide by methods well-known in the art. See, for example, Creighton, 1983, Proteins: Structures and Molecular Principles, W. H. Freeman and Co., NY.

An OMP106-derived polypeptide can also be produced in a gene expression system expressing a recombinant nucleotide construct comprising sequences encoding OMP106-derived polypeptides. The nucleotide sequences encoding polypeptides of the invention may be synthesized, and/or cloned, and expressed according to techniques well known to those skilled in the art. See, for example, Sambrook, et al., 1989, Molecular Cloning, A Laboratory Manual, Vols. 1 3, Cold Spring Harbor Press, NY, Chapter 9.

OMP106-derived polypeptides of the invention can be fractionated and purified by the application of standard protein purification techniques, modified and applied in accordance with the discoveries and teachings described herein. In particular, preferred OMP106-polypeptides of the invention, those that form an outer-surface epitope of the native OMP106 polypeptide may be isolated and purified according to the affinity procedures disclosed above for the isolation and purification of OMP106 polypeptide (e.g., affinity purification using anti-OMP106 antibodies.

If desirable, the polypeptides of the invention may be further purified using standard protein or peptide purification techniques including but are not limited to electrophoresis, centrifugation, gel filtration, precipitation, dialysis, chromatography (including ion exchange chromatography, affinity chromatography, immunoadsorbent affinity chromatography, reverse-phase high performance liquid chromatography, and gel permeation high performance liquid chromatography), isoelectric focusing, and variations and combinations thereof.

One or more of these techniques may be employed sequentially in a procedure designed to separate molecules according to their physical or chemical characteristics. These characteristics include the hydrophobicity, charge, binding capability, and molecular weight of the protein. The various fractions of materials obtained after each technique are tested for their abilities to bind the OMP106 receptor or ligand, to bind anti-OMP106 antibodies or to interfere with hemagglutination by HA *M. catarrhalis* cells ("test" activities). Those fractions showing such activity are then subjected to the next technique in the sequential procedure, and the new fractions are tested again. The process is repeated until only one fraction having the above described "test" activities remains and that fraction produces only a single band or entity when subjected to polyacrylamide gel electrophoresis or chromatography.

5.5. OMP106 Immunogens and Anti-OMP106 Antibodies

The present invention provides antibodies that specifically bind OMP106 polypeptide or OMP106-derived polypeptides. For the production of such antibodies, isolated or preferably, purified preparations of OMP106 polypeptide or OMP106-derived polypeptides are used as immunogens.

In an embodiment, the OMP106 polypeptide is separated from other outer membrane proteins present in the OG or sarksyl extract of outer membrane of HA *M. catarrhalis* cells or blebs using SDS-PAGE (see Section 5.2. above) and the gel slice containing OMP106 polypeptide is used as the immunogen and injected into a rabbit to produce antisera containing polyclonal OMP106 antibodies. The same immunogen can be used to immunize mice for the production of hybridoma lines that produce monoclonal anti-OMP106 antibodies. In particular embodiments, a PAG slice containing isolated or purified OMP106 from any of strains ATCC® (American Type Culture Collection) 49143, ATCC® (American Type Culture Collection) 25238, ATCC® (American Type Culture Collection) 25240, ATCC® (American Type Culture Collection) 43617, ATCC® (American Type Culture Collection) 43618, ATCC® (American Type Culture Collection) 43627 and ATCC® (American Type Culture Collection) 43628 is used as the immunogen. In preferred embodiments, a PAG slice containing isolated or purified OMP106 from a HA cultivar of such strains is used. In a more preferred embodiment, a PAG slice containing isolated or purified OMP106 from a HA cultivar of strain ATCC® (American Type Culture Collection) 49143 is used as the immunogen.

In other embodiments, peptide fragments of OMP106 polypeptide are used as immunogens. Preferably, peptide fragments of purified OMP106 polypeptide are used. The peptides may be produced by protease digestion, chemical cleavage of isolated or purified OMP106 polypeptide or chemical synthesis and then may be isolated or purified. Such isolated or purified peptides can be used directly as immunogens. In particular embodiments, useful peptide fragments include but are not limited to those having the sequence IGISEADGGKGGANARGDKSIAIGDI-AQALGSQSIAIGDNKIV (SEQ ID NO:1) or any portion thereof that is 6 or more amino acids in length. In an another embodiment, the peptide fragment has the sequence GTV-LGGKK (SEQ ID NO:2).

Useful immunogens may also comprise such peptides or peptide fragments conjugated to a carrier molecule, preferably a carrier protein. Carrier proteins may be any commonly used in immunology, include, but are not limited to, bovine serum albumin (BSA), chicken albumin, keyhole limpet hemocyanin (KLH) and the like. For a discussion of hapten protein conjugates, see, for example, Hartlow, et al., Antibodies: A Laboratory Manual, Cold Spring Harbor Laboratory Press, Cold Spring Harbor, N.Y., 1988, or a standard immunology textbook such as Roitt, I. et al., IMMUNOLOGY, C. V. Mosby Co., St. Louis, Mo. (1985) or Klein, J., IMMUNOLOGY, Blackwell Scientific Publications, Inc., Cambridge, Mass., (1990).

In yet another embodiment, for the production of antibodies that specifically bind one or more outer-surface epitopes of the native OMP106 polypeptide, intact HA *M. catarrhalis* cells or blebs prepared therefrom are used as immunogen. The cells or blebs may be fixed with agents such as formaldehyde or glutaldehyde before immunization. See Harlow and Lane, Antibodies: A Laboratory Manual, Cold Spring Harbor Laboratory Press, Cold Spring Harbor, N.Y., 1988, Chapter 15. It is preferred that such anti-whole cell antibodies be monoclonal antibodies. Hybridoma lines producing the desired monoclonal antibodies can be identified by using purified OMP106 polypeptide as the screening ligand. Cells or blebs of any *M. catarrhalis* strain including, but not limited to, ATCC® (American Type Culture Collection) 49143, ATCC® (American Type Culture Collection) 25238, ATCC® (American Type Culture Collection) 25240, ATCC® (American Type Culture Collection) 43617 ATCC® (American Type Culture Collection) 43618, ATCC® (American Type Culture Collection) 43627 and ATCC® (American Type Culture Collection) 43628 are used as the immunogen for inducing these antibodies. Preferably, cells or blebs of a HA cultivar of such strains are used as the immunogen. More preferably, cells or blebs of a HA cultivar of strain ATCC® (American Type Culture Collection) 49143 are used as the immunogen for inducing these antibodies.

Polyclonal antibodies produced by whole cell or bleb immunizations contain antibodies that bind other *M. catarrhalis* outer membrane proteins ("non-anti-OMP106 antibodies") and thus are more cumbersome to use where it is known or suspected that the sample contains other *M. catarrhalis* outer membrane proteins or materials that are cross-reactive with these other outer membrane proteins. Under such circumstances, any binding by the anti-whole cell antibodies of a given sample or band must be verified by coincidental binding of the same sample or band by antibodies that specifically bind OMP106 polypeptide (e.g., anti-OMP106) and/or a OMP106-derived polypeptide, or by competition tests using anti-OMP106 antibodies, OMP106 polypeptide or OMP106-derived polypeptide as the competitor (i.e., addition of anti-OMP106 antibodies, OMP106 polypeptide or OMP106-derived polypeptide to the reaction mix lowers or abolishes sample binding by anti-whole cell antibodies). Alternatively, such polyclonal antisera, containing "non-anti-OMP106" antibodies, may be cleared of such antibodies by standard approaches and methods. For example, the non-anti-OMP106 antibodies may be removed by precipitation with cells of NHA *M. catarrhalis* cultivars or

*M. catarrhalis* strains known not to have the OMP106 polypeptide (e.g., ATCC® (American Type Culture Collection) 8176, more preferably a NHA cultivar of ATCC® (American Type Culture Collection) 49143); or by absorption to columns comprising such cells or outer membrane proteins of such cells.

In further embodiments, useful immunogens for eliciting antibodies of the invention comprise mixtures of two or more of any of the above-mentioned individual immunogens.

Immunization of mammals with the immunogens described herein, preferably humans, rabbits, rats, mice, sheep, goats, cows or horses, is performed following procedures well known to those skilled in the art, for purposes of obtaining antisera containing polyclonal antibodies or hybridoma lines secreting monoclonal antibodies.

Monoclonal antibodies can be prepared by standard techniques, given the teachings contained herein. Such techniques are disclosed, for example, in U.S. Pat. No. 4,271,145 and U.S. Pat. No. 4,196,265. Briefly, an animal is immunized with the immunogen. Hybridomas are prepared by fusing spleen cells from the immunized animal with myeloma cells. The fusion products are screened for those producing antibodies that bind to the immunogen. The positive hybridomas clones are isolated, and the monoclonal antibodies are recovered from those clones.

Immunization regimens for production of both polyclonal and monoclonal antibodies are well-known in the art. The immunogen may be injected by any of a number of routes, including subcutaneous, intravenous, intraperitoneal, intradermal, intramuscular, mucosal, or a combination of these. The immunogen may be injected in soluble form, aggregate form, attached to a physical carrier, or mixed with an adjuvant, using methods and materials well-known in the art. The antisera and antibodies may be purified using column chromatography methods well known to those of skill in the art.

According to the present invention, OMP106 polypeptides of *M. catarrhalis* strains, HA or NHA, are immuno-cross reactive. Thus, antibodies raised to OMP106 polypeptide of one *M. catarrhalis* strain or cultivar specifically bind OMP106 polypeptide and OMP106-derived polypeptides of other *M. catarrhalis* strains and cultivars. For example, polyclonal anti-OMP106 antibodies induced by OMP106 polypeptide of strain ATCC® (American Type Culture Collection) 49143 specifically bind not only the homologous OMP106 polypeptide (i.e., the OMP106 polypeptide of strain ATCC® (American Type Culture Collection) 49143) but also OMP106 polypeptide and/or OMP106-derived polypeptides of other *M. catarrhalis* strains including, but not limited to, ATCC® (American Type Culture Collection) 43628, ATCC® (American Type Culture Collection) 43627, ATCC® (American Type Culture Collection) 43618, ATCC® (American Type Culture Collection) 43617, ATCC® (American Type Culture Collection) 25240 and ATCC® (American Type Culture Collection) 25238.

The antibodies of the invention, including but not limited to anti-OMP106 antibodies, can be used to facilitate isolation and purification of OMP106 polypeptide and OMP106-derived polypeptides. The antibodies may also be used as probes for identifying clones in expression libraries that have inserts encoding OMP106 polypeptide or fragments thereof. The antibodies may also be used in immunoassays (e.g., ELISA, RIA, Westerns) to specifically detect and/or quantitate *M. catarrhalis* in biological specimens. Anti-OMP106 antibodies of the invention specifically bind OMP106 polypeptide and do not bind proteins from related bacterial pathogens such as *Moraxella ovis*, *Moraxella lacunata*, *Moraxella osloensis*, *Moraxella bovis*, *Neisseria meningitidis*, *Neisseria gonorrhoeae*. Thus anti-OMP106 antibodies can be used to diagnose *M. catarrhalis* infections.

The antibodies of the invention, particularly those which are cytotoxic, may also be used in passive immunization to prevent or attenuate *M. catarrhalis* infections of animals, including humans. (As used herein, a cytotoxic antibody is one which enhances opsinization and/or complement killing of the bacterium bound by the antibody) An effective concentration of polyclonal or monoclonal antibodies raised against the immunogens of the invention may be administered to a host to achieve such effects. The exact concentration of the antibodies administered will vary according to each specific antibody preparation, but may be determined using standard techniques well known to those of ordinary skill in the art. Administration of the antibodies may be accomplished using a variety of techniques, including, but not limited to those described in Section 5.6. for the delivery of vaccines.

Prophylactic and therapeutic efficacies of the antibodies of the invention can be determined by standard pharmaceutical procedures in experimental animals. The data obtained from animal studies can be used in formulating a range of dosages for use in humans.

5.6. Vaccines

The present invention also provides therapeutic and prophylactic vaccines against *M. catarrhalis* infections of animals, including mammals, and more specifically rodents, primates, and humans. The preferred use of the vaccines is in humans. The vaccines can be prepared by techniques known to those skilled in the art and would comprise, for example, the antigen in form of an immunogen, a pharmaceutically acceptable carrier, possibly an appropriate adjuvant, and possibly other materials traditionally found in vaccines. An immunologically effective amount of the immunogen to be used in the vaccine is determined by means known in the art in view of the teachings herein.

The vaccines of the present invention comprise an immunologically effective amount of any of the immunogens disclosed in Section 5.5. in a pharmaceutically acceptable carrier.

According to another embodiment, the vaccines of the invention comprise an immunologically effective amount of an inactivated or attenuated HA *M. catarrhalis* cultivar or NHA *M. catarrhalis* cultivar of the invention. An inactivated or attenuated HA *M. catarrhalis* cultivar or NHA *M. catarrhalis* cultivar is obtained using any methods known in the art including, but not limited to, chemical treatment (e.g., formalin), heat treatment and irradiation.

The term "immunologically effective amount" is used herein to mean an amount sufficient to induce an immune response which can prevent *M. catarrhalis* infections or attenuate the severity of any preexisting or subsequent *M. catarrhalis* infections. The exact concentration will depend upon the specific immunogen to be administered, but may be determined by using standard techniques well known to those skilled in the art for assaying the development of an immune response.

Useful polypeptide immunogens include the isolated OMP106 polypeptide and OMP106-derived polypeptides. Preferred immunogens include the purified OMP106 polypeptide and derived polypeptides or peptides of OMP106. The combined immunogen and carrier may be an aqueous solution, emulsion or suspension. In general, the quantity of polypeptide immunogen will be between 0.1 and 500 micrograms per dose. The carriers are known to those skilled in the art and include stabilizers, diluents, and buffers. Suitable stabilizers include carbohydrates, such as sorbitol, lactose, manitol, starch, sucrose, dextran, and glucose and proteins, such as albumin or casein. Suitable diluents include saline, Hanks Balanced Salts, and Ringers solution. Suitable buffers include an alkali metal phosphate, an alkali metal carbonate, or an alkaline earth metal carbonate. The vaccine may also contain one or more adjuvants to improve or enhance the immunological response. Suitable adjuvants include, but are not limited to, peptides; aluminum hydroxide; aluminum phosphate; aluminum oxide; a composition that consists of a mineral oil, such as Marcol 52, or a vegetable oil and one or more emulsifying agents, or surface active substances such as lysolecithin, polycations, polyanions; and potentially useful human adjuvants such as BCG and *Corynebacterium parvum*. The vaccine may also contain other immunogens. Such a cocktail vaccine has the advantage that immunity against several pathogens can be obtained by a single administration. Examples of other immunogens are those used in the known DPT vaccines.

The vaccines of the invention are prepared by techniques known to those skilled in the art, given the teachings contained herein. Generally, an immunogen is mixed with the carrier to form a solution, suspension, or emulsion. One or more of the additives discussed above may be in the carrier or may be added subsequently. The vaccine preparations may be desiccated, for example, by freeze drying for storage purposes. If so, they may be subsequently reconstituted into liquid vaccines by the addition of an appropriate liquid carrier.

The vaccines are administered to humans or other mammals, including rodents and primates. They can be administered in one or more doses. The vaccines may be administered by known routes of administration. Many methods may be used to introduce the vaccine formulations described here. These methods include but are not limited to oral, intradermal, intramuscular, intraperitoneal, intravenous, subcutaneous, and intranasal routes. The preferred routes are intramuscular or subcutaneous injection.

The invention also provides a method for inducing an immune response to *M. catarrhalis* in a mammal in order to protect the mammal against infection and/or attenuate disease caused by *M. catarrhalis*. The method comprises administering an immunologically effective amount of the immunogens of the invention to the host and, preferably, administering the vaccines of the invention to the host.

5.7. Nucleic Acids Encoding OMP106 Polypeptides and OMP106-Derived Polypeptides

The present invention also provides nucleic acids, DNA and RNA, encoding OMP106 polypeptide and OMP106-derived polypeptides. The nucleotide sequence of the entire OMP106 gene is depicted in SEQ ID NO:8. A deduced amino acid sequence of the open reading frame of OMP106 is depicted in SEQ ID NO:9.

In one aspect, the nucleic acids of the invention may be synthesized using methods known in the art. Specifically, a portion of or the entire amino acid sequence of OMP106 polypeptide or an OMP106-derived polypeptide may be determined using techniques well known to those of skill in the art, such as via the Edman degradation technique (see, e.g., Creighton, 1983, Proteins: Structures and Molecular Principles, W. H. Freeman & Co., N.Y., pp. 34-49). The amino acid sequence obtained is used as a guide for the synthesis of DNA encoding OMP106 polypeptide or OMP106-derived polypeptide using conventional chemical approaches or polymerase chain reaction (PCR) amplification of overlapping oligonucleotides.

In another aspect, the amino acid sequence may be used as a guide for synthesis of oligonucleotide mixtures which in turn can be used to screen for OMP106 polypeptide coding sequences in *M. catarrhalis* genomic libraries. Such libraries may be prepared by isolating DNA from cells of any *M. catarrhalis* strain. Preferably the DNA used as the source of the OMP106 polypeptide coding sequence, for both genomic libraries and PCR amplification, is prepared from cells of any *M. catarrhalis* strain including, but not limited to ATCC® (American Type Culture Collection) 49143, ATCC® (American Type Culture Collection) 25238, ATCC® (American Type Culture Collection) 25240, ATCC® (American Type Culture Collection) 43617, ATCC® (American Type Culture Collection) 43618, ATCC® (American Type Culture Collection) 43627 and ATCC® (American Type Culture Collection) 43628.

In the preparation of genomic libraries, DNA fragments are generated, some of which will encode parts or the whole of *M. catarrhalis* OMP106 polypeptide. The DNA may be cleaved at specific sites using various restriction enzymes. Alternatively, one may use DNase in the presence of manganese to fragment the DNA, or the DNA can be physically sheared, as for example, by sonication. The DNA fragments can then be separated according to size by standard techniques, including but not limited to, agarose and polyacrylamide gel electrophoresis, column chromatography and sucrose gradient centrifugation. The DNA fragments can then be inserted into suitable vectors, including but not limited to plasmids, cosmids, bacteriophages lambda or $T_4$, and yeast artificial chromosome (YAC). (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) The genomic library may be screened by nucleic acid hybridization to labeled probe (Benton and Davis, 1977, Science 196: 180; Grunstein and Hogness, 1975, Proc. Natl. Acad. Sci. U.S.A. 72:3961).

The genomic libraries may be screened with a labeled degenerate oligonucleotide corresponding to the amino acid sequence of any peptide of OMP106 polypeptide using optimal approaches well known in the art. In particular embodiments, the screening probe is a degenerate oligonucleotide that corresponds to the peptide having the sequence IGISEADGGKGGANARGDKSIAIGDI-AQALGSQSIAIGDNKIV (SEQ ID NO:1) or a portion thereof. In another embodiment the screening probe may be a degenerate oligonucleotide that corresponds to a peptide having the sequence GTVLGGKK (SEQ ID NO:2). In an additional embodiment, the oligonucleotides GGNACNGTNCT-NGGNGGNAARAAR (SEQ ID NO:3) and GGNACNGTNTTRGGNGGNAARAAR (SEQ ID NO:7), each corresponding to OMP106 peptide GTVLGGKK (SEQ ID NO:2), is used as the probe. In further embodiments, the sequence GAAGCGGACGGGGGGAAAGGCGGAGC-CAATGCGCGCGGTGATAAATCC® (American Type Culture Collection)ATTGCTATTGGTG ACATTGCGCAA (SEQ ID NO:4) or any fragments thereof, or any complement of the sequence or fragments may be used as the probe. Any probe used preferably is 15 nucleotides or longer.

Clones in libraries with insert DNA encoding the OMP106 polypeptide or fragments thereof will hybridize to one or more of the degenerate oligonucleotide probes. Hybridization of such oligonucleotide probes to genomic libraries are carried out using methods known in the art. For example, hybridization with the two above-mentioned oligonucleotide probes may be carried out in 2×SSC, 1.0% SDS at 50° C. and washed using the same conditions. In a particular embodiment, ATCC® (American Type Culture Collection) 49143 DNA sequence encoding the whole or a part of the OMP106 polypeptide is a HindIII restriction fragment of about 8,000 bp in length or a DRAI restriction fragment of about 4,200 bp in length.

In yet another aspect, clones of nucleotide sequences encoding a part or the entire OMP106 polypeptide or OMP106-derived polypeptides may also be obtained by screening *M. catarrhalis* expression libraries. For example, *M. catarrhalis* DNA is isolated and random fragments are prepared and ligated into an expression vector (e.g., a bacteriophage, plasmid, phagemid or cosmid) such that the inserted sequence in the vector is capable of being expressed by the host cell into which the vector is then introduced. Various screening assays can then be used to select for the expressed OMP106 polypeptide or OMP106-derived polypeptides. In one embodiment, the various anti-OMP106 antibodies of the invention (see Section 5.5) can be used to identify the desired clones using methods known in the art. See, for example, Harlow and Lane, 1988, Antibodies: A Laboratory Manual, Cold Spring Harbor Laboratory Press, Cold Spring Harbor, N.Y., Appendix IV. Clones or plaques from the library are brought into contact with the antibodies to identify those clones that bind.

In an embodiment, colonies or plaques containing DNA that encodes OMP106 polypeptide or OMP106-derived polypeptide could be detected using DYNA Beads according to Olsvick et al., 29th ICAAC, Houston, Tex. 1989, incorporated herein by reference. Anti-OMP106 antibodies are crosslinked to tosylated DYNA Beads M280, and these antibody-containing beads would then be used to adsorb to colonies or plaques expressing OMP106 polypeptide or OMP106-derived polypeptide. Colonies or plaques expressing OMP106 polypeptide or OMP106-derived polypeptide is identified as any of those that bind the beads.

Alternatively, the anti-OMP106 antibodies can be nonspecifically immobilized to a suitable support, such as silica or Celite™ resin. This material would then be used to adsorb to bacterial colonies expressing OMP106 polypeptide or OMP106-derived polypeptide as described in the preceding paragraph.

In another aspect, PCR amplification may be used to produce substantially pure DNA encoding a part of or the whole of OMP106 polypeptide from *M. catarrhalis* genomic DNA. Oligonucleotide primers, degenerate or otherwise, corresponding to known OMP106 polypeptide sequences can be used as primers. In particular embodiments, an oligonucleotide, degenerate or otherwise, encoding the peptide IGISEADGGKGGANARGDKSIAIGDI-AQALGSQSIAIGDNKIV (SEQ ID NO:1) or any portion thereof may be used as the 5' primer. For example, a 5' primer may be the nucleotide sequence GAAGCGGACGGGGG-GAAAGGCGGAGCCAATGCGCGCGGTGATAAATCC® (American Type Culture Collection) ATTGCTATTGGTG ACATTGCGCAA (SEQ ID NO:4) or any portion thereof. Nucleotide sequences, degenerate or otherwise, that are reverse complements of sequence encoding GTVLGGKK (SEQ ID NO:2) may be used as the 3' primer.

PCR can be carried out, e.g., by use of a Perkin-Elmer Cetus thermal cycler and Taq polymerase (Gene Amp™ ). One can choose to synthesize several different degenerate primers, for use in the PCR reactions. It is also possible to vary the stringency of hybridization conditions used in priming the PCR reactions, to allow for greater or lesser degrees of nucleotide sequence similarity between the degenerate primers and the corresponding sequences in *M. catarrhalis* DNA. After successful amplification of a segment of the sequence encoding OMP106 polypeptide, that segment may be molecularly cloned and sequenced, and utilized as a probe to isolate a complete genomic clone. This, in turn, will permit the determination of the gene's complete nucleotide sequence, the analysis of its expression, and the production of its protein product for functional analysis, as described infra.

Once an OMP106 polypeptide coding sequence has been isolated from one *M. catarrhalis* strain or cultivar, it is possible to use the same approach to isolate OMP106 polypeptide coding sequences from other *M. catarrhalis* strains and cultivars. It will be recognized by those skilled in the art that the DNA or RNA sequence encoding OMP106 polypeptide (or fragments thereof) of the invention can be used to obtain other DNA or RNA sequences that hybridize with it under conditions of moderate to high stringency, using general techniques known in the art. Hybridization with an OMP106 sequence from one *M. catarrhalis* strain or cultivar under high stringency conditions will identify the corresponding sequence from other strains and cultivars. High stringency conditions vary with probe length and base composition. The formula for determining such conditions are well known in the art. See Sambrook et al., 1989, Molecular Cloning, A Laboratory Manual, Cold Spring Harbor Press, NY, Chapter 11. As used herein high stringency hybridization conditions as applied to probes of greater than 300 bases in length involve a final wash in 0.1×SSC/0.1% SDS at 68° C. for at least 1 hour (Ausubel, et al., Eds., 1989, Current Protocols in Molecular Biology, Vol. 1, Greene Publishing Associates, Inc. and John Wiley & Sons, Inc., New York, at page 2.10.3). In particular embodiments, the high stringency wash in hybridization using a probe having the sequence of SEQ ID NO:4 or its complement is 2×SSC, 1% SDS at 50° C. for about 20 to about 30 minutes.

One skilled in the art would be able to identify complete clones of OMP106 polypeptide coding sequence using approaches well known in the art. The extent of OMP106 polypeptide coding sequence contained in an isolated clone may be ascertained by sequencing the cloned insert and comparing the deduced size of the polypeptide encoded by the open reading frames (ORFs) with that of OMP106 polypeptide and/or by comparing the deduced amino acid sequence with that of known amino acid sequence of purified OMP106 polypeptide. Where a partial clone of OMP106 polypeptide coding sequence has been isolated, complete clones may be isolated by using the insert of the partial clone as hybridization probe. Alternatively, a complete OMP106 polypeptide coding sequence can be reconstructed from overlapping partial clones by splicing their inserts together.

Complete clones may be any that have ORFs with deduced amino acid sequence matching that of OMP106 polypeptide or, where the complete amino acid sequence of the latter is not available, that of a peptide fragment of OMP106 polypeptide and having a molecular weight corresponding to that of OMP106 polypeptide. Further, complete clones may be identified by the ability of their inserts, when placed in an expression vector, to produce a polypeptide that binds antibodies specific to the amino-terminal of OMP106 polypeptide and antibodies specific to the carboxyl-terminal of OMP106 polypeptide.

Nucleic acid sequences encoding OMP106-derived polypeptides may be produced by methods well known in the art. In one aspect, sequences encoding OMP106-derived polypeptides can be derived from OMP106 polypeptide coding sequences by recombinant DNA methods in view of the teachings disclosed herein. For example, the coding sequence of OMP106 polypeptide may be altered creating amino acid substitutions that will not affect the immunogenicity of the OMP106 polypeptide or which may improve its immunogenicity. Various methods may be used, including but not limited to oligonucleotide directed, site specific mutagenesis. These and other techniques known in the art may be used to create single or multiple mutations, such as replacements, insertions, deletions, and transpositions, as described in Botstein and Shortle, 1985, Science 229:1193 1210.

Further, DNA of OMP106 polypeptide coding sequences may be truncated by restriction enzyme or exonuclease digestions. Heterologous coding sequence may be added to OMP106 polypeptide coding sequence by ligation or PCR amplification. Moreover, DNA encoding the whole or a part of an OMP-derived polypeptide may be synthesized chemically or using PCR amplification based on the known or deduced amino acid sequence of OMP106 polypeptide and any desired alterations to that sequence.

The identified and isolated DNA containing OMP106 polypeptide or OMP106-derived polypeptide coding sequence can be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved DNA may be modified by homopolymeric tailing. Recombinant molecules can be introduced into host cells via transformation, transfection, infection, electroporation, etc., so that many copies of the gene sequence are generated.

In an alternative method, the desired DNA containing OMP106 polypeptide or OMP106-derived polypeptide coding sequence may be identified and isolated after insertion into a suitable cloning vector in a "shot gun" approach. Enrichment for the desired sequence, for example, by size fractionation, can be done before insertion into the cloning vector.

In specific embodiments, transformation of host cells with recombinant DNA molecules that contain OMP106 polypeptide or OMP106-derived polypeptide coding sequence enables generation of multiple copies of such coding sequence. Thus, the coding sequence may be obtained in large quantities by growing transformants, isolating the recombinant DNA molecules from the transformants and, when necessary, retrieving the inserted coding sequence from the isolated recombinant DNA.

5.8. Recombinant Production of OMP106 Polypeptide and OMP106-Derived Polypeptides OMP106 polypeptide and OMP106-derived polypeptides of the invention may be produced through genetic engineering techniques. In this case, they are produced by an appropriate host cell that has been transformed by DNA that codes for the polypeptide. The nucleotide sequence encoding OMP106 polypeptide or OMP106-derived polypeptides of the invention can be inserted into an appropriate expression vector, i.e., a vector which contains the necessary elements for the transcription and translation of the inserted polypeptide-coding sequence. The nucleotide sequences encoding OMP106 polypeptide or OMP106-derived polypeptides is inserted into the vectors in a manner that they will be expressed under appropriate conditions (e.g., in proper orientation and correct reading frame and with appropriate expression sequences, including an RNA polymerase binding sequence and a ribosomal binding sequence).

A variety of host-vector systems may be utilized to express the polypeptide-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. Preferably, the host cell is a bacterium, and most preferably the bacterium is *E. coli, B. subtilis* or *Salmonella*.

The expression elements of vectors vary in their strengths and specificities. Depending on the host-vector system utilized, any one of a number of suitable transcription and translation elements may be used. In a specific embodiment, a chimeric protein comprising OMP106 polypeptide or OMP106-derived polypeptide sequence and a pre and/or pro sequence of the host cell is expressed. In other specific embodiments, a chimeric protein comprising OMP106 polypeptide or OMP106-derived polypeptide sequence and an affinity purification peptide is expressed. In further specific embodiments, a chimeric protein comprising OMP106 polypeptide or OMP106-derived polypeptide sequence and a useful immunogenic peptide or polypeptide is expressed. In preferred embodiments, OMP106-derived polypeptide expressed contains a sequence forming either an outer-surface epitope or the receptor-binding domain of native OMP106 polypeptide.

Any method known in the art for inserting DNA fragments into a vector may be used to construct expression vectors containing a chimeric gene consisting of appropriate transcriptional/translational control signals and the polypeptide coding sequences. These methods may include in vitro recombinant DNA and synthetic techniques and in vivo recombinants (genetic recombination). Expression of a nucleic acid sequence encoding OMP106 polypeptide or OMP106-derived polypeptide may be regulated by a second nucleic acid sequence so that the inserted sequence is expressed in a host transformed with the recombinant DNA molecule. For example, expression of the inserted sequence may be controlled by any promoter/enhancer element known in the art. Promoters which may be used to control expression of inserted sequences include, but are not limited to the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42) for expression in animal cells; the promoters of β-lactamase (Villa-Kamaroff et al., 1978, Proc. Natl. Acad. Sci. U.S.A. 75:3727-3731), tac (DeBoer et al., 1983, Proc. Natl. Acad. Sci. U.S.A. 80:21-25), $\lambda P_L$, or trc for expression in bacterial cells (see also "Useful proteins from recombinant bacteria" in Scientific American, 1980, 242:74-94); the nopaline synthetase promoter region or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120) for expression implant cells; promoter elements from yeast or other fungi such as the Gal4 promoter, the ADC (alcohol dehydrogenase) promoter, PGK (phosphoglycerol kinase) promoter, alkaline phosphatase promoter.

Expression vectors containing OMP106 polypeptide or OMP106-derived polypeptide coding sequences can be identified by three general approaches: (a) nucleic acid hybridization, (b) presence or absence of "marker" gene functions, and (c) expression of inserted sequences. In the first approach, the presence of a foreign gene inserted in an expression vector can be detected by nucleic acid hybridization using probes comprising sequences that are homologous to the inserted OMP106 polypeptide or OMP106-derived polypeptide coding sequence. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the OMP106 polypeptide or OMP106-derived polypeptide coding sequence is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of OMP106 polypeptide or OMP106-derived polypeptide in in vitro assay systems, e.g., binding to an OMP106 ligand or receptor, or binding with anti-OMP106 antibodies of the invention, or the ability of the host cell to hemagglutinate or the ability of the cell extract to interfere with hemagglutination by *M. catarrhalis*.

Once a particular recombinant DNA molecule is identified and isolated, several methods known in the art may be used to propagate it. Once a suitable host system and growth conditions are established, recombinant expression vectors can be propagated and prepared in quantity. As explained above, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered OMP106 polypeptide or OMP106-derived polypeptide may be controlled. Furthermore, different host cells have characteristic and specific mechanisms for the translational and post-translational processing and modification of proteins. Appropriate cell lines or host systems can be chosen to ensure the desired modification and processing of the foreign protein expressed.

5.9. Reagents

The polypeptides, peptides, antibodies and nucleic acids of the invention are useful as reagents for clinical or medical diagnosis of *M. catarrhalis* infections and for scientific research on the properties of pathogenicity, virulence, and infectivity of *M. catarrhalis,* as well as host defense mechanisms. For example, DNA and RNA of the invention can be used as probes to idencify the presence of *M. catarrhalis* in biological specimens by hybridization or PCR amplification. The DNA and RNA can also be used to identify other bacteria that might encode a polypeptide related to the *M. catarrhalis* OMP106.

The polypeptides and peptides of the invention may be used to prepare polyclonal and monoclonal antibodies that can be used to further purify compositions containing the polypeptides of the invention by affinity chromatography. The polypeptides and peptides can also be used in standard immunoassays to screen for the presence of antibodies to *M. catarrhalis* in a sample.

It is to be understood that the application of the teachings of the present invention to a specific problem or environment will be within the capabilities of one having ordinary skill in the art in light of the teachings contained herein. Examples of the products of the present invention and processes for their preparation and use appear in the following example.

6. EXAMPLE

Isolation and Characterization of the OMP106 Polypeptide and Gene Encoding Same from Strain ATCC® (American Type Culture Collection) 49143 or Other Strains 6.1. Material and Methods 6.1.1. Hemagglutination Assay Hemagglutination by *M. catarrhalis* was tested as described by Soto-Hernandez et al. (J. Clin. Microbiol. 27:903-908) except 5%, instead of 3%, v/v erythrocytes were used in a slide agglutination assay. Initial hemagglutination assays were performed using 20 µg of bacterial cells (wet weight). Since *M. catarrhalis* ATCC® (American Type Culture Collection) strain 49143 grown on blood agar plates at 35° C. gave a strong hemagglutination reaction, it was selected as the reference strain. Serially diluting ATCC® (American Type Culture Collection) strain 49143 in 1:2 dilutions resulted in decreasing hemagglutination reactions. Scores of ++++ to + were based on the hemagglutination observed by ATCC® (American Type Culture Collection) strain 49143 after serial 1:2 dilutions so that a + reaction resulted using ¼ the number of cells required to achieve a +++ reaction.

6.1.2. Inhibition of Hemagglutination

*M. catarrhalis* ATCC® (American Type Culture Collection) 49143 cell suspension was serially diluted 1:2, and the dilution that yielded a + hemagglutination reaction when 7 µl of Dulbecco's phosphate buffered saline and 7 µl of 5% (v/v) human $O^+$ erythrocytes was used to assay inhibition of hemagglutination by simple sugars and sugar derivatives. To determine if simple sugars or sugar derivatives could inhibit hemagglutination by *M. catarrhalis,* 7 µl of a given sugar at 500 mM was mixed with 7 µl of *M. catarrhalis* cells and incubated for 5 minutes to allow the sugar to interact with the cells. Then 7 µl of 5% (v/v) human $O^+$ erythrocytes were added and the hemagglutination was scored after 1 minute. Each sugar and sugar derivative was tested for the ability to inhibit hemagglutination. Then the stock of each sugar and sugar derivative was serially diluted 1:2, and these dilutions were assayed for their ability to inhibit hemagglutination using the procedure described above. In this manner, the minimal concentration of carbohydrate required to inhibit hemagglutination was determined.

6.1.3. Ligand and Receptor Binding

*M. catarrhalis* binding to animal cell glycolipid receptors was examined using thin layer chromatography (TLC) fractionation of the host cell glycolipids and labeled cell overlay of the chromatogram following the procedures described by Magnani et al., 1982, J. Biol. Chem. 257:14365-14369. Briefly, glycolipids obtained from Matreya Inc. (Pleasant Gap, Pa.) were resolved on high performance thin layer chromatograph plates (HPTLC) in chloroform, methanol, water (5:4:1) The plates were either stained with orcinol at 100° C., or were overlaid with $^{125}$I-labeled *M. catarrhalis* blebs prepared as previously described (Murphy and Loeb, 1989, Microbial Pathogen. 6:159-174) at $2 \times 10^6$ cpm/ml for 2 hours. The plates were then washed 5 times, dried and exposed to X-ray film.

6.1.4. OG Extraction of OMPS

Strains of *M. catarrhalis* were each grown at 35° C. at 200 rpm in 1 liter of Mueller Hinton broth in a 4 liter flask. Outer membrane protein (OMP) preparations were isolated by treating 50 mg of cells (wet weight) with 0.67 ml of 1.25% n-octyl β-D-glucopyranoside (i.e., octyl glucoside; OG) in phosphate buffered saline (PBS) for 30 minutes at room temperature. Cells were pelleted in a microcentrifuge for 5 minutes and the supernatant was used as an octyl glucoside extract. Comparison of protein profiles of these extracts from a number of strains of *M. catarrhalis* to those of blebs (i.e., outer membrane vesicles) isolated by differential centrifugation, which are highly enriched for outer membrane proteins (OMPs) from *M. catarrhalis* (Murphy and Loeb, 1989, Microbial Pathogen. 6:159-174) indicates the octyl glucoside extracts contain predominately outer membrane proteins of *M. catarrhalis* (FIG. 1). This indicated that octyl glycoside extraction provided a more rapid procedure with a higher yield of outer membrane proteins as compared to outer membrane proteins prepared from blebs.

6.1.5. Proteolytic Digestion of OMP106

50 mg of cells from ATCC® (American Type Culture Collection) strain 49143 in 1 ml of Dulbecco's phosphate buffered saline were digested for 1 hour at room temperature with the following proteases: TLCK-treated chymotrypsin (5 mg), Proteinase K (5 mg), TPCK-treated trypsin (5 mg), or protease V8 (100 Units). All proteases were obtained from Sigma Chemicals (St. Louis, Mo.). Immediately following the protease treatment, cells were washed once in PBS and resuspended in 1 ml of PBS and the hemagglutinating activity was tested. Additionally, protease-treated bacterial cells were extracted with octyl glucoside so the outer membrane proteins could be resolved to identify specific proteins that may have been digested by the proteases.

6.1.6. Non-Hemagglutinating Cultivars

Normally, hemagglutinating *M. catarrhalis* cultures are grown in shaker flasks containing Mueller Hinton Broth at 35 to 37° C. at 200 rpm for 24 to 48 hours. Cells taken directly from a blood agar plate or an agar plate of Mueller Hinton media also express the hemagglutinating phenotype. To select for a non-hemagglutinating (NHA) cultivar, ATCC® (American Type Culture Collection) strain 49143 was serially passaged every 5 days in static cultures grown in Mueller Hinton broth at 35° C. With each passage, inoculum was taken only from the surface of the broth culture. By the second passage, a floating mat of cells had developed and this mat of cells was used as the inoculum for subsequent cultures. Serial culturing in this manner produced NHA cultivars of ATCC® (American Type Culture Collection) 49143 typically after three passages.

5 6.1.7. Isolation of OMP106 Polypeptide

OMP106 polypeptide from outer membrane extract of *M. catarrhalis* ATCC® (American Type Culture Collection) 49143 is detected (e.g., by silver staining or anti-OMP106 antibodies) in denaturing gels only after the extract has been incubated at 100° C. for five minutes. In order to determine if the appearance of the OMP106 band after incubation at 100° C. is the result of lower molecular weight proteins aggregating during boiling, or if the boiling allows a normally aggregated protein to enter the gel, an unboiled octyl glucoside outer membrane extract of ATCC® (American Type Culture Collection) 49143 was analyzed on a native polyacrylamide gel. Specific regions of the gel including that immediately below the sample well were excised and boiled. The resulting samples were then resolved on a denaturing polyacrylamide gel and stained with silver stain (Silver Stain Plus, Catalog number 161-0449, BioRad Laboratories, Richmond, Calif.). For N-terminal sequencing, an octyl glucoside outer membrane extract of ATCC® (American Type Culture Collection) 49143 was mixed with PAGE sample buffer containing SDS, and was incubated for 5 minutes in boiling water bath. The proteins were then resolved on a 12% PAG with SDS and transferred to a PVDF membrane by electroblotting. The region of the membrane containing the OMP106 band was then cut out for amino-terminal sequencing. None of the PAGE procedures used to isolate the OMP106 polypeptide used reducing agents in the sample or gel buffers.

6.1.8. Anti-OMP106 Antiserum

Antiserum to OMP106 were prepared by resolving OMP106 polypeptide from a HA cultivar of ATCC®G (American Type Culture Collection) 49143 in a denaturing sodium dodecylsulfate polyacrylamide gel as previously described (Lammeli, 1970, Nature 227:680-685), and cutting the OMP106-containing band out of the gel. The excised band was macerated and injected into a rabbit to generate antiserum to OMP106 polypeptide. The antiserum was used to inhibit hemagglutination as described in section 6.1.2. supra, but using the antiserum in place of the carbohydrate. The antiserum was also examined for complement-mediated cytotoxic activity against *M. catarrhalis* as described in section 7.

6.1.9. Western Blots with Anti-OMP106 Antiserum

*M. catarrhalis* ATCC® (American Type Culture Collection) 49143, ATCC® (American Type Culture Collection) 43628, ATCC® (American Type Culture Collection) 43627, ATCC® (American Type Culture Collection) 43618 ATCC® (American Type Culture Collection) 43617, ATCC® (American Type Culture Collection) 25240, ATCC® (American Type Culture Collection) 25238, and ATCC® (American Type Culture Collection) 8176; *M. ovis* ATCC® (American Type Culture Collection) 33078; *M. lacunta* ATCC® (American Type Culture Collection) 17967; *M. bovis* ATCC® (American Type Culture Collection) 10900; *M. osloensis* ATCC® (American Type Culture Collection) 10973; *Neisseria gonorrhoeae* (clinical isolate); and *N. meningitidis* ATCC® (American Type Culture Collection) 13077 were grown on chocolate agar plates for 48 hours at 35° C. in 5% $CO_2$. Cells were removed by scraping the colonies from the agar surface using a polystyrene inoculating loop. Cells were then solubilized by suspending 30 μg of cells in 150 μl of PAGE sample buffer (360 mM Tris buffer [pH 8.8], containing 4% sodium dodecylsulfate and 20% glycerol), and incubating the suspension at 100° C. for 5 minutes. The solubilized cells were resolved on 12% polyacrylamide gels as per Laemmli and the separated proteins were electrophoretically transferred to PVDF membranes at 100 V for 1.5 hours as previously described (Thebaine et al. 1979, Proc. Natl. Acad. Sci. USA 76:4350-4354) except 0.05% sodium dodecylsulfate was added to the transfer buffer to facilitate the movement of proteins from the gel. The PVDF membranes were then pretreated with 25 ml of Dulbecco's phosphate buffered saline containing 0.5% sodium casein, 0.5% bovine serum albumin and 1% goat serum. All subsequent incubations were carried out using this pretreatment buffer.

PVDF membranes were incubated with 25 ml of a 1:500 dilution of preimmune rabbit serum or serum from a rabbit immunized with OMP106 polypeptide (as described above) for 1 hour at room temperature. PVDF membranes were then washed twice with wash buffer (20 mM Tris buffer [pH 7.5.] containing 150 mM sodium chloride and 0.05% Tween-20).

PVDF membranes were incubated with 25 ml of a 1:5000 dilution of peroxidase-labeled goat anti-rabbit IgG (Jackson ImmunoResearch Laboratories, West Grove Pa. Catalog number 111-035-003) for 30 minutes at room temperature. PVDF membranes were then washed 4 times with wash buffer, and were developed with 3,3' diaminobenzidine tetrahydrochloride and urea peroxide as supplied by Sigma Chemical Co. (St. Louis, Mo. catalog number D-4418) for 4 minutes each.

6.1.10. Anti-OMP106 Immunofluorescence Staining of Cell Surface

*M. catarrhalis* ATCC® (American Type Culture Collection) 49143 was grown overnight at 35° C. in a shaking water bath in Mueller Hinton broth. The cells were pelleted by centrifugation and then resuspended in an equal volume of Dulbecco's modification of phosphate buffered saline without calcium or magnesium (PBS/MC). 20 µl of the cell suspension was applied to each of 5 clean microscope slides. After setting for 10 seconds, the excess fluid was removed with a micropipettor, and the slides were allowed to air dry for 1 hour. The slides were then heat fixed over an open flame until the glass was warm to the touch. The slides were initially treated with 40 µl of 1:40 dilution of anti-OMP106 antiserum or preimmune serum from the same animal diluted in PBS/MC, or PBS/MC for 10 minutes, then washed 5 times with PBS/MC. The slides were treated with 40 µl of 5 µg/ml PBS/MC of fluorescein isothiocyanate-labeled goat antibody to rabbit IgG (Kirkegaard and Perry Laboratories, Inc, Gaithersburg, Md. catalog number 02-15-06). The slides were incubated in the dark for 10 minutes and were washed 5 times in PBS/MC. Each slide was stored covered with PBS/MC under a cover slide and was viewed with a fluorescence microscope fitted with a 489 nm filter. For each sample five fields-of-view were visually examined to evaluate the extent of straining.

6.2. Results 6.2.1. Hemagglutination Activity

The agglutination activity of *M. catarrhalis* with respect to erythrocytes is species specific with the strongest activity observed with human erythrocytes. Rabbit erythrocytes are also agglutinated by *M. catarrhalis,* but less dramatically than are human cells. The erythrocytes from mouse, horse or sheep were not agglutinated (see Table 1).

TABLE 1

Strength of hemagglutination of erythrocytes from various species using *M. catarrhalis* ATCC ® (American Type Culture Collection) 49143

| Source of Score for erythrocytes | Source of Score for hemagglutination[a] |
|---|---|
| Human | ++++ |
| Rabbit | ++ |
| Mouse | − |
| Horse | − |
| Sheep | − |

6.2.2. OMP106 Receptors and Ligands

*M. catarrhalis* hemagglutination activity is due to binding to globotetrose ($Gb_4$). Blebs from hemagglutinating strains bind to a glycolipid having $Gb_4$, whereas non-hemagglutinating strains do not bind to the same glycolipid (see FIG. 2). *M. catarrhalis* hemagglutination activity is inhibited by monosaccharide constituents of $Gb_4$ or derivatives of such monosaccharides, with the most potent inhibitors being N-acetyl galactosamine and galactose (especially the alpha anomer of the galactose) (see Table 2).

TABLE 2

The minimum concentration of sugars required to inhibit hemagglutination (MIC) by *M. catarrhalis*

| Sugar | MIC (mM)* |
|---|---|
| D-Glucose | >167 |
| D-Mannose | 83 |
| D-Galactose | 41 |
| L-Fucose | 83 |
| N-acetyl-D-Glucosamine | >167 |
| N-acetyl-D-Galactosamine | 41 |
| Methyl-α-Glucose | >167 |
| Methyl-α-Mannose | 167 |
| Methyl-α-Galactose | 10 |
| Methyl-β-galactose | 83 |

*Minimal concentration of sugar required to inhibit a 1+hemagglutination reaction by *M. catarrhalis* ATCC® (American Type Culture Collection) 49143 with 5% washed human $O^+$ erythrocytes.

Both N-acetyl galactosamine and alpha-galactose are part of the $Gb_4$ tetrasaccharide. The correlation between hemagglutination and binding to $Gb_4$, and the observation that hemagglutination is inhibited by monosaccharides that comprise the $Gb_4$ receptor suggest that *M. catarrhalis* cells bind to the tetrasaccharide $Gb_4$. This tetrasaccharide is present on human erythrocytes and tissues, and could mediate *M. catarrhalis* attachment to eukaryotic membranes.

6.2.3. Identification of OMP106 Polypeptide

Proteolytic digestion of *M. catarrhalis* cells, and subsequent analysis of hemagglutination by the digested cells demonstrated that protease treatment with chymotrypsin and proteinase K destroyed the hemagglutination activity, and treatment with trypsih partially destroyed hemagglutination activity, indicating the hemagglutinating activity is protein mediated. Analysis of the OMP protein profiles of protease digested *M. catarrhalis* cells showed that multiple proteins had been degraded in each sample, so the profiles did not provide a clue as to which protein is directly responsible for or indirectly contributed to the hemagglutination activity (see FIG. 3).

Since protease treatment indicated a polypeptide is directly or indirectly responsible for hemagglutination activity, we used SDS-PAGE to compare the OMP profiles from hemagglutinating strains with the OMP profiles from non-hemagglutinating strains (FIG. 4). Analysis of the differences between these profiles indicated that the hemagglutinating strains had two unique polypeptides, one with an apparent molecular weight of 27 kD (designated OMP27) and the other was the only protein with an apparent molecular weight of greater than 106 kD (designated OMP106). Notably, the OMP106 polypeptide band was absent in the OMP preparations of various protease treated cells that have reduced or no hemagglutination activity, whereas the OMP27 band was present in the OMP preparation of proteinase K treated cells that have no hemagglutination activity. Additionally, the OMP106 polypeptide band was not degraded by proteinase V8 digestion, which did not affect hemagglutination activity of treated cells.

6.2.4. OMP Profile of NHA Cultivars

Serial culturing of NHA cultivar of ATCC® (American Type Culture Collection) 49143 in static culture at 35° C. produced a NHA cultivar (designated 49143-NHA) by the third passage of the culture. This loss of the hemagglutination activity was repeatable. Analysis of OMP profiles of OG outer membrane extracts of the HA and NHA cultivars showed that the OMP106 polypeptide band was missing from the 49143-NHA extract (FIG. 5). This suggested that OMP106 polypeptide is the *M. catarrhalis* hemagglutinin (i.e., OMP106 polypeptide binds $Gb_4$ receptor or is a subunit of a homopolymeric protein that binds $Gb_4$ receptor) or forms a part of the *M. catarrhalis* hemagglutinin (i.e., OMP106 polypeptide is a subunit of a heteropolymeric protein that binds $Gb_4$ receptor).

6.2.5. OMP106 and Hemagglutination

Polyclonal antiserum raised to ATCC® (American Type Culture Collection) 49143 OMP106 polypeptide neutralized hemagglutination by ATCC® (American Type Culture Collection) 49143, as well as that by heterologous ATCC® (American Type Culture Collection) 43627. This further supports the conclusion that *M. catarrhalis* hemagglutinating activity comprises OMP106 polypeptide, and that OMP106 polypeptide is antigenically conserved among strains. See also FIG. 9A, which shows antibodies in the polyclonal antiserum binding OMP106 polypeptide of heterologous *M. catarrhalis* strains.

6.2.6. Outer Surface Location of OMP106

Rabbit anti-OMP106 antiserum was used in indirect immunofluorescence staining to determine if OMP106 polypeptide is exposed on the outer surface of *M. catarrhalis* cells. *M. catarrhalis* cells treated with anti-OMP106 antiserum stained more intensely and uniformly than did cells treated with preimmune serum or PBS/MC. This indicated that in intact *M. catarrhalis* cells OMP106 polypeptide was reactive with anti-OMP106 antibodies. This result indicates that OMP106 polypeptide is exposed on the outer surface of *M. catarrhalis*. This finding is consistent with OMP106 polypeptide having a role in hemagglutination and, moreover, indicates that OMP106 polypeptide would be useful as a vaccine.

6.2.7. Properties of OMP106 Polypeptide

OMP106 polypeptide exists as a large protein complex in its native state or aggregates when extracted with octyl glucoside. This conclusion is supported by the finding that extracting *M. catarrhalis* cells with octyl glucoside will solubilize OMP106 polypeptide, but the extracted OMP106 polypeptide does not enter denaturing PAGs unless the extract is first incubated at 100° C. (FIG. 6). Further, the OMP106 polypeptide band does not appear to form from lower molecular weight polypeptides that polymerize or aggregate upon heating, since OMP106 polypeptide in a non-heat denatured sample is trapped in the sample well and enters the resolving gel only if the sample has been first incubated at 100° C. This biochemical property is very useful for identifying OMP106 polypeptide in various gels.

Using octyl glucoside extracts of M. catarrhalis, then incubating the extracts with sodium dodecyl sulfate at 100° C., and resolving the proteins on a denaturing polyacrylamide gel, we have estimated the apparent molecular weight of OMP106 polypeptide from various strains of *M. catarrhalis*, specifically those of ATCC® (American Type Culture Collection) 25238, ATCC® (American Type Culture Collection) 25240, ATCC® (American Type Culture Collection) 43617, ATCC® (American Type Culture Collection) 43618, ATCC® (American Type Culture Collection) 43627 and ATCC® (American Type Culture Collection) 43628, to range from about 180 kD to about 230 kD (FIG. 9A), whereas the OMP106 polypeptide of strain ATCC® (American Type Culture Collection) 49143 appears to have an apparent weight of about 190 kD (FIG. 6).

OMP106 polypeptide of strain ATCC® (American Type Culture Collection) 49143 was extracted from the gel slice and was sequenced. N-terminal sequencing of the mature OMP106 polypeptide isolated from the outer membrane of ATCC® (American Type Culture Collection) 49143 yielded the following sequence: IGISEADGGKGGANARGDKSI-AIGDIAQALGSQSIAIGDNKIV (SEQ ID NO: 1). Further analysis of the nucleotide sequence encoding the mature OMP106 protein demonstrated that the amino terminal sequence is: GIGISEADGGKGGANARGDKSIAIGDI-AQALGSQSIAIGD (SEQ ID NO:11) Additionally, an internal peptide of OMP106 produced by digestion with Lys-C (Fernandez et al., 1994, Anal Biochem 218:112-117) has been isolated and yielded the following sequence: GTVLG-GKK (SEQ ID NO:2).

We generated three oligonucleotide probes. Two probes correspond to the internal peptide GTVLGGKK, one has the following sequence GGNACNGTNCTNGGNG-GNAARAAR (SEQ ID NO:3), the other has the following sequence GGNACNGTNTTRGGNGGNAARAAR (SEQ ID NO:7). The other probe, Mc 5-72, encoding an internal fragment (SEQ ID NO:5) of the amino-terminal sequence of OMP106 (SEQ ID NO:1) has the following sequence GAAGCGGACGGGGGGAAAGGCGGAGC-CAATGCGCGCGGTGATAAATCC® (American Type Culture Collection)ATTGCTATTGGTG ACATTGCGCAA (SEQ ID NO:4). Hybridization of the Mc 5-72 probe to a complete HindIII or DraI digest of *M. catarrhalis* DNA in each instance produced a single band in Southern blot analysis (FIG. 7). The hybridizing band in the HindIII digest has an approximate size of 8.0 kb; the hybridizing band in the DraI digest has an approximate size of 4.2 kb (FIG. 7).

6.2.8. Conservation of OMP106 Polypeptide

Western blot analysis of outer membrane protein extracts of a number of *M. catarrhalis* strains and related species of bacteria showed that the anti-OMP106 antibodies binds to a polypeptide of about 180 Kd to about 230 kD in many *M. catarrhalis* strains, both HA and NHA strains or cultivars (FIG. 9A). The anti-OMP106 antibodies did not bind to any polypeptide in the protein extracts of related bacteria (FIG. 8A). These results demonstrate the following: 1) Anti-OMP106 antibodies may be used to specifically identify and distinguish *M. catarrhalis* from related species of bacteria. 2) OMP106 polypeptide may be used to generate antibodies that have diagnostic application for identification of *M. catarrhalis*. 3) Antibodies to OMP106 polypeptide of one strain (e.g., OMP106 of ATCC® (American Type Culture Collection) 49143) may be used to identify and isolate the corresponding OMP106 polypeptide of other *M. catarrhalis* strains. Interestingly, the Western blot results show that many of the NHA *M. catarrhalis* strains have OMP106 polypeptide in OG extracts of their outer membranes. This finding and the fact that silver staining of OMPs from OG outer membrane extracts of NHA *M. catarrhalis* strains after PAGE does not reveal a band in the 180 kD to 230 kD range indicate that OMP106 polypeptide is expressed by most *M. catarrhalis* strains or cultivars but that, in order to be active in hemagglutination (i.e., binding to receptor on mammalian cell surfaces) or silver stainable, the OMP106 polypeptide must be appropriately modified in some manner. Apparently only HA strains and cultivars are capable of appropriately modifying OMP106 polypeptide so that it can mediate bacterial binding to hemagglutinin receptor on mammalian cell surfaces.

7. EXAMPLE

Efficacy of OMP106 Vaccine: Cytotoxic Activity of Anti-OMP106 Antiserum

Complement-mediated cytotoxic activity of anti-OMP106 antibodies was examined to determine the vaccine potential of OMP106 polypeptide. Antiserum to OMP106 polypeptide of a HA cultivar of ATCC® (American Type Culture Collection) 49143 was prepared as described in Section 6.1.8. supra. The activities of the pre-immune serum and the anti-OMP106 antiserum in mediating complement killing of *M. catarrhalis* were examined using the "Serum Bactericidal Test" described by Zollinger et al. (Immune Responses to *Neiserria meningitis*, in Manual of Clinical Laboratory Immunology, 3rd ed., pg 347-349), except that cells of HA and NHA *M. catarrhalis* strains or cultivars were used instead of *Neiserris meningitis* cells.

The results show that anti-OMP106 antiserum mediated complement-killing of a HA cultivar of heterologous *M. catarrhalis* ATCC® (American Type Culture Collection) 43627 but not a NHA cultivar of *M. catarrhalis* ATCC® (American Type Culture Collection) 43627 or the NHA *M. catarrhalis* ATCC® (American Type Culture Collection) 8176. Table 3 summarizes the complement mediated cytotoxic activities of pre-immune serum and anti-OMP106 antiserum against a HA cultivar of ATCC® (American Type Culture Collection) 43627.

TABLE 3

Complement mediated cytotoxic activities of pre-immune serum and anti-OMP106 antiserum

| | Cytotoxic Titer[1] | |
|---|---|---|
| | Pre-immune | Anti-OMP106 |
| Experiment 1 | 16 | 128 |
| Experiment 2 | 8 | 64 |

[1]The titer is in the highest dilution at which a serum can mediate complement killing of a HA cultivar of ATCC ® (American Type Culture Collection) 43627 (e.g., 16 represents a 16 fold dilution of the serum), the larger the number, the higher the cytotoxic activity or titer.

As shown in Table 3, the anti-OMP106 antiserum has 8 fold greater cytotoxic activity than the pre-immune serum. This finding indicates that OMP106 polypeptide is useful as a vaccine against HA *M. catarrhalis* strains and cultivars.

8. EXAMPLE

Isolation of the omp 106 Gene 8.1. Preparation of 72 bp Primer

Degenerate PCR primers were designed based on the OMP106 N-terminal sequence information, including the 40 amino acid sequence depicted in SEQ ID NO:11.

A subset of this sequence (shown below) comprising 24 amino acids (SEQ ID NO:12) was chosen for the design of the degenerate oligonucleotides MC 11 (SEQ ID NO:13) and MC 12 (SEQ ID NO: 14), the sequences of which are also shown below:

EADGGKGGANARGDKSIAIGDIAQ (SEQ ID NO:12)

MC 11: GAR GCN GAY GGN GGN AAR (512-fold degenerate) (SEQ ID NO: 13)

MC 12: YTG NGC DAT RTC NCC DAT (576-fold degenerate) (SEQ ID NO: 14).

These oligonucleotide primers were chosen to amplify an approximate 72 bp DNA fragment of *Moraxella catarrhalis* omp 106 gene from genomic DNA. The size of the fragment was chosen to facilitate isolation by conventional agarose DNA electrophoresis. There is comparable degeneracy among the primers, and the primers exclude sequences encoding serine, arginine or leucine.

8.2. PCR Amplification of a 72 BP DNA Fragment From *Moraxella Catarrhalis* Genomic DNA A 72 bp DNA fragment was amplified from 20 ng of *Moraxella catarrhalis* genomic DNA template using the degenerate oligonucleotides MC 11 (SEQ ID NO:13) and MC 12 (SEQ ID NO:14) (0.5 µM each) and 5 U of Taq polymerase using the following PCR program:
Hold 1: at 94° C. for 2 min.
Cycle (×30): Denature at 94° C. for 10 sec
  Anneal at 45° C. for 15 sec
  Elongate at 72° C. for 4 sec
Hold 2: at 72° C. for 1 min.

8.3. Isolation and Subcloning of the 72 BP PCR Amplification Product

The material from a 50 µl amplification assay was subjected to electrophoresis on a 2% TAE agarose gel and the 72 bp DNA fragment was excised and recovered from the solubilized gel using a QiaQuick column (Qiagen). The isolated 72 bp DNA fragment was cloned into the pCR-Script AmpSK (+) vector (Stratagene) following the kit manufacturer's protocol. A miniprep DNA was prepared using standard protocols. Insert bearing plasmids were identified by restriction digestion with Pvu II, which cuts on both sides of the plasmid polylinker. Plasmids containing the 72 bp insert exhibited a proportionate size increase when compared to the 448 bp Pvu II restriction fragment obtained from nonrecombinant plasmids.

8.4. Sequencing of the 72 Bp Insert in PCR Script AMP SK(+)

The preparation of DNA templates and all sequencing protocols were done as described by the manufacturer of the sequencing kit (USB). The sequencing reactions were run on a 6% Acrylamide-7 M urea-TBE gel, fixed, dried and exposed to Kodak X-OMAT AR 5 film at room temperature. The sequence determined from these experiments is shown below aligned with the encoded string of amino acids:

Glu Ala Asp Gly Gly Lys Gly Gly Ala Asn Ala Arg Gly Asp
  Lys GAA GCG GAC GGG GGG AAA GGC GGA GCC
  AAT GCG CGC GGT GAT AAA Ser Ile Ala Ile Gly Asp Ile
  Ala Gln (SEQ ID NO: 18)
TCC ATT GCT ATT GGT GAC ATT GCG CAA. (SEQ ID NO:17)

Thus, the amino acid sequence encoded by the cloned 72 bp DNA insert exactly matched the sequence obtained from the mature N-terminus of the OMP106 protein beginning at residue 6 of SEQ ID NO:11.

8.5. Generation of a Radiolabled 72 bp DNA Screening Probe

The sequence information shown above was used to design a pair of nondegenerate oligonucleotide primers, MC 17 (SEQ ID NO: 15) AND MC 18 (SEQ ID NO: 16), respectively, whose sequences are as follows:
MC 17: GAA GCG GAC GGG GGG AAA (SEQ ID NO:15)
MC 18: TTG CGC AAT GTC ACC AAT (SEQ ID NO:16)

PCR amplification of the 72 bp DNA fragment was performed under the same conditions as described above with the exception that the annealing temperature was raised to 50° C. The 72 bp DNA fragment was isolated from an agarose gel as before and radiolabeled using [32P]-γ-ATP and T4 polynucleotide kinase according to standard methods. Unincorporated radiolabel was separated from the probe on a G25 Sepharose spin column. Before use the probe was denatured for 2 min. at 95° C. and subsequently chilled on ice (4° C.).

8.6. Hybridization of Plaque-Lift and Southern Blots with Radiolabeled Probe

Phage plaques from library platings were immobilized on nylon filters using. established transfer protocols. Digested bacterial genomic DNA, phage or plasmid DNA was electrophoresed on 0.8% TAE-agarose gels and transfered onto nylon filters using a pressure blotter (Stratagene) according to the manufacturer's recommendations. Hybridizations with the 72 bp probe were performed at 50° C. Hybridizations with other probes were generally carried out at 60° C. Washes of increasing stringency were done at the respective hybridization temperatures until nonspecific background was minimized.

8.7. Construction of a *Moraxella Catarrhalis* Genomic DNA Library

A genomic library was constructed in the FIX II replacement vector obtained from Stratgene. The vector arms were digested with Xho I and partially filled-in by DNA polymerase (Klenow fragment) with dTTP and dCTP, resulting in 5' TC overhangs. Partial digests of *Moraxella catarrhalis* DNA by Sau 3A were performed to yield fragment sizes between 9 kb and 23 kb. The cleaved DNA was partially filled-in by DNA polymerase with dGTP and dATP, resulting in 5' GA overhangs. It will be obvious to those skilled in the art that neither partially filled-in vector arms nor inserts will be able to self-ligate whereas the partially filled-in vector and the partially filled-in inserts will ligate. Ligations of vector arms and insert DNA were carried out according to standard protocols. Ligation reactions were packaged in vitro using the Stratagene GigaPack Gold III extract. The packaged phage were plated on *E. coli* XI blue MRA (P2) (Stratagene) to further suppress nonrecombinants. The initial library titer was determined to be approximately $2 \times 10^5$ pfu.

The library was screened using $4 \times 10^4$ pfu that were plated at a density of $8 \times 10^3$ pfu/130 mm plate. Several putative positive phage plaques were located and the six strongest hybridizing phage, omp106.1 to omp106.6, respectively, were eluted from cored agarose plugs, titered and replated for secondary screening. After the second screening only, omp106.3, omp106.5, and omp106.6, respectively, turned out to be true positives. These phage were replated at low density (approximately 100 pfu/plate) and three plaques per plate were analyzed by PCR using the primer pair MC17 (SEQ ID NO:15) and MC18 (SEQ ID NO:16) as described. The DNA amplification products from each of the three phage exactly matched the size of the 72 bp PCR fragment obtained from genomic Moraxella catarrhalis DNA.

8.8. Large Scale Phage Dna Isolation

One liter cultures of bacteria infected with individual phage eluates were grown for about 6 hrs at which time lysis occurred. The lysates were processed according to standard procedures. Crude phage preparations were purified by banding in CsCl, digested with Proteinase K, extracted with a 1:1 (v/v) mixture of phenol and chloroform and precipitated with 2 volumes of ethanol after adjusting the DNA solution to 0.3 M NaOAc (pH 7.8) all according to protocols well known to those skilled in the art.

8.9. Determination of Insert Size and Mapping of DNA Fragments Hybridizing with the 72 bp Probe In order to estimate the size of the inserts in omp106.3, omp106.5, and omp106.6, phage DNA was digested with NotI and the digests were analyzed on a 0.5% TAE-agarose gel side by side with suitable DNA markers. The approximate sizes of the inserts were 11 kb, 15 kb and 20 kb for omp106.3, omp106.5, and omp106.6, respectively. In order to map restriction fragments that would hybridize to the 72 bp probe, DNA from each phage isolate was digested with a number of common restriction enzymes either alone or in combination with NotI. The rationale of this approach was to discriminate between fragments that span the insert/phage arm junction and those that map on the NotI insert. The series of single and double digests were run side-by-side for each phage isolate and analyzed by Southern analysis with radiolabeled 72 bp probe. These mapping experiments showed that the NotI insert of phage omp106.6 contained the largest contiguous hybridizing restriction fragments of all phage. Two of these fragments, a NotI/PstI fragment 5.5 kb and a HindIII fragment having an approximate size of 12 kb, respectively, were chosen for further analysis because they appeared to be large enough to harbor either the entire coding region for OMP106 or the majority thereof.

8.10. Mapping of the 72 bp DNA Region in the Subcloned NotI/PstI Fragment of omp106.6

The NotI/PstI fragment was excised from omp106.6 phage DNA, isolated from a 0.8% TAE-agarose gel and subcloned into the polylinker sites of pBluescript II SK to yield the recombinant plasmid p omp N/P. Bacteria harboring this plasmid grew unusually slowly and tended to delete and rearrange part of the insert, even more so when grown for large scale plasmid DNA preps. Since this region contained sequences coding for the amino terminus of OMP106, it was likely that it would also carry regulatory upstream elements that were potentially active and/or detrimental to the maintenance of the plasmid in *E. coli*. Likewise, leaky transcription from the plasmid lacZ promoter could have led to expression of *Moraxella* sequences that were toxic for *E. coli*. A coarse restriction mapping was performed using enzymes that cut in the plasmid polylinker. This analysis showed that the insert had a ClaI restriction site approximately 1.5 kb upstream from the PstI site. Likewise, at least two HindIII restriction sites mapped approximately 2.8 kb and approximately 3.5 kb upstream from the PstI site.

Next, the location of the 72 bp DNA fragment within the 5.5 kb NotI/PstI fragment was elucidated using a PCR-based mapping approach employing the ScreenTest Screening Kit (Stratagene). This kit enables the user to determine the orientation of an insert by amplifying the DNA sequences between an insert-resident primer site and one that lies outside the plasmid's multiple cloning site.

The kit oligonucleotide P1 (TCATCATTGGAAAACGT-TCTTCGGGGCGAA) SEQ ID NO:19 hybridizes approximately 1 kb away from the multiple cloning site of p omp N/P. The size of a PCR product obtained with the oligonucleotides P1 and MC 17 (SEQ ID NO:15) was approximately 1.5 kb. It was hence deduced that the 72 bp fragment maps at approximately 450 bp upstream from the PstI site. It was also evident from this information that the major part of the OMP106 protein was encoded by sequences located beyond the PstI site. By the same token, there was ample sequence upstream from the 72 bp region to encode a presumptive signal sequence and promoter/regulatory elements to drive transcription of this gene in *Moraxella catarrhalis*.

8.11. Mapping of the 12 kb Hindiii Insert from Omp 106.6

The 12 kb HindIII fragment of omp106.6 was excised from phage DNA, separated on a 0.8% TAE-agarose gel and recovered as described above. The isolated DNA fragment was further digested with a number of common restriction endonucleases. Digestion with EcoRI cut the HindIII fragment into two 6 kb fragments, whereas digestion with PstI yielded restriction fragments of approximately 3 kb and approximately 9 kb.

Based on the hybridization data with the 72 bp DNA probe, the mapping of a HindIII site approximately 3 kb upstream of the PstI site in p omp N/P and the mapping of a PstI site at a distance of approximately 3 kb from one HindIII site in the 12 kb HindIII fragment, it was hypothesized that the 5.5 kb NotI/PstI fragment and the 12 kb HindIII fragment of phage omp106.6 might overlap in the 3 kb DNA sequence between HindIII and PstI. In view of the potential coding capacity of the 12 kb HindIII fragment, it was concluded that this fragment would have enough sequence information to encode the open reading frame of OMP106.

8.12. Subcloning of Restriction Fragments of Omp106.6 and Analysis of Recombinant Plasmids The ClaI/PstI restriction fragment from p omp N/P was subcloned into the respective polylinker sites of pBluescript II SK to yield the plasmid p omp C/P. The mixture of HindIII/EcoRI fragments obtained by EcoRI digestion of the 12 kb HindIII fragment was cloned into ZAP Express arms obtained by double digestion with EcoRI and HindIII. The phage/insert ligations were packaged as described above and plated on a lawn of *E. coli* XL blue MRF' cells (Stratagene). Recombinant phage were converted into insert bearing phagemids using the coinfection protocol with ExAssist helper phage and the *E. coli* XLOLR strain provided with the kit (Stratagene). The resulting phagemids were screened for the presence of EcoR/HindIII inserts of approximately 6 kb. Furthermore, diagnostic digestions with PstI were performed to distinguish between clones having the promoter-proximal HindIII/EcoRI fragment and those carrying the promoter-distal EcoRI/HindIII fragment. Invariably, in a large number of analyzed phagemids, the cloned insert did not cut with PstI. It was concluded that the insert having an approximate size of 6 kb was the promoter-distal EcoRI/HindIII fragment of omp106.6. The resulting phagemid was designated as pBK omp R/H. Physical mapping of this phagemid located a unique XbaI site approximately 1.5 kb upstream from the HindIII site. Sequences between this XbaI site and the XbaI site in the polylinker were deleted and the recircularized phagemid was designated as pBK omp R/X. On the basis of information described above herein it was calculated that the EcoRI/XbaI restriction fragment had ample sequence information to encode the C-terminal half of OMP106.

Figure 11:
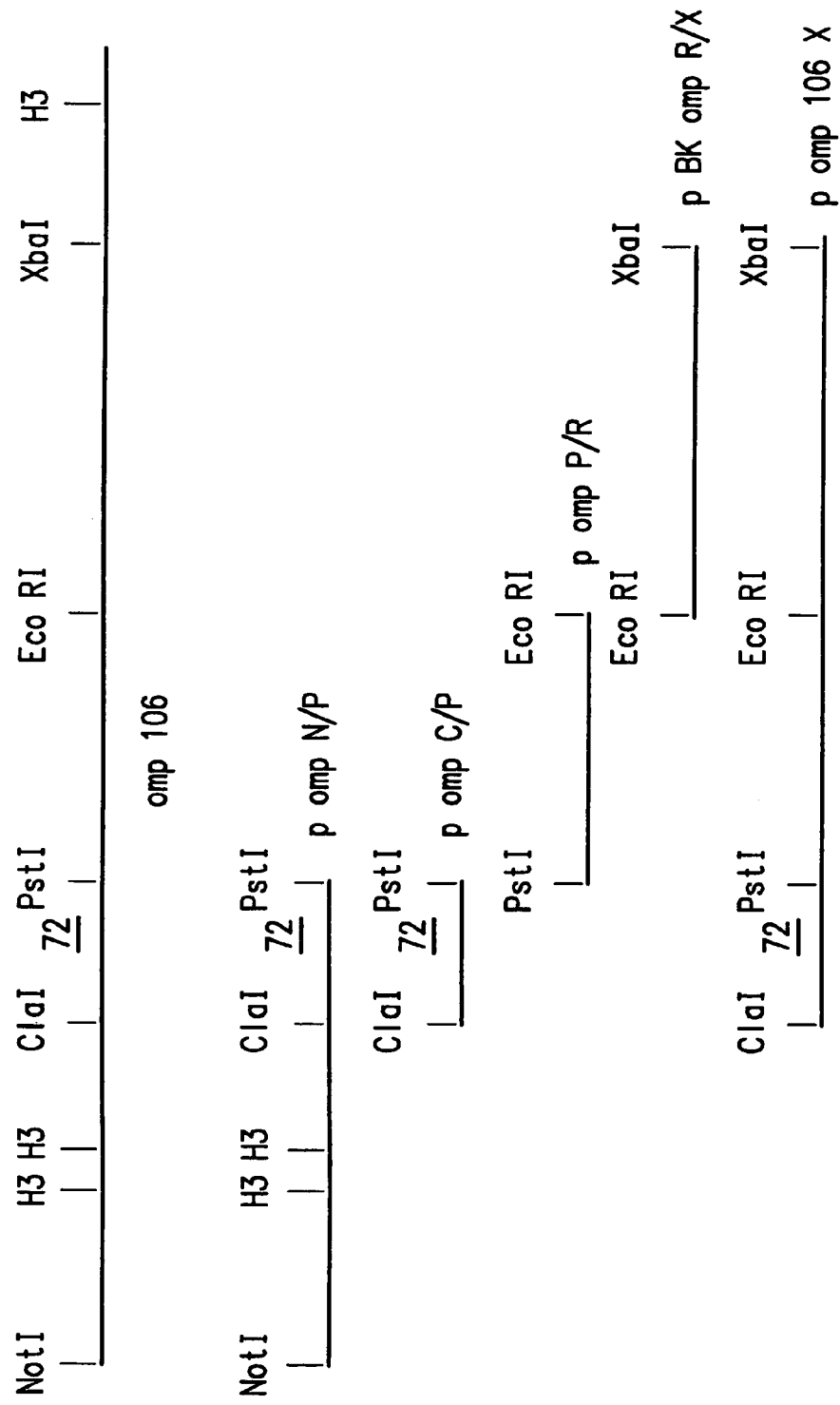

Finally, the missing sequences between the PstI site and the EcoRI were generated by long distance PCR (Barnes, W. M., 1994, Proc. Natl. Acad. Sci. USA 91:2216 2220) using genomic DNA or phageλ omp 106.6 DNA as the template. The primers for this experiment were MC 17 (SEQ ID NO: 15) and a gene-specific primer, omp R/X a1 (CGG TCA GCT TAG GCG TGG TT) (SEQ ID NO:20) which was designed based on sequence information downstream from the EcoRI site in pBK omp R/X. The PCR product having an approximate size of 3.5 kb was digested with PstI and EcoRI and the approximately 3 kb fragment was gel-isolated and cloned into PstI/EcoRI digested pBluescript II SK. The resulting recombinant plasmid was designated as p omp P/R. A map of the omp106 locus, including fragments subcloned and used in various constructs, is shown in FIG. 11. Construction of the plasmids illustrated in FIG. 11 is described herein below in Section 9.

9. EXAMPLE

Sequencing of the omp 106 Gene

Sequencing of the omp 106 gene was performed using the plasmids p omp C/P, pBK omp R/X and p omp P/R as a template. Initially, commercially available T3 and T7 promoter primers flanking the multiple cloning site in these plasmids were used as sequencing primers. Nested deletions of these plasmids were generated using the Exo Mung Bean Deletion kit purchased from Stratagene following the manufacturer's protocol. Gene specific primers were designed on the basis of the sequence data as needed.

Secondary confirmation of the sequences was obtained using a series of gene-specific primers and omp 106.6 phage DNA and PCR fragments amplified from *Moraxella catarrhalis* genomic DNA as the sequencing template. PCR fragments for this application were generated using the Advantage genomic PCR kit from Clontech which contains a mix of high fidelity/proofreading polymerases. Sequencing from these templates was done to rule out potential cloning artifacts incurred during the genetic manipulations. All sequencing reactions were performed using the Dye Terminator Cycle Sequencing Kit from Perkin-Elmer according to the manufacturer's specifications. The sequencing reactions were read using an ABI Prism 310 Genetic Analyzer. The sequences were aligned using the AutoAssembler software (Perkin-Elmer) provided with the ABI Prism 310 sequencer.

The EcoRI/XbaI fragment of omp 106 was released from pBK omp R/X as a 4 kb NotI/BamHI fragment (by use of polylinker sites) and subcloned into p omp C/P that had been digested with the same enzymes. The p omp C/P/RIX intermediate was then digested with PstI and EcoRI to receive the omp 106 PstI/EcoRI fragment that had been isolated from p omp P/R. This construct, designated p omp 106x, contains the entire open reading frame of *Moraxella* cattarrhalis OMP106 protein. The approximate size of the insert is 8.5 kb. This plasmid was inserted into *E. coli* Top10 (Invitrogen) and deposited with American Type Culture Collection (ATCC®) as *E. coli* Top10 (POMP106).

The nucleotide sequence of the entire omp 106 gene is shown in SEQ ID NO:8. A deduced amino acid sequence of the open reading frame of omp 106 is shown in SEQ ID NO:9.

10. EXAMPLE

Verification of the Omp 106 Gene 10.1. Construction of an Omp 106 Gene-Targeting Cassette A gene targeting cassette was assembled from various omp 106 subclones (described above): p omp C/P, omp P/R, pBK omp R/X and a Kanamycin Resistance GenBlock purchased from Pharmacia. P omp 106x, was linearized with PstI and used to clone the Kanamycin resistance gene as a PstI fragment. Depending on the orientation of the kanamycin insert (determined by cutting an asymetric ClaI site in the KanR gene block), the resulting constructs were designated as P ompxKO (the kanamycin and omp 106 genes are transcribed in the same direction) or p ompxOK (kanamycin and omp 106 gene transcription proceed towards each other). Highly purified DNA of both constructs was prepared using standard protocols.

10.2. Preparation of Electrocompetent *Moraxella Catarrhalis* Cells

*Moraxella catarrhalis* cells were grown to an optical density (OD600 nm) of 1, harvested by centrifugation (3000×g), and subsequently washed twice in ice-cold distilled water and once in 15% glycerol. The final cell pellet was resuspended in 1 2 ml of 15% glycerol and rapidly frozen in 100 μl aliquots on dry ice. The electrocompetent cells were stored at −80° C.

10.3. Electroporation of Competent Cells

Aliquots (50 μl) of electrocompetent cells were mixed with 1 μg of plasmid DNA, transferred to a 0.1 cm electroporation cuvette and kept on ice for 1 min. An electroporation pulse was subsequently delivered using the following settings: 1500 V, 50 μF and 150'Ω. The pulsed culture was immediately transferred to Mueller-Hinton medium and incubated for 6 hrs at 37° C. Aliquots of the culture were then spread on selective media plates (Mueller-Hinton with 5 μg/ml of Kanamycin) and incubated at 37° C. until colonies were clearly visible (24-36 hrs). A random sample of bacteria was picked and restreaked to obtain single colonies. Individual colonies were grown in 2 ml cultures as above and used to prepare genomic DNA for PCR analysis.

11. EXAMPLE

Genetic Analysis 11.1. PCR Analysis

Figure 12A:
Figure 12B:
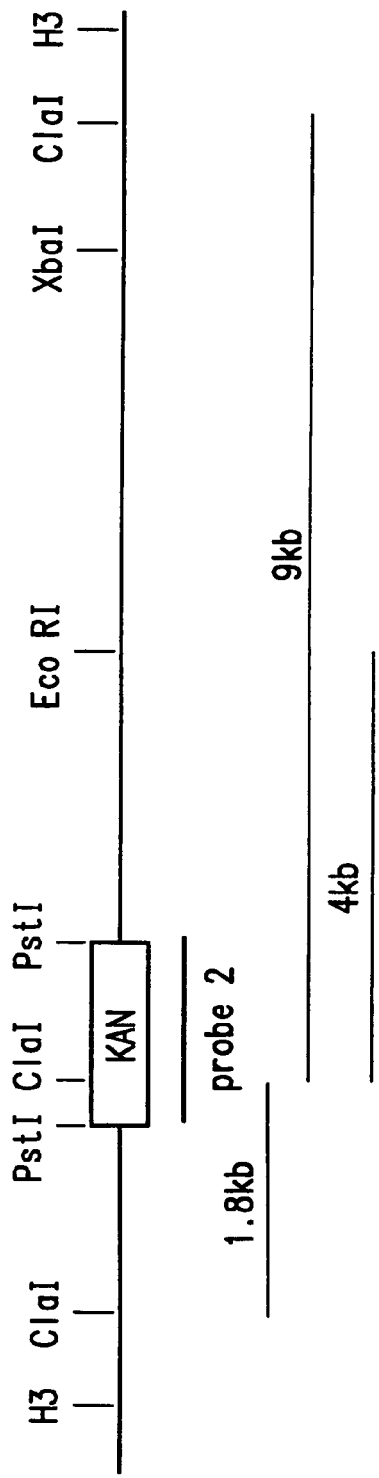

DNA from KAN$^R$ *Moraxella catarrhalis* colonies was analyzed by PCR using a forward primer that hybridizes upstream from the ClaI restriction site (i.e. outside the sequences used in the targeting construct) and a reverse primer located in the coding region of the kanamycin gene. A PCR product is only to be expected if the incoming targeting cassette has been integrated into the genome by homologous recombination. No amplification product was obtained with wild-type DNA, whereas 100% of the DNA of KAN$^R$ colonies yielded an amplification product of the predicted size. The amplification products span the PstI restriction site into which the kanamycin marker was cloned. Digestion of the amplification products with PstI yielded fragments of the predicted size. A map of omp 106 and deletion mutants thereof is shown in FIG. 12.

11.2. Southern Analysis of Omp 106

Genomic DNA from wild-type Moraxella catarrhalis and from PCR positive deletion mutants was digested with ClaI and ClaI/EcoRI. The digests were separated on a 0.8% TAE-agarose gel and transferred to nylon membranes using standard protocols. The blots were hybridized with $^{32}$p labeled probes prepared from either the omp 106 ClaI/PstI region or from the Kanamycin resistance gene. Using the omp 106 ClaI/PstI probe, fragments having approximate sizes of 9 kb and 4.6 kb were detected in the ClaI and ClaI/EcoRI digests, respectively, on DNA from all wild-type strains tested, whereas a unique DNA fragment having an approximate size of 1.8 kb is detected in both digests on DNA from the deletion mutants. The presence of this unique, new restriction fragment demonstrates the successful targeting of the omp 106 locus.

As expected, probing of the membrane with the kanamycin gene did not generate any signal in *Moraxella catarrhalis* wild-type DNA. In DNA from the deletion mutants, the kanamycin probe detected fragments having approximate sizes of 9 kb and 1.8 kb and 4 kb and 1.8 kb in the ClaI and ClaI/EcoRI digests, respectively. As before, the presence of these sequences in the deletion mutants and their absence in the wild-type DNA demonstrate that the omp 106 locus has been successfully altered.

12. EXAMPLE

Generation and Reactivity of Monoclonal Anti-OMP106 Antibodies

BALB/c mice were immunized with total outer membranes from *M. catarrhalis*. Hybridomas for monoclonal antibodies were prepared by fusing the spleen cells from these mice to SP2/0 cells and selecting for successful hybrids with HAT containing media. Reactive hybridomas were screened using an ELISA containing detergent extracts of the total outer member of *M. catarrhalis* MC2926. From this screen, 12 hybridomas with varying levels of activity in the ELISA were selected for clonal selection, the monoclonal antibodies were assayed for reactivity to purified OMP106 and total outer membranes from *M. catarrhalis* MC2926ΔOMP106 by ELISA. Monoclonal antibodies designated SRB #1 and SRB #3 both reacted specifically to OMP106 in the ELISA.

Figure 10:
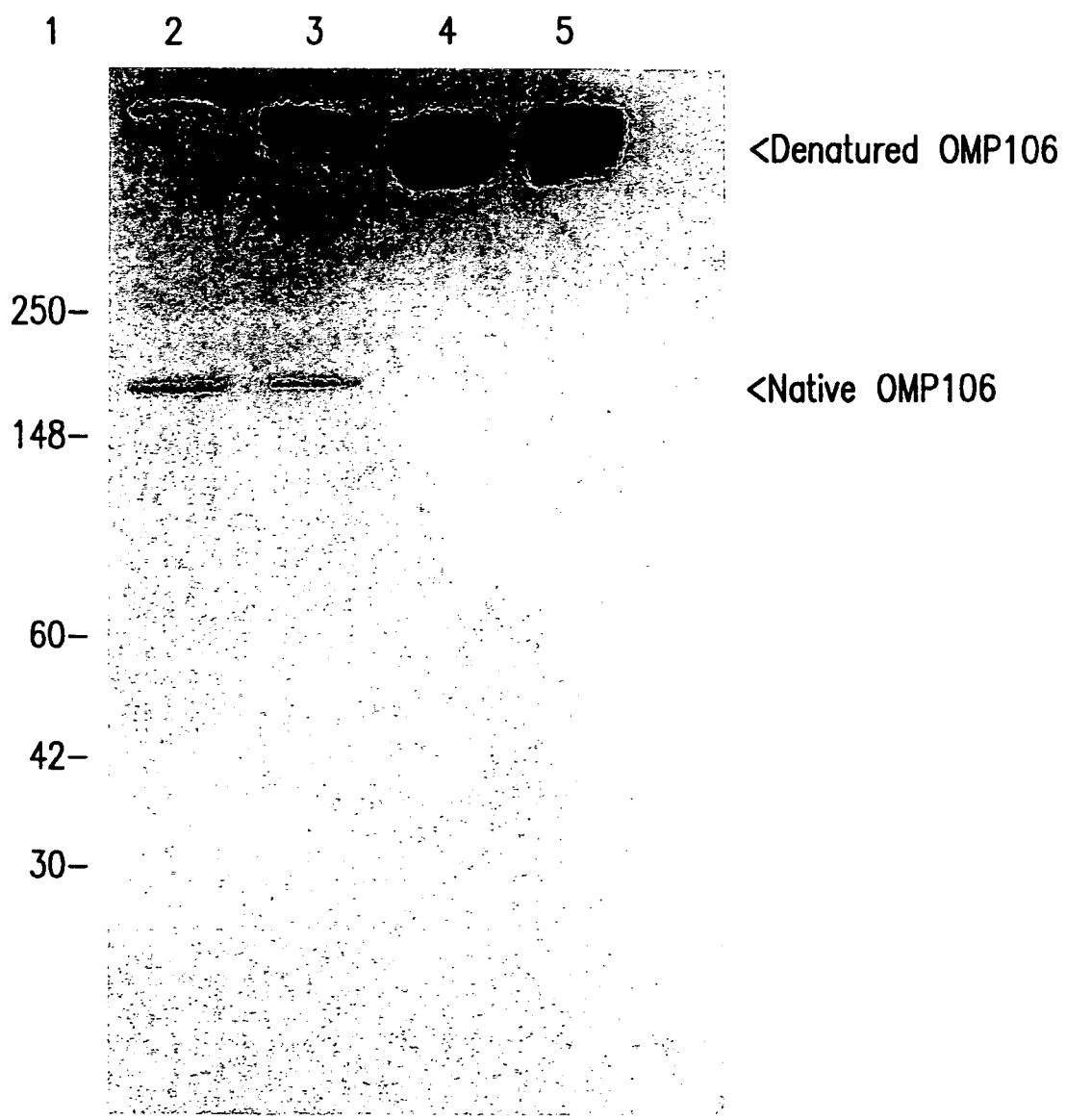

Western blots were performed as described in Example 6.1.9, using monoclonal antibodies SRB #1 and #3. SRB #1 demonstrated reactivity to OMP106 in Western blots to both the nondenatured form of the protein (greater than 250 kDa) and to the denatured form of the protein (approximately 190 kDa) produced by incubating the sample at 100° C. for 5 minutes prior to resolving on the polyacrylamide gel (FIG. 10), which suggests that SRB #1 is reacting with a linear epitope from OMP106. SRB #3 did not react with OMP106 in the Western, regardless of the form of the protein, but as noted above, did react in an ELISA. This indicates that SRB #3 reacts with a native conformation of OMP106 that is not presented in the Western blots.

13. EXAMPLE

Binding and Inhibition of Binding to Nasopharyngeal Cells 13.1. Nasopharyngeal Cell Binding The binding of *Moraxella* to the continuous cell line Hep-2 was assayed using a modification of the procedure described by Galan and Curtiss (J. E. Galan and R. Curtiss III. 1989, Proc. Natl Acad. Sci. USA 86:6383-6387, incorporated herein by reference in its entirety). The *M. catarrhalis* strain MC2926 and MC2926ΔOMP106 were used to assay the binding of *Moraxella* to Hep-2 cells. The MC2926ΔOMP106 strain is an isogeneic strain to MC2926 but with the gene for OMP106 disrupted (as described in Example 8 above), thereby causing the loss of the expression of the OMP106 protein.

Briefly, the strains were grown to mid-log phase in Mueller Hinton broth. Bacterial cells from the culture were then centrifuged onto the monolayer of Hep-2 cells and allowed to bind to the cells for 1 hour. Nonbound cells were removed by washing with Hanks balanced salt solution containing calcium. Adherent cells were removed with the monolayer by treatment with 0.1% sodium glycocholate in phosphate buffered saline (PBS). The number of adherent cells were enumerated by plating on Mueller Hinton agar and allowing the bacteria to grow for 24 hours. The efficiency of binding of the bacteria is expressed as a percentage of bacteria bound relative to the original number of bacteria added to the Hep-2 monolayer, and is shown in Table 4 below.

TABLE 4

Binding efficiency of MC2926 and the genetic deletion of omp 106 (MC2926ΔOMP106) to HEp-2 cells.

| Bacterial strain | % bound |
| --- | --- |
| MC2926 | 100% |
| MC2926ΔOMP106 | 21% |

The results of the nasopharyngeal cell binding assay shows that OMP106 is responsible for binding and adherence of *Moraxella catarrhalis* to nasopharyngeal cells.

13.2. Inhibition of Nasopharyngeal Binding

The hybridoma culture supernatants from Example 9 were used to treat bacterial cells to assay for their ability to block binding of the *Moraxella* bacteria to nasopharyngeal cells (HEp-2) by incubating the bacteria with monoclonal antibody for 5 minutes prior to exposing the bacteria to the HEp-2 cells.

The data from this experiment indicates that one of the monoclonals (SRB #3) blocked the bacteria from binding to nasopharyngeal cells (Table 5). This data, when considered with the data from the strain with the genetic deletion of OMP106 (MC2926ΔOMP106) (Table 4), supports the conclusion that SRB #3 binds to a native conformation of OMP106. Furthermore, this demonstrates that SRB #3 can neutralize the biological activity of OMP106 (i.e., binding to eukaryotic cells). The observation that only one hybridoma blocked the binding to nasopharyngeal cells, while the other did not rules out the possibility that media components are responsible for the inhibition of binding.

TABLE 5

Antibody mediated inhibition of MC2926 binding to Hep-2 cells

| Treatment of bacterial cells | % bound |
| --- | --- |
| Tissue culture media | 98% |
| Hybridoma SRB #1 | 100% |
| Hybrid -continued <223> OTHER INFORMATION: n is a, c, g, or t

<400> SEQUENCE: 3
ggnacngtnc tnggnggnaa raar                                           24

<210> SEQ ID NO 4
<211> LENGTH: 72
<212> TYPE: DNA
<213> ORGANISM: Moraxella catarrhalis

<400> SEQUENCE: 4
gaagcggacg gggggaaagg cggagccaat gcgcgcggtg ataaatccat tgctattggt    60
gacattgcgc aa                                                        72

<210> SEQ ID NO 5
<211> LENGTH: 24
<212> TYPE: PRT
<213> ORGANISM: Moraxella catarrhalis

<400> SEQUENCE: 5

Glu Ala Asp Gly Gly Lys Gly Gly Ala Asn Ala Arg Gly Asp Lys Ser
1               5                   10                  15

Ile Ala Ile Gly Asp Ile Ala Gln
            20

<210> SEQ ID NO 6
<211> LENGTH: 24
<212> TYPE: DNA
<213> ORGANISM: Artificial Sequence
<220> FEATURE:
<223> OTHER INFORMATION: oligonucleotide PCR primer
<220> FEATURE:
<221> NAME/KEY: misc_feature
<222> LOCATION: (1)..(24)
<223> OTHER INFORMATION: n is a, c, g or t

<400> SEQUENCE: 6
yttyttnccn ccnagnacng tncc                                           24

<210> SEQ ID NO 7
<211> LENGTH: 24
<212> TYPE: DNA
<213> ORGANISM: Artificial Sequence
<220> FEATURE:
<223> OTHER INFORMATION: oligonucleotide PCR primer
<220> FEATURE:
<221> NAME/KEY: misc_feature
<222> LOCATION: (1)..(24)
<223> OTHER INFORMATION: n is a, c, g or t

<400> SEQUENCE: 7
ggnacngtnt trggnggnaa raar                                           24

<210> SEQ ID NO 8
<211> LENGTH: 9542
<212> TYPE: DNA
<213> ORGANISM: Moraxella catarrhalis

<400> SEQUENCE: 8
ctattgactt aaatcaccat atggttataa tttagcataa tggtaggctt tttgtaaaaa    60
tcacatcgca atattgtttt actgttacta ccatgcttga atgacgatcc aaatcaccag   120
attcattcaa gtgatgtgtt tgtatacgca ccatttaccc taattatttc aatcaaatgc   180
ctatgtcagc atgtatcatt ttttaaggta aaccaccatg aatcacatct ataaagtcat   240

-continued

```
ctttaacaaa gccacaggca catttatggc cgtggcggaa tatgccaaat cccacagcac    300
ggggggggt  agctgtgcta cagggcaagt tggcagtgta cgcactctga gctttgcccg    360
tattgccgcg ctcgctgtcc tcgtgatcgg tgcgacgctc aatggcagtg cttatgcagg    420
tatcggaatt agtgaagcag acggggggaaa aggcggagcc aatgcgcgcg gtgataaatc   480
cattgctatt ggtgatattg ctcaggcact tggctctcaa tctattgcta tcggtgacaa    540
caaaatagtt cataattcaa ataataatgc taatataggt gccaaagcct caggtaatga   600
gtccatcgcc atcggtggtg atgtattggc ttctggtcat gcctcgattg ccatcggtag    660
tgatgactta tatttgaaaa aggaaacggt acagcaaatc tcagagcttc tacctattat    720
tcgcggacag aaagcattaa acgatatata ccaactagct gacactaatc ttcaaaaata    780
tagacgcaca cacgcacagg gacacgccag tactgcagtg ggagccatgt catatgcaaa    840
gggtcatttt tccaacgcct ttggtacacg ggcaacagct gaaggtacct attccttggc    900
agtgggtctt accgccacag ccaaagcagc atcttcaatc gctgttggtt ctaatgcaca    960
agctatcggg tttgcagcga cagccgttgg tggaagtact caagttaatt tgaatcgagg   1020
tattgcccta ggttttggtt ctcaggtcct tcagaaggat aatgatgtaa atgcagcaaa   1080
tgtacgggcc tatgcaccag atgataacca gccaatagac aaccggtata agccaccttt   1140
caagaatggt gctacggatg tattttccat tggtaatagt aatgggaatg acagtatcag   1200
gcgtaaaatc atcaatgtcg gtgcaggttc tgcggatacc gatgcggtca atgtggcaca   1260
gcttaaagag gcggtgaggc tggctaatcg tcaaattact tttaagggtg atgatagcaa   1320
taatagagta gaaaaaggtt tgggcaagac tttaactatc acaggtggtg cacagaccag   1380
cgcattaacc gatcataaca tcggtgtggt acaaaatggc gatggtctga agttcaact   1440
tgctgaaact ttaaccagcc ttaaaatggt taccactgaa aacctaaccg ccaacgagaa   1500
agttaccgta ggcaaaaccc gccttaccac agataaaatt ggttttacca atgatatgaa   1560
tggcattgat gaaagcaaac cttatcttga taaagacact ggcattcatg caggtggtca   1620
aaagattacc aaaacttactg ctggtgtagt agatgacgat gcggcaactt atggacagct   1680
taaaaaagtt aaccaaaccg ctgaaagtgc tctacaaacc tttaccgtta aaaaggtaga   1740
taaaaatggt aatgatgcta atgacagcaa aatcatcacc gtgggtaaaa ataacaaacc   1800
agacggtact caagtcaaca ccctaaaact caaaggtgaa aacggtgttg atgttacaac   1860
cgaaacaaat ggtacagtta cctttgggct taaccaaaat aacggtctga ccgttggcaa   1920
cagcacccta acaacgatg gcttatctgt taaaaacacc aatagtaaca aacaaatcca   1980
agtcggtgct gatggcatta catttactga tatcagcaat agtaagccag gtgctggcat   2040
tgaaaatacc actcgcatta ccagagacgg tattggtttt gctaataata ctggttcatt   2100
ggatgcaaac aaaccccgcc taaccccaac tggcattaac gcaggtggta agagctgac   2160
caatgtccaa tctgccatta accctgctac caatggtggg cagctagact ttatgaaccg   2220
cctaagcact gctaataccg aaaaatcagg ctctgccgcc accattaaag acttatacaa   2280
cctatcacaa gtaccgctga cctttgcagg tgatacaggt cctaatgtca ccaaaaaact   2340
gggcgagatt ttaaaggtta aaggtggtaa accacagct gatgatttaa ccaaaaataa   2400
catcggtgtg gtggctgata gtaccgataa tagcttaacc gttaaacttg ctaaaacttt   2460
aagcgatctt gatgcggtta atactaaaac cctaactgcc agcgataaag ttaccgtaga   2520
cagtggcaac aacaccgcta agctacaaaa tggtgattta acctttagca aacaaatac    2580
```

```
aggtgctacc cctgccacca acagcaaaac catctatggc gttgatggct tgaagtttac   2640
tgataacaat ggtatagcac ttgacggcac aacttacatc accaaagaca aagttggctt   2700
tgctaagcaa gatggttcac ttgataaaag caaaccttat cttgataagg acaagctaaa   2760
agtgggtgaa gttgagatta ccaccaacgg cattaatgca ggtggtaaag ccatcacagg   2820
actaagcaat accctaaccg atgccaccaa cgcaacaaca gggcatgtaa ctcaattggg   2880
tatcgttgat agtactgaca aacccgtgc cgccagcatt ggtgatgtgc taaacgcagg   2940 cttttaaccta aaaataatg gtgacgccaa agactttgtc tccacttatg acactgttga   3000
ttttatcaat ggcaatgcca ccaccgctaa agtcacttat gatggcaaag ccagtaaagt   3060
ggcgtatgat gtcaatgtgg atggtacaac cattcatcta acaggcgctg atggcaataa   3120
aaaccaaatt ggcgtaaaaa ccaccacact gaccaaaaca gatgctaaag gtgataaagc   3180
aattaacttt agtgttaact ctggtgatga caaagccctt attaacgcca aagacatcgc   3240
cgacaatcta aacaccctag ctggtgaaat tcgcaacacc aaaggcacag cagacaccgc   3300
cctacaaacc tttcaagtca aaaagtcaa agaaatggt gatgatgata atgacgctga   3360
caccatcacc gtgggtaaag atgcaaaaac caatcaagtc aacaccctaa aactcaaagg   3420
taaaaacggt cttgatattc aaaccaataa agatggtacg gttacctttg cattaacac   3480 ccaaagcggt cttaaagccg gcaacaacac cactctaaac aacaatggct tgtctattaa   3540
aaacaccgct ggtaacgaac aaatccaagt cggtgctgat ggcgtgaagt tgccaaggt   3600 taataatggt gttgtaggtg ctggcattga tggcacaact cgcattacca gagatgaaat   3660
tggctttgct gggactaatg gctcacttga taaaagcaaa ccccacctaa gcaaagacgg   3720
cattaacgca ggtggtaaaa agattaccaa cattcaatca ggtgagattg cccaaaacag   3780
caatgatgct gtgacaggcg gcaagattta tgatttaaaa accgaacttg aaaacaaaat   3840
cagcagtact gccaaaacag cacaaaactc attacacgaa ttctcagtag cagatgaaca   3900
aggtaataac tttacggtta gtaaccctta ctccagttat gacacctcaa agacctctga   3960
tgtcatcacc tttgcaggtg aaaacggcat taccaccaag gtaaataaag gtgtggtgcg   4020
tgtgggcatt gaccaaacca aaggcttaac cacgcctaag ctgaccgtgg gtaataataa   4080
tggcaaaggc attgtcattg acagccaaaa tggtcaaaat accatcacag gactaagcaa   4140
cactctagct aatgttacca atgataaagg tagcgtacgc accacagaac agggcaagat   4200
aatcaaagac gaagacaaaa cccgtgccgc cagcattgtt gatgtgctaa gcgcaggctt   4260
taacttgcaa ggcaatggtg aagcggttga ctttgtctcc acttatgaca ctgtcaactt   4320
tgccgatggc aatgccacca ccgctaaggt gacctatgat gacacaagca aaaccagtaa   4380
agtggtctat gatgtcaatg tggatgatac aaccattgaa gttaaagata aaaaacttgg   4440
cgtaaaaacc accacattga ccagtactgg cacaggtgct aataaatttg ccctaagcaa   4500
tcaagctact ggcgatgcgc ttgtcaaggc cagtgatatc gttgctcatc taaacaccctt   4560 atctggcgac atccaaactg ccaaggggc aagccaagcg aacagctcag caggctatgt   4620
ggatgctgat ggcaataagg tcatctatga cagtaccgat aacaagtact atcaagccaa   4680
aaatgatggc acagttgata aaaccaaaga agttgccaaa gacaaactgg tcgcccaagc   4740 ccaaaccca gatggcacat ggctcaaat gaatgtcaaa tcagtcatta acaaagaaca   4800
agtaaatgat gccaataaaa agcaaggcat caatgaagac aacgcctttg ttaaaggact   4860
tgaaaaagcc gcttctgata acaaaaccaa aaacgccgca gtaactgtgg gtgatttaaa   4920
tgccgttgcc caaacaccgc tgacctttgc aggggataca ggcacaacgg ctaaaaaact   4980
```

-continued

```
gggcgagact tgaccatca aaggtgggca aacagacacc aataagctaa ccgataataa    5040
catcggtgtg gtagcaggta ctgatggctt cactgtcaaa cttgccaaag acctaaccaa    5100
tcttaacagc gttaatgcag gtggtaccaa aattgatgac aaaggcgtgt cttttgtaga    5160
ctcaagcggt caagccaaag caaacacccc tgtgctaagt gccaatgggc tggacctggg    5220
tggcaaggtc atcagcaatg tgggcaaagg cacaaaagac accgacgctg ccaatgtaca    5280
acagttaaac gaagtacgca acttgttggg tcttggtaat gctggtaatg ataacgctga    5340
cggcaatcag gtaaacattg ccgacatcaa aaaagaccca aattcaggtt catcatctaa    5400
ccgcactgtc atcaaagcag gcacggtact tggcggtaaa ggtaataacg ataccgaaaa    5460
acttgccact ggtggtgtac aagtgggcgt ggataaagac ggcaacgcta acggcgattt    5520
aagcaatgtt tgggtcaaaa cccaaaaaga tggcagcaaa aaagccctgc tcgccactta    5580
taacgccgca ggtcagacca actatttgac caacaacccc gcagaagcca ttgacagaat    5640
aaatgaacaa ggtatccgct tcttccatgt caacgatggc aatcaagagc ctgtggtaca    5700
agggcgtaac ggcattgact caagtgcctc aggcaagcac tcagtggcga taggtttcca    5760
ggccaaggca gatggtgaag ccgccgttgc cataggcaga caaacccaag caggcaacca    5820
atccatcgcc atcggtgata acgcacaagc cacaggcgat caatccatcg ccatcggtac    5880
aggcaatgtg gtagcaggta agcactctgg tgccatcggc gacccaagca ctgttaaggc    5940
tgataacagt tacagtgtgg gtaataacaa ccagtttacc gatgccactc aaaccgatgt    6000
ctttggtgtg ggcaataaca tcaccgtgac cgaaagtaac tcggttgcct taggttcaaa    6060
ctctgccatc agtgcaggca cacgcagg cacacaagcc aaaaaatctg acggcacagc    6120
aggtacaacc accacagcag gtgcaaccgg tacggttaaa ggctttgctg acaaacggc    6180
ggttggtgcg gtctccgtgg gtgcctcagg tgctgaacgc cgtatccaaa atgtggcagc    6240
aggtgaggtc agtgccacca gcaccgatgc ggtcaatggt agccagttgt acaaagccac    6300
ccaaggcatt gccaacgcaa ccaatgagct tgaccatcgt atccaccaaa acgaaaataa    6360
agccaatgca gggatttcat cagcgatggc gatggcgtcc atgccacaag cctacattcc    6420
tggcagatcc atggttaccg ggggtattgc cacccacaac ggtcaaggtg cggtggcagt    6480
gggactgtcg aagctgtcgg ataatggtca atgggtattt aaaatcaatg gttcagccga    6540
tacccaaggc catgtagggg cggcagttgg tgcaggtttt cacttttaag ccataaatcg    6600
caagatttta cttaaaaatc aatctcacca tagttgtata aaacagcatc agcatcagtc    6660
atattactga tgctgatgtt ttttatcact taaaccattt taccgctcaa gtgattatct    6720
ttcaccatga ccaaatcgcc attgatcata ggtaaactta ttgagtaaat tttatcaatg    6780
tagttgttag atatggttaa aattgtgcca ttgaccaaaa aattaccgat ttatcccgaa    6840
aatttctgat tatgatcact tttcataaat ttccccaatt tgtctttata aatatcccaa    6900
gaaatggtat tattttattg ccatcagcat atgcgacaac tcatcgtatc atcttttat    6960
cataaaaatg caaataggca tatgcatttt ttgaattgaa cttacgcact gagagatccc    7020
ctcataattt ccccaaagcg taaccatgtg tgaataaatt ttgagctagt agggttgcag    7080
ccacgagtaa gtcttccctt gttattgtgt agccagaatg ccgcaaaact tccatgccta    7140
agcgaactgt tgagagtacg tttcgatttc tgactgtgtt agcctggaag tgcttgtccc    7200
aaccttgttt ctgagcatga acgcccgcaa gccaacatgt tagttgaagc atcagggcga    7260
ttagcagcat gatatcaaaa cgctctgagc tgctcgttcg gctatggcgt aggcctagtc    7320
```

```
cgtaggcagg acttttcaag tctcggaagg tttcttcaat ctgcattcgc ttcgaataga    7380
tattaacaag ttgtttgggt gttcgaattt caacaggtaa gttagttgct agaatccatg    7440
gctcctttgc cgacgctgag tagattttag gtgacgggtg gtgacaatga gtccgtgtcg    7500
agcgctgatt ttttcggcct ttagagcgag atttatacaa tagaatttgg catgagattg    7560
gattgctttt agtcagcctc ttatagccta aagtctttga gtgactagat gacatatcat    7620
gtaagttgct gataggtttc cagttttccg ctcctaggtc tgcatattgt acttttcctc    7680
ttactcgact taaccagtac caacccagct tctcaacgga tttataccat ggcactttaa    7740
agccagcatc actgacaatg agcggtgtgg tgttactcgg tagaatgctc gcaaggtcgg    7800
ctagaaattg gtcatgagct ttctttgaac attgctctga aagcgggaac gctttctcat    7860
aaagagtaac agaacgaccg tgtagtgcga ctgaagctcg caataccata agccgttttt    7920
gctcacggat atcagaccag tcaacaagta caatgggcat cgtattgccc gaacagataa    7980
agctagcatg ccaacggtat acagcgagtc gctctttgtg gaggtgacga ttacctaaca    8040
atcggtcgat tcgtttgatg ttatgttttg ttctcgcttt ggttggcagg ttacggccaa    8100
gttcggtaag agtgagagtt ttacagtcaa gtaaggcgtg gcaagccaac gttaagctgt    8160
tgagtcgttt taagtgtaat tcggggcaga attggtaaag agagtcgtgt aaaatatcga    8220
gttcgcacat tttgttgtct gattattgat ttttggcgaa accatttgat catatgacaa    8280
gatgtgtatc taccttaact taatgatttt gataaaaatc attaggggat tcatcagact    8340
tacgcatctt tcattatggg aattaggtca gtaattatga caaaaaatta tgcattatta    8400
tccgtctcag ataaaacgca aatcgttgaa tttgcccaag gtttggtaga atctggcttt    8460
ggtattttat ccacaggtgg tacttttaaa ctcttaaaag aacatgggat tgacgccatt    8520 gaggttctg cccatacagg ttttgctgaa atgatggatg gtcgtgttaa gaccctacat    8580
cccaaaattc atggtggtat tttgggccgt cgtggcattg atgatgccat tatgaatgaa    8640
catggcattg atcgcattga tatcgttgtc gtgaatttat atccatttgc caacacggtc    8700
gccaaagacg tgttgttat gtctgatgcg attgaaaata ttgatattgg tgggcctgct    8760
atggtacgct cagccgccaa aaatcatgcc catgttggta ttatcaccag cccaaatgac    8820
tactcacgca tcctagatga actaaaaaac caaggtcatt taagccacaa cactcgtttt    8880
gatttggcag tcaaagcatt tgaacacact gccgcctatg atggtatgat tgccagctgg    8940
ctaggtgcac gcttaccagt ggataaagag acggcaccca gtgatgatgc cactgcaacc    9000
actcaatttt cacgcacttt taatcaccaa ttcaccaaag cacaagagct tagatatggc    9060
gaaaacccac atcagtcagc agccttttat gtagatgatc atgcaacaga agcgtctgtt    9120 gcgactcac agcaattaca aggtaaagcg ttgtcttata ataatattgc tgataccgat    9180
gcggcacttg agtgtgtcaa atcttttacc acgcctgctt gtgtgattgt caaacatgcc    9240
aatccttgtg gtgttgcaac atcagaaaac ggtattttag atgcttatca cttagcatat    9300
gcaaccgatc ctgaatctgc ctttggtggc attattgcct ttaaccgaga attagacagt    9360
gatacagccc gtaccatcgt tgagcgtcaa tttgttgaag tcatcatcgc accaagcatc    9420
gctgaaggtg ttctagagcg gccgcgggcc catcgatttt ccacccgggt ggggtaccag    9480
gtaagtgtac ccaattcgcc ctatagtgag tcgtattaca attcactggc cgtcgtttta    9540
ca                                                                   9542
```

<210> SEQ ID NO 9
<211> LENGTH: 2122

```
<212> TYPE: PRT
<213> ORGANISM: Moraxella catarrhalis

<400> SEQUENCE: 9

Met Asn His Ile Tyr Lys Val Ile Phe Asn Lys Ala Thr Gly Thr Phe
1               5                   10                  15

Met Ala Val Ala Glu Tyr Ala Lys Ser His Ser Thr Gly Gly Gly Ser
            20                  25                  30

Cys Ala Thr Gly Gln Val Gly Ser Val Arg Thr Leu Ser Phe Ala Arg
        35                  40                  45

Ile Ala Ala Leu Ala Val Leu Val Ile Gly Ala Thr Leu Asn Gly Ser
    50                  55                  60

Ala Tyr Ala Gly Ile Gly Ile Ser Glu Ala Asp Gly Gly Lys Gly Gly
65                  70                  75                  80

Ala Asn Ala Arg Gly Asp Lys Ser Ile Ala Ile Gly Asp Ile Ala Gln
                85                  90                  95

Ala Leu Gly Ser Gln Ser Ile Ala Ile Gly Asp Asn Lys Ile Val His
            100                 105                 110

Asn Ser Asn Asn Ala Asn Ile Gly Ala Lys Ala Ser Gly Asn Glu
        115                 120                 125

Ser Ile Ala Ile Gly Gly Asp Val Leu Ala Ser Gly His Ala Ser Ile
    130                 135                 140

Ala Ile Gly Ser Asp Asp Leu Tyr Leu Lys Lys Glu Thr Val Gln Gln
145                 150                 155                 160

Ile Ser Glu Leu Leu Pro Ile Ile Arg Gly Gln Lys Ala Leu Asn Asp
                165                 170                 175

Ile Tyr Gln Leu Ala Asp Thr Asn Leu Gln Lys Tyr Arg Arg Thr His
            180                 185                 190

Ala Gln Gly His Ala Ser Thr Ala Val Gly Ala Met Ser Tyr Ala Lys
        195                 200                 205

Gly His Phe Ser Asn Ala Phe Gly Thr Arg Ala Thr Ala Glu Gly Thr
    210                 215                 220

Tyr Ser Leu Ala Val Gly Leu Thr Ala Thr Ala Lys Ala Ala Ser Ser
225                 230                 235                 240

Ile Ala Val Gly Ser Asn Ala Gln Ala Ile Gly Phe Ala Ala Thr Ala
                245                 250                 255

Val Gly Gly Ser Thr Gln Val Asn Leu Asn Arg Gly Ile Ala Leu Gly
            260                 265                 270

Phe Gly Ser Gln Val Leu Gln Lys Asp Asn Asp Val Asn Ala Ala Asn
        275                 280                 285

Val Arg Ala Tyr Ala Pro Asp Asp Asn Gln Pro Ile Asp Asn Arg Tyr
    290                 295                 300

Lys Ala Thr Phe Lys Asn Gly Ala Thr Asp Val Phe Ser Ile Gly Asn
305                 310                 315                 320

Ser Asn Gly Asn Asp Ser Ile Arg Arg Lys Ile Asn Val Gly Ala
                325                 330                 335

Gly Ser Ala Asp Thr Asp Ala Val Asn Val Ala Gln Leu Lys Glu Ala
            340                 345                 350

Val Arg Leu Ala Asn Arg Gln Ile Thr Phe Lys Gly Asp Asp Ser Asn
        355                 360                 365

Asn Arg Val Glu Lys Gly Leu Gly Lys Thr Leu Thr Ile Thr Gly Gly
    370                 375                 380

Ala Gln Thr Ser Ala Leu Thr Asp His Asn Ile Gly Val Val Gln Asn
385                 390                 395                 400
```

-continued

```
Gly Asp Gly Leu Lys Val Gln Leu Ala Glu Thr Leu Thr Ser Leu Lys
                405                 410                 415
Met Val Thr Thr Glu Asn Leu Thr Ala Asn Glu Lys Val Thr Val Gly
            420                 425                 430
Lys Thr Arg Leu Thr Thr Asp Lys Ile Gly Phe Thr Asn Asp Met Asn
        435                 440                 445
Gly Ile Asp Glu Ser Lys Pro Tyr Leu Asp Lys Asp Thr Gly Ile His
    450                 455                 460
Ala Gly Gly Gln Lys Ile Thr Lys Leu Thr Ala Gly Val Val Asp Asp
465                 470                 475                 480
Asp Ala Ala Thr Tyr Gly Gln Leu Lys Lys Val Asn Gln Thr Ala Glu
                485                 490                 495
Ser Ala Leu Gln Thr Phe Thr Val Lys Val Asp Lys Asn Gly Asn
            500                 505                 510
Asp Ala Asn Asp Ser Lys Ile Ile Thr Val Gly Lys Asn Asn Lys Pro
        515                 520                 525
Asp Gly Thr Gln Val Asn Thr Leu Lys Leu Lys Gly Glu Asn Gly Val
    530                 535                 540
Asp Val Thr Thr Glu Thr Asn Gly Thr Val Thr Phe Gly Leu Asn Gln
545                 550                 555                 560
Asn Asn Gly Leu Thr Val Gly Asn Ser Thr Leu Asn Asn Asp Gly Leu
                565                 570                 575
Ser Val Lys Asn Thr Asn Ser Asn Lys Gln Ile Gln Val Gly Ala Asp
            580                 585                 590
Gly Ile Thr Phe Thr Asp Ile Ser Asn Ser Lys Pro Gly Ala Gly Ile
        595                 600                 605
Glu Asn Thr Thr Arg Ile Thr Arg Asp Gly Ile Gly Phe Ala Asn Asn
    610                 615                 620
Thr Gly Ser Leu Asp Ala Asn Lys Pro Arg Leu Thr Pro Thr Gly Ile
625                 630                 635                 640
Asn Ala Gly Gly Lys Glu Leu Thr Asn Val Gln Ser Ala Ile Asn Pro
                645                 650                 655
Ala Thr Asn Gly Gly Gln Leu Asp Phe Met Asn Arg Leu Ser Thr Ala
            660                 665                 670
Asn Thr Glu Lys Ser Gly Ser Ala Ala Thr Ile Lys Asp Leu Tyr Asn
        675                 680                 685
Leu Ser Gln Val Pro Leu Thr Phe Ala Gly Asp Thr Gly Pro Asn Val
    690                 695                 700
Thr Lys Lys Leu Gly Glu Ile Leu Lys Val Lys Gly Gly Lys Thr Thr
705                 710                 715                 720
Ala Asp Asp Leu Thr Lys Asn Asn Ile Gly Val Val Ala Asp Ser Thr
                725                 730                 735
Asp Asn Ser Leu Thr Val Lys Leu Ala Lys Thr Leu Ser Asp Leu Asp
            740                 745                 750
Ala Val Asn Thr Lys Thr Leu Thr Ala Ser Asp Lys Val Thr Val Asp
        755                 760                 765
Ser Gly Asn Asn Thr Ala Lys Leu Gln Asn Gly Asp Leu Thr Phe Ser
    770                 775                 780
Lys Gln Asn Thr Gly Ala Thr Pro Ala Thr Asn Ser Lys Thr Ile Gly
785                 790                 795                 800
Val Asp Gly Leu Lys Phe Thr Asp Asn Asn Gly Ile Ala Leu Asp Gly
                805                 810                 815
```

```
Thr Thr Tyr Ile Thr Lys Asp Lys Val Gly Phe Ala Lys Gln Asp Gly
                820             825             830

Ser Leu Asp Lys Ser Lys Pro Tyr Leu Asp Lys Asp Lys Leu Lys Val
            835             840             845

Gly Glu Val Glu Ile Thr Thr Asn Gly Ile Asn Ala Gly Gly Lys Ala
        850             855             860

Ile Thr Gly Leu Ser Asn Thr Leu Thr Asp Ala Thr Asn Ala Thr Thr
865             870             875             880

Gly His Val Thr Gln Leu Gly Ile Val Asp Ser Thr Asp Lys Thr Arg
                885             890             895

Ala Ala Ser Ile Gly Asp Val Leu Asn Ala Gly Phe Asn Leu Lys Asn
            900             905             910

Asn Gly Asp Ala Lys Asp Phe Val Ser Thr Tyr Asp Thr Val Asp Phe
        915             920             925

Ile Asn Gly Asn Ala Thr Thr Ala Lys Val Thr Tyr Asp Gly Lys Ala
930             935             940

Ser Lys Val Ala Tyr Asp Val Asn Val Asp Gly Thr Thr Ile His Leu
945             950             955             960

Thr Gly Ala Asp Gly Asn Lys Asn Gln Ile Gly Val Lys Thr Thr Thr
                965             970             975

Leu Thr Lys Thr Asp Ala Lys Gly Asp Lys Ala Ile Asn Phe Ser Val
            980             985             990

Asn Ser Gly Asp Asp Lys Ala Leu Ile Asn Ala Lys Asp Ile Ala Asp
        995             1000            1005

Asn Leu Asn Thr Leu Ala Gly Glu Ile Arg Asn Thr Lys Gly Thr
        1010            1015            1020

Ala Asp Thr Ala Leu Gln Thr Phe Gln Val Lys Lys Val Lys Glu
    1025            1030            1035

Asn Gly Asp Asp Asp Asn Asp Ala Asp Thr Ile Thr Val Gly Lys
    1040            1045            1050

Asp Ala Lys Thr Asn Gln Val Asn Thr Leu Lys Leu Lys Gly Lys
    1055            1060            1065

Asn Gly Leu Asp Ile Gln Thr Asn Lys Asp Gly Thr Val Thr Phe
    1070            1075            1080

Gly Ile Asn Thr Gln Ser Gly Leu Lys Ala Gly Asn Asn Thr Thr
    1085            1090            1095

Leu Asn Asn Asn Gly Leu Ser Ile Lys Asn Thr Ala Gly Asn Glu
    1100            1105            1110

Gln Ile Gln Val Gly Ala Asp Gly Val Lys Phe Ala Lys Val Asn
    1115            1120            1125

Asn Gly Val Val Gly Ala Gly Ile Asp Gly Thr Thr Arg Ile Thr
    1130            1135            1140

Arg Asp Glu Ile Gly Phe Ala Gly Thr Asn Gly Ser Leu Asp Lys
    1145            1150            1155

Ser Lys Pro His Leu Ser Lys Asp Gly Ile Asn Ala Gly Gly Lys
    1160            1165            1170

Lys Ile Thr Asn Ile Gln Ser Gly Glu Ile Ala Gln Asn Ser Asn
    1175            1180            1185

Asp Ala Val Thr Gly Gly Lys Ile Tyr Asp Leu Lys Thr Glu Leu
    1190            1195            1200

Glu Asn Lys Ile Ser Ser Thr Ala Lys Thr Ala Gln Asn Ser Leu
    1205            1210            1215

His Glu Phe Ser Val Ala Asp Glu Gln Gly Asn Asn Phe Thr Val
```

-continued

```
        1220                1225                1230
Ser Asn Pro Tyr Ser Ser Tyr Asp Thr Ser Lys Thr Ser Asp Val
    1235                1240                1245
Ile Thr Phe Ala Gly Glu Asn Gly Ile Thr Thr Lys Val Asn Lys
    1250                1255                1260
Gly Val Val Arg Val Gly Ile Asp Gln Thr Lys Gly Leu Thr Thr
    1265                1270                1275
Pro Lys Leu Thr Val Gly Asn Asn Gly Lys Gly Ile Val Ile
    1280                1285                1290
Asp Ser Gln Asn Gly Gln Asn Thr Ile Thr Gly Leu Ser Asn Thr
    1295                1300                1305
Leu Ala Asn Val Thr Asn Asp Lys Gly Ser Val Arg Thr Thr Glu
    1310                1315                1320
Gln Gly Lys Ile Ile Lys Asp Glu Asp Lys Thr Arg Ala Ala Ser
    1325                1330                1335
Ile Val Asp Val Leu Ser Ala Gly Phe Asn Leu Gln Gly Asn Gly
    1340                1345                1350
Glu Ala Val Asp Phe Val Ser Thr Tyr Asp Thr Val Asn Phe Ala
    1355                1360                1365
Asp Gly Asn Ala Thr Thr Ala Lys Val Thr Tyr Asp Asp Thr Ser
    1370                1375                1380
Lys Thr Ser Lys Val Val Tyr Asp Val Asn Val Asp Asp Thr Thr
    1385                1390                1395
Ile Glu Val Lys Asp Lys Lys Leu Gly Val Lys Thr Thr Thr Leu
    1400                1405                1410
Thr Ser Thr Gly Thr Gly Ala Asn Lys Phe Ala Leu Ser Asn Gln
    1415                1420                1425
Ala Thr Gly Asp Ala Leu Val Lys Ala Ser Asp Ile Val Ala His
    1430                1435                1440
Leu Asn Thr Leu Ser Gly Asp Ile Gln Thr Ala Lys Gly Ala Ser
    1445                1450                1455
Gln Ala Asn Ser Ser Ala Gly Tyr Val Asp Ala Asp Gly Asn Lys
    1460                1465                1470
Val Ile Tyr Asp Ser Thr Asp Asn Lys Tyr Tyr Gln Ala Lys Asn
    1475                1480                1485
Asp Gly Thr Val Asp Lys Thr Lys Glu Val Ala Lys Asp Lys Leu
    1490                1495                1500
Val Ala Gln Ala Gln Thr Pro Asp Gly Thr Leu Ala Gln Met Asn
    1505                1510                1515
Val Lys Ser Val Ile Asn Lys Glu Gln Val Asn Asp Ala Asn Lys
    1520                1525                1530
Lys Gln Gly Ile Asn Glu Asp Asn Ala Phe Val Lys Gly Leu Glu
    1535                1540                1545
Lys Ala Ala Ser Asp Asn Lys Thr Lys Asn Ala Ala Val Thr Val
    1550                1555                1560
Gly Asp Leu Asn Ala Val Ala Gln Thr Pro Leu Thr Phe Ala Gly
    1565                1570                1575
Asp Thr Gly Thr Thr Ala Lys Lys Leu Gly Glu Thr Leu Thr Ile
    1580                1585                1590
Lys Gly Gly Gln Thr Asp Thr Asn Lys Leu Thr Asp Asn Asn Ile
    1595                1600                1605
Gly Val Val Ala Gly Thr Asp Gly Phe Thr Val Lys Leu Ala Lys
    1610                1615                1620
```

```
Asp Leu Thr Asn Leu Asn Ser Val Asn Ala Gly Gly Thr Lys Ile
    1625                1630                1635

Asp Asp Lys Gly Val Ser Phe Val Asp Ser Ser Gly Gln Ala Lys
    1640                1645                1650

Ala Asn Thr Pro Val Leu Ser Ala Asn Gly Leu Asp Leu Gly Gly
    1655                1660                1665

Lys Val Ile Ser Asn Val Gly Lys Gly Thr Lys Asp Thr Asp Ala
    1670                1675                1680

Ala Asn Val Gln Gln Leu Asn Glu Val Arg Asn Leu Leu Gly Leu
    1685                1690                1695

Gly Asn Ala Gly Asn Asp Asn Ala Asp Gly Asn Gln Val Asn Ile
    1700                1705                1710

Ala Asp Ile Lys Lys Asp Pro Asn Ser Gly Ser Ser Ser Asn Arg
    1715                1720                1725

Thr Val Ile Lys Ala Gly Thr Val Leu Gly Gly Lys Gly Asn Asn
    1730                1735                1740

Asp Thr Glu Lys Leu Ala Thr Gly Gly Val Gln Val Gly Val Asp
    1745                1750                1755

Lys Asp Gly Asn Ala Asn Gly Asp Leu Ser Asn Val Trp Val Lys
    1760                1765                1770

Thr Gln Lys Asp Gly Ser Lys Lys Ala Leu Leu Ala Thr Tyr Asn
    1775                1780                1785

Ala Ala Gly Gln Thr Asn Tyr Leu Thr Asn Asn Pro Ala Glu Ala
    1790                1795                1800

Ile Asp Arg Ile Asn Glu Gln Gly Ile Arg Phe Phe His Val Asn
    1805                1810                1815

Asp Gly Asn Gln Glu Pro Val Val Gln Gly Arg Asn Gly Ile Asp
    1820                1825                1830

Ser Ser Ala Ser Gly Lys His Ser Val Ala Ile Gly Phe Gln Ala
    1835                1840                1845

Lys Ala Asp Gly Glu Ala Ala Val Ala Ile Gly Arg Gln Thr Gln
    1850                1855                1860

Ala Gly Asn Gln Ser Ile Ala Ile Gly Asp Asn Ala Gln Ala Thr
    1865                1870                1875

Gly Asp Gln Ser Ile Ala Ile Gly Thr Gly Asn Val Val Ala Gly
    1880                1885                1890

Lys His Ser Gly Ala Ile Gly Asp Pro Ser Thr Val Lys Ala Asp
    1895                1900                1905

Asn Ser Tyr Ser Val Gly Asn Asn Gln Phe Thr Asp Ala Thr
    1910                1915                1920

Gln Thr Asp Val Phe Gly Val Gly Asn Asn Ile Thr Val Thr Glu
    1925                1930                1935

Ser Asn Ser Val Ala Leu Gly Ser Asn Ser Ala Ile Ser Ala Gly
    1940                1945                1950

Thr His Ala Gly Thr Gln Ala Lys Lys Ser Asp Gly Thr Ala Gly
    1955                1960                1965

Thr Thr Thr Thr Ala Gly Ala Thr Gly Thr Val Lys Gly Phe Ala
    1970                1975                1980

Gly Gln Thr Ala Val Gly Ala Val Ser Val Gly Ala Ser Gly Ala
    1985                1990                1995

Glu Arg Arg Ile Gln Asn Val Ala Ala Gly Glu Val Ser Ala Thr
    2000                2005                2010
```

```
Ser Thr Asp Ala Val Asn Gly Ser Gln Leu Tyr Lys Ala Thr Gln
    2015                2020                2025

Gly Ile Ala Asn Ala Thr Asn Glu Leu Asp His Arg Ile His Gln
    2030                2035                2040

Asn Glu Asn Lys Ala Asn Ala Gly Ile Ser Ala Met Ala Met
    2045                2050                2055

Ala Ser Met Pro Gln Ala Tyr Ile Pro Gly Arg Ser Met Val Thr
    2060                2065                2070

Gly Gly Ile Ala Thr His Asn Gly Gln Gly Ala Val Ala Val Gly
    2075                2080                2085

Leu Ser Lys Leu Ser Asp Asn Gly Gln Trp Val Phe Lys Ile Asn
    2090                2095                2100

Gly Ser Ala Asp Thr Gln Gly His Val Gly Ala Ala Val Gly Ala
    2105                2110                2115

Gly Phe His Phe
    2120

<210> SEQ ID NO 10
<211> LENGTH: 7
<212> TYPE: PRT
<213> ORGANISM: Moraxella catarrhalis

<400> SEQUENCE: 10

Gly Thr Val Leu Gly Gly Lys
1               5

<210> SEQ ID NO 11
<211> LENGTH: 40
<212> TYPE: PRT
<213> ORGANISM: Moraxella catarrhalis

<400> SEQUENCE: 11

Gly Ile Gly Ile Ser Glu Ala Asp Gly Gly Lys Gly Gly Ala Asn Ala
1               5                   10                  15

Arg Gly Asp Lys Ser Ile Ala Ile Gly Asp Ile Ala Gln Ala Leu Gly
            20                  25                  30

Ser Gln Ser Ile Ala Ile Gly Asp
        35                  40

<210> SEQ ID NO 12
<211> LENGTH: 24
<212> TYPE: PRT
<213> ORGANISM: Moraxella catarrhalis

<400> SEQUENCE: 12

Glu Ala Asp Gly Gly Lys Gly Gly Ala Asn Ala Arg Gly Asp Lys Ser
1               5                   10                  15

Ile Ala Ile Gly Asp Ile Ala Gln
            20

<210> SEQ ID NO 13
<211> LENGTH: 18
<212> TYPE: DNA
<213> ORGANISM: Artificial Sequence
<220> FEATURE:
<223> OTHER INFORMATION: oligonucleotide PCR primer
<220> FEATURE:
<221> NAME/KEY: misc_feature
<222> LOCATION: (1)..(18)
<223> OTHER INFORMATION: n is a, c, g or t

<400> SEQUENCE: 13
```

```
gargcngayg gnggnaar                                                         18

<210> SEQ ID NO 14
<211> LENGTH: 18
<212> TYPE: DNA
<213> ORGANISM: Artificial Sequence
<220> FEATURE:
<223> OTHER INFORMATION: oligonucleotide PCR primer
<220> FEATURE:
<221> NAME/KEY: misc_feature
<222> LOCATION: (1)..(18)
<223> OTHER INFORMATION: n is a, c, g or t

<400> SEQUENCE: 14
ytgngcdatr tcnccdat                                                         18

<210> SEQ ID NO 15
<211> LENGTH: 18
<212> TYPE: DNA
<213> ORGANISM: Moraxella catarrhalis

<400> SEQUENCE: 15
gaagcggacg gggggaaa                                                         18

<210> SEQ ID NO 16
<211> LENGTH: 18
<212> TYPE: DNA
<213> ORGANISM: Moraxella catarrhalis

<400> SEQUENCE: 16
ttgcgcaatg tcaccaat                                                         18

<210> SEQ ID NO 17
<211> LENGTH: 72
<212> TYPE: DNA
<213> ORGANISM: Moraxella catarrhalis

<400> SEQUENCE: 17
gaagcggacg gggggaaagg cggagccaat gcgcgcggtg ataaatccat tgctattggt          60
gacattgcgc aa                                                               72

<210> SEQ ID NO 18
<211> LENGTH: 24
<212> TYPE: PRT
<213> ORGANISM: Moraxella catarrhalis

<400> SEQUENCE: 18

Glu Ala Asp Gly Gly Lys Gly Gly Ala Asn Ala Arg Gly Asp Lys Ser
1               5                   10                  15

Ile Ala Ile Gly Asp Ile Ala Gln
            20

<210> SEQ ID NO 19
<211> LENGTH: 29
<212> TYPE: DNA
<213> ORGANISM: Moraxella catarrhalis

<400> SEQUENCE: 19
catcattgga aaacgttctt cggggcgaa                                             29

<210> SEQ ID NO 20
<211> LENGTH: 20
<212> TYPE: DNA
```

```
-continued
<213> ORGANISM: Moraxella catarrhalis

<400> SEQUENCE: 20
cggtcagctt aggcgtggtt                                              20
```

What is claimed is:

1. An isolated or substantially pure OMP106 polypeptide, which is an outer membrane polypeptide of *Moraxella catarrhalis*, and which has a molecular weight of about 180 kD to about 230 kD as determined in SDS polyacrylamide gel electrophoresis using rabbit skeletal muscle myosin and *E. coli* β-galactosidase as the 200 kD and 116.25 kD molecular weight standards, respectively, and which comprises the amino acid sequence of SEQ ID NO: 1.

2. The OMP106 polypeptide of claim 1, which has a molecular weight of about 190 kD.

3. The OMP106 polypeptide of claim 1, wherein the *Moraxella catarrhalis* is a hemagglutinating cultivar.

4. An immunogenic composition comprising an isolated or substantially pure OMP106 polypeptide, which is an outer membrane polypeptide of *Moraxella catarrhalis*, and which has a molecular weight of about 180 kD to about 230 kD as determined in SDS polyacrylamide gel electrophoresis using rabbit skeletal muscle myosin and *E. coli* β-galactosidase as the 200 kD and 116.25 kD molecular weight standards, respectively, and which comprises the amino acid sequence of SEQ ID NO: 1, or SEQ ID NO: 9.

5. The composition of claim 4, further comprising an adjuvant.

* * * * *